United States Patent
VanDyck et al.

(10) Patent No.: US 10,450,270 B2
(45) Date of Patent: Oct. 22, 2019

(54) GLYOXAMIDE SUBSTITUTED PYRROLAMIDE DERIVATIVES AND THE USE THEREOF AS MEDICAMENTS FOR THE TREATMENT OF HEPATITIS B

(71) Applicant: Janssen Sciences Ireland UC, Co Cork (IE)

(72) Inventors: Koen VanDyck, Paal-Beringen (BE); Bart Rudolf Romanie Kesteleyn, Berlare (BE); Serge Maria Aloysius Pieters, Hulst (NL); Geert Rombouts, Borsbeek (BE); Wim Gaston Verschueren, Berchem (BE); Pierre Jean-Marie Bernard Raboisson, Rosieres (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 14/907,109

(22) PCT Filed: Jul. 25, 2014

(86) PCT No.: PCT/EP2014/066093
§ 371 (c)(1),
(2) Date: Jan. 22, 2016

(87) PCT Pub. No.: WO2015/011281
PCT Pub. Date: Jan. 29, 2015

(65) Prior Publication Data
US 2016/0176817 A1  Jun. 23, 2016

(30) Foreign Application Priority Data

Jul. 25, 2013 (EP) .................................. 13177926
Jun. 4, 2014 (EP) .................................. 14171062

(51) Int. Cl.
| | | |
|---|---|---|
| C07D 207/34 | (2006.01) | |
| C07D 401/12 | (2006.01) | |
| C07D 405/12 | (2006.01) | |
| A61K 31/40 | (2006.01) | |
| A61K 31/4025 | (2006.01) | |
| A61K 31/454 | (2006.01) | |
| A61P 31/00 | (2006.01) | |

(52) U.S. Cl.
CPC ............ *C07D 207/34* (2013.01); *A61K 31/40* (2013.01); *A61K 31/4025* (2013.01); *A61K 31/454* (2013.01); *A61P 31/00* (2018.01); *C07D 401/12* (2013.01); *C07D 405/12* (2013.01)

(58) Field of Classification Search
CPC .. A61K 31/40; A61K 31/4025; A61K 31/454; C07D 207/34; C07D 401/12; C07D 405/12
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |

(Continued)

FOREIGN PATENT DOCUMENTS

| | | |
|---|---|---|
| CA | 2950807 A1 | 12/2013 |
| CL | 201403227 | 2/2015 |

(Continued)

OTHER PUBLICATIONS

Weber, O., et al., "Inhibition of Human Hepatitis B Virus HBV) by a Novel Non-Nucleosidic Compound in a Transgenic Mouse Model", Antiviral Research, vol. 54 p. 69-78 (2002).

(Continued)

*Primary Examiner* — Valerie Rodriguez-Garcia

(57) ABSTRACT

Inhibitors of HBV replication of Formula (IA)

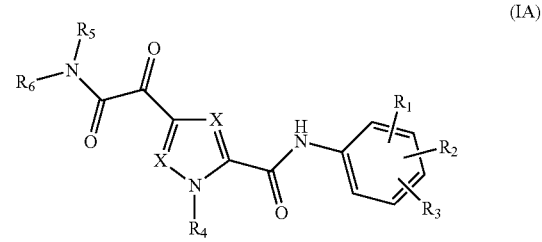

(IA)

including stereochemically isomeric forms, and salts, hydrates, solvates thereof, wherein X and $R^1$ to $R^6$ have the meaning as defined herein.

The present invention also relates to processes for preparing said compounds, pharmaceutical compositions containing them and their use, alone or in combination with other HBV inhibitors, in HBV therapy.

20 Claims, No Drawings

(56) References Cited

U.S. PATENT DOCUMENTS

| | | |
|---|---|---|
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,071,961 B2 | 9/2018 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams et al. |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 1390201 A | 1/2003 |
| CN | 101039919 A | 9/2007 |
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |
| JP | 2008525406 A | 7/2008 |
| JP | 2010535172 A | 11/2010 |
| WO | 198403281 A1 | 8/1984 |
| WO | 199207835 A1 | 5/1992 |
| WO | 1998023285 A1 | 6/1998 |

(56) References Cited

FOREIGN PATENT DOCUMENTS

| | | |
|---|---|---|
| WO | 199909022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | 2008054605 A2 | 7/2008 |
| WO | 2008093614 A1 | 8/2008 |
| WO | 2008137794 A1 | 11/2008 |
| WO | 2008154819 A1 | 12/2008 |
| WO | 2009016088 A1 | 2/2009 |
| WO | 2009018219 A2 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | WO 2013/006394 A1 | 1/2013 |
| WO | WO 2013/096744 A1 | 6/2013 |
| WO | 2013102655 A1 | 7/2013 |
| WO | 2013130703 A2 | 9/2013 |
| WO | 2013144129 A1 | 10/2013 |
| WO | 2013174962 | 11/2013 |
| WO | 2013181584 A2 | 12/2013 |
| WO | 2013184757 A1 | 12/2013 |
| WO | 2014033167 A1 | 3/2014 |
| WO | 2014033176 | 3/2014 |
| WO | 2014037480 A1 | 3/2014 |
| WO | WO 2014/033170 A1 | 3/2014 |
| WO | WO 2014/033176 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | WO 2019011323 A1 | 1/2019 |

OTHER PUBLICATIONS

International Search Report mailed Sep. 8, 2014 for corresponding Application No. PCT/EP2014/066093.
Online Registry Via STN Dec. 22, 2008, RN 1088200-12-7.
Online Registry Via STN, Mar. 2, 2007, RN 924514-21-6.
Online Registry Via STN, Sep. 2, 2003, RN 577752-12-6.
Bennes, et al., "Recognition-induced control and acceleration of a pyroole Diels-Alder reaction", Tetrahedron Letters, vol. 42: pp. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-e21 (Feb. 2016).
Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).
Cai, et al., "Identification of disubstituted sulfonamide compounds as specific inhibitors of hepatitis B virus covalently closed circular DNA formuation, Antimicrobial agents and chemotherapy", pp. vol. 56(8): pp. 4277-4288 (May 29, 2012).
Campagna et al., "Sulfamoylbenzamide Derivatives Inhibit the Assembly of Hepatitis B Virus Nucleocapsids", Journal of Virology, ), vol. 87 (12): pp. 6931-6942 (Jun. 2013).
Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).
Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).

(56) References Cited

OTHER PUBLICATIONS

Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an urgent global public health priority demanding action", Antiviral Therapy, vol. 18: pp. 953-954 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Effecient Synthesis of 2-Chloro-3-carboethoxy or 2-Chloro-3-cyano- 4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Geies, et al., Synthesis of some Thiazolo-[3,2-a]Pyrimidines, Phosphorus, Sulfur and Silicon, vol. 56: pp. 87-93 (1991).
Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al, "Discovery of potent, selective sulfonylfuran urea endothelial lipase inhibitors", Bioorganic & Medicinal Chemistry Letters, vol. 19: pp. 27-30 (2009).
Guo, et al., "HBc binds to the CpG island of HBV cccDNA and promotes an epigenetic permissive state", Epigenetics, vol. 6 (6): pp. 720-726 (Jun. 2011).
Hogan, et al., "Aqueous Process Chemistry: The Preparation of Aryl Sulfonyl Chlorides", Organic Process Research & Development, vol. 13: pp. 875-879 (2009).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, (Oct. 2016).
Hughes, et al., "Hepatitis Delta Virus", The Lancet, vol. 378: pp. 73-85, (Jul. 2, 2011).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).

Klumpp, et al., "High Antiviral Activity of the HBV Core Inhibitor NVR 3-778 in the Humanized UPA/SCID Mouse Model", Journal of Hepatology, vol. 62: p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009.
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Online Registr Via STN, Dec. 28, 2008, RN 1090750-88-1.
Online Registry Via STN Aug. 6, 2012. RN 1386725-02-5.
Online Registry Via STN Jun. 7, 2012, Rn 1375909-37-7.
Online Registry Via STN Oct. 10, 2001, RN 361373-90-2.
Online Registry Via STN Aug. 13, 2012, RN 1390500-09-0.
Online Registry Via STN Jan. 16, 2001, RN 314043-17-9.
Online Registry Via STN 2010, RN 1253220-91-5.
Online Registry Via STN Aug. 30, 2011, RN 1325664-90-1.
Online Registry Via STN, Jan. 24, 2008, RN 296790-26-6.
Online Registry Via STN, Feb. 2, 2007, RN 9019040-48-5.
Online Registry Via STN, May 6, 2011, RN 1291044-81-9.
Online Registry Via STN, Oct. 7, 2008, RN 1057788-44-9.
Online Registry Via STN, Oct. 7, 2008, RN 1057871-39-2.
Online Registry Via STN, Jan. 9, 2001, RN 313253-89-3.
Online Registry Via STN, Mar. 10, 2010, RN 1208400-27-4.
Online Registry Via STN, Feb. 15, 2007, RN 921179-95-5.
Online Registry Via STN, Aug. 15, 2011, RN 1317923-24-2.
Online Registry Via STN, Aug. 15, 2011, RN 1318022-74-0.
Online Registry Via STN, Mar. 17, 2003, RN 499189-09-2.
Online Registry Via STN, May 18, 2011, RN 1296380-95-4.
Online Registry Via STN, Oct. 18, 2000, RN 296894-70-7.
Online Registry Via STN, Sep. 20, 2013, RN 1452780-00-5.
Online Registry Via STN, Apr. 24, 2002, RN 406926-60-1.

(56) References Cited

OTHER PUBLICATIONS

Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schroder, et al., "Arzneimittelchemie Passage", Arzneimittelchemei Grundlagen Nerven Musklen und Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41-4109 has multiple effects on Hepatitis B virus capsid assembly", Journal of Molecular Recognition, vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al., "In vitro inhibition of HBV replication by a novel compound, GLS4, and its efficacy against adefovir-dipovoxil-resistant HBV mutations", Antiviral Therapy, vol. 17: pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber et al., "Inhibition of Human Hepatitis B Virus (HBV) by a Novel Non-Nucleosidic Compound in a Transgenic Mouse Model", Antiviral Research, vol. 54: pp. 69-78 (2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), In treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 82-93 (2015).
Zoulim, et al., "Current Treatments for Chronic Hepatitis B Virus Infections", Current Opinion in Virology, vol. 18: pp. 109-116 (2016).
Carver, et al., Polyfunctionalisation of Imidazole via Sequential Imidazolyl Anion Formation, Tetrahedron, 1997, pp. 14481-14496, vol. 53 Issue 42.
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Online Registry Via STN, Aug. 13, 2012, RN 1390589-54-4.
Online Registry Via STN Feb. 2, 2007, RN 919040-39-4.
Online Registry Via STN Feb. 2, 2007, RN 919040-53-2.
Online Registry Via STN Feb. 2, 2007, RN 919040-55-4.
Online Registry Via STN Dec. 8, 2012, RN 1389720-57-3.
Online Registry Via STN Dec. 11, 2007, RN 957487-45-5.
Online Registry Via STN Dec. 11, 2007, RN 957487-49-9.
Online Registry Via STN Aug. 12, 2012, RN 1389686-79-6.
Online Registry Via STN Mar. 17, 2013, RN 1424462-66-7.
Online Registry Via STN Sep. 18, 2012, RN 1394742-82-5.
Online Registry Via STN, Feb. 2, 2007, RN 919040-37-2.
Online Registry Via STN, Sep. 6, 2011, RN 1328738-57-3.
Online Registry Via STN, Apr. 28, 2011, RN 1286906-97-5.
Online Registry Via STN. Apr. 19, 2006, RN 930914-71-9.
You et al, Pharmaceutical Chemistry, Chemical Industry Press, Jan. 31, 2014, pp. 32-33.
Horig, et al., from bemnch to Clinic and back: Perspective on the 1st IQPC translational Research conference, Journal of translational medicine, Dec. 20, 2004, pp. 1-8, vol. 2 Issue 44.
Mohebbi, et al., An Overview of Hepatitis B Virus Surface Antigen Secreation Inhibitors, Frontier in Microbiology, 2018, pp. 1-9, vol. 9.
Schafer, et al., Failure Is option: learning from unsuccessful proof-ofconcepts trails, Drug Discovery Today, 2008, pp. 913-916, vol. 13 Issue 21/22.
Horig, et al., "From bench to Clinic and back: Perspective on the 1st IQPC translational Research conference", Journal of Translational Medicine, vol. 2(44): pp. 1-8 (Dec. 20, 2004).
Mohebbi, et al., "An Overview of Hepatitis B Virus Surface Antigen Secretion Inhibitors", Frontier in Microbiology, vol. 9: pp. 1-9 (Apr. 2018).
Online Registry Via STN Feb. 3, 2012, RN 1359583-56-4.
Online Registry Via STN Feb. 3, 2012, RN 1359596_55_6.
Schafer; et al., "Failure is an Option: Learning from unsuccessful proof-of-concepts trails", Drug Discovery Today, vol. 13 (21/22): pp. 913-916 (Nov. 2008).
Nijampatnam et al., "Recent advances in the development of HBV capsid assembly modulators", Current Opinion in Chemical Biology, vol. 50; pp. 73-79 (2019).

GLYOXAMIDE SUBSTITUTED PYRROLAMIDE DERIVATIVES AND THE USE THEREOF AS MEDICAMENTS FOR THE TREATMENT OF HEPATITIS B

CROSS-REFERENCE TO RELATED APPLICATIONS

This application is the national stage filing under USC 371 of international application PCT/EP2014/066093 filed on Jul. 25, 2014, which claims priority to European Patent Application No. 13177926.6 filed Jul. 25, 2013, and European Patent Application No. 14171062.4 filed Jun. 4, 2014, the complete disclosures of which are hereby incorporated herein by reference for all purposes.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013, relates to a subclass of Sulphamoyl-arylamides active against HBV. WO2013/096744, published on Jun. 26, 2013 relates to compounds active against HBV.

In addition, WO2014/033170 and WO2014/033176, published on Mar. 6, 2014 relate further compounds active against HBV.

Amongst the problems which HBV direct antivirals may encounter are toxicity, mutagenicity, lack of selectivity, poor efficacy, poor bioavailability, low solubility and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to a compound of Formula (IA)

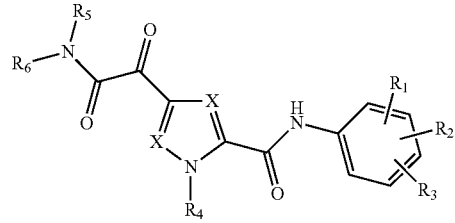

or a stereoisomer or tautomeric form thereof, wherein:
Each X independently represents $CR^7$;
$R^1$, $R^2$ and $R^3$ are independently selected from the group consisting of Hydrogen, Fluoro, Chloro, Bromo, $-CHF_2$, $-CH_2F$, $-CF_3$, $-CN$, $C_1$-$C_3$alkyl or $C_3$-$C_4$cycloalkyl;
$R^4$ is Hydrogen $C_1$-$C_3$alkyl or $C_3$-$C_4$cycloalkyl;
$R^5$ is Hydrogen;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_3$-$C_4$cycloalkyl, $-OR^8$, oxo, $-CN$, $-C(=O)-OR^8$, $-C(=O)-N(R^8)_2$ or $C_1$-$C_3$alkyl optionally substituted with one or more Fluoro;
Each $R^7$ independently represents hydrogen, $C_3$-$C_4$cycloalkyl, $-CN$, Fluoro, Chloro, Bromo or $C_1$-$C_3$alkyl optionally substituted with one or more Fluoro;
$R^8$ represents hydrogen or $C_1$-$C_3$alkyl;
or a pharmaceutically acceptable salt or a solvate thereof.

The invention further relates to a pharmaceutical composition comprising a compound of Formula (IA), and a pharmaceutically acceptable carrier.

The invention also relates to the compounds of Formula (IA) for use as a medicament, preferably for use in the prevention or treatment of an HBV infection in a mammal.

In a further aspect, the invention relates to a combination of a compound of Formula (IA), and another HBV inhibitor.

DEFINITIONS

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radicals having from 1 to 4 carbon atoms such as the group defined for $C_{1-3}$alkyl and butyl and the like.

$C_{1-6}$alkyl as a group or part of a group defines straight or branched chain saturated hydrocarbon radicals having from 1 to 6 carbon atoms, such as the groups defined for $C_{1-4}$alkyl and pentyl, hexyl, 2-methylbutyl and the like.

As used herein, the term "3-7 membered saturated ring" means saturated cyclic hydrocarbon with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbon with 3 or 4 carbon atoms and 1 oxygen atom. Examples include oxetane, and tetrahydrofuranyl.

It should be noted that different isomers of the various heterocycles may exist within the definitions as used throughout the specification. For example, pyrrolyl may be 1H-pyrrolyl or 2H-pyrrolyl.

The term halo and halogen are generic to Fluoro, Chloro, Bromo or Iodo. Preferred halogens are Fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

Positions indicated on phenyl (e.g. ortho, meta and/or para) are indicated relative to the bond connecting the phenyl to the main structure. An example with regard to the position of any location is indicated relative to the nitrogen (*) connected to the main structure:

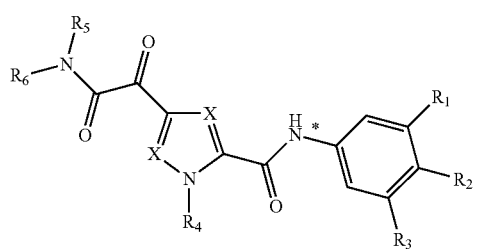

(I)

When any variable (e.g. halogen or $C_{1-3}$alkyl) occurs more than one time in any constituent, each definition is independent.

For therapeutic use, the salts of the compounds of Formula (IA) are those wherein the counter ion is pharmaceutically or physiologically acceptable. However, salts having a pharmaceutically unacceptable counter ion may also find use, for example, in the preparation or purification of a pharmaceutically acceptable compound of Formula (IA). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric forms of Formula (IA) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds.

Isotopes include those atoms having the same atomic number but different mass numbers. By way of general example and without limitation, isotopes of Hydrogen include tritium and deuterium. Isotopes of carbon include C-13 and C-14.

DETAILED DESCRIPTION OF THE INVENTION

Whenever used hereinafter, the term "compounds of formula (IA)",

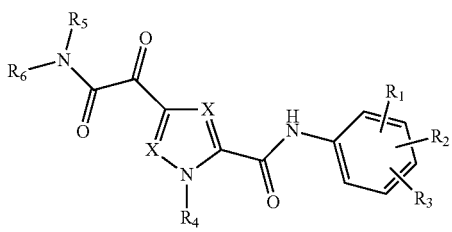
(IA)

or "the present compounds" or similar term is meant to include the compounds of general formula (IA), (I), (Ia), (Ib), salts, stereoisomeric forms and racemic mixtures or any subgroups thereof.

In a first aspect, the invention provides compound of Formula (IA)

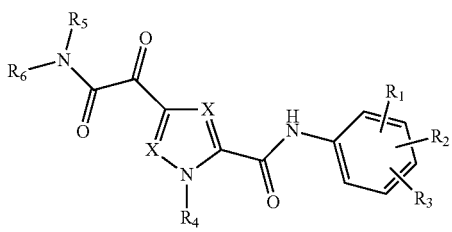
(IA)

or a stereoisomer or tautomeric form thereof, wherein:
Each X independently represents $CR^7$;
$R^1$, $R^2$ and $R^3$ are independently selected from the group consisting of Hydrogen, Fluoro, Chloro, Bromo, —$CHF_2$, —$CH_2F$, —$CF_3$, —CN, $C_1$-$C_3$alkyl or $C_3$-$C_4$cycloalkyl;
$R^4$ is Hydrogen $C_1$-$C_3$alkyl or $C_3$-$C_4$cycloalkyl;
$R^5$ is Hydrogen;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_3$-$C_4$cycloalkyl, —$OR^8$, oxo, —CN, —C(=O)—$OR^8$, —C(=O)—$N(R^8)_2$ or $C_1$-$C_3$alkyl optionally substituted with one or more Fluoro;
Each $R^7$ independently represents hydrogen, $C_3$-$C_4$cycloalkyl, —CN, Fluoro, Chloro, Bromo or $C_1$-$C_3$alkyl optionally substituted with one or more Fluoro;
$R^8$ represents hydrogen or $C_1$-$C_3$alkyl;
or a pharmaceutically acceptable salt or a solvate thereof.

In one aspect, the invention relates to compounds of Formula (I)

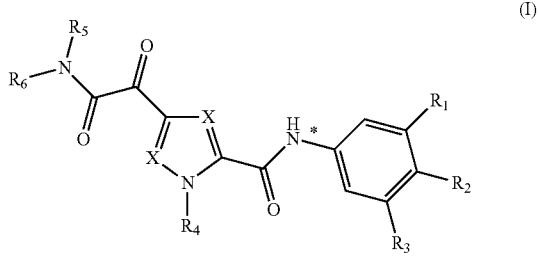
(I)

or a stereoisomer or tautomeric form thereof, wherein:
Each X independently represents $CR^7$;
$R^2$ is Hydrogen or Fluoro;
$R^1$ and $R^3$ are independently selected from the group consisting of Hydrogen, Fluoro, Chloro, Bromo, —$CHF_2$, —$CH_2F$, —$CF_3$, —CN and methyl;
$R^4$ is Hydrogen or methyl;
$R^5$ is Hydrogen;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_1$-$C_3$alkyl, —CN, —C(=O)—$OR^8$ or —C(=O)—$N(R^8)_2$;
$R^7$ represents hydrogen or methyl;
$R^8$ represents hydrogen or $C_1$-$C_3$alkyl;
or a pharmaceutically acceptable salt or a solvate thereof.

In a further aspect, the invention provides compounds of Formula (Ia) or (Ib)

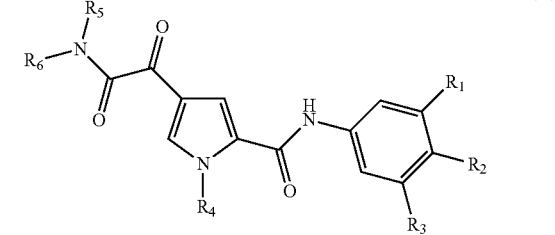
(Ia)

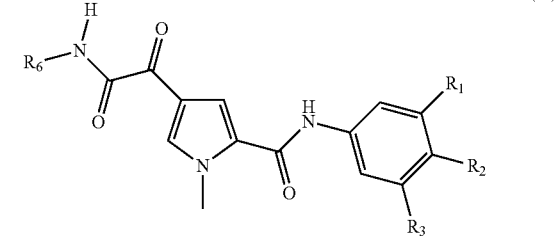
(Ib)

or a stereoisomer or tautomeric form thereof, wherein:
Each X independently represents $CR^7$;
$R^2$ is Hydrogen or Fluoro;
$R^1$ and $R^3$ are independently selected from the group consisting of Hydrogen, Fluoro, Chloro, Bromo, —$CHF_2$, —$CH_2F$, —$CF_3$, —CN and methyl;
$R^4$ is Hydrogen or methyl;
$R^5$ is Hydrogen;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_1$-$C_3$alkyl, —CN, —C(=O)—OR$^8$ or —C(=O)—N(R$^8$)$_2$;

$R^7$ represents hydrogen or methyl;

$R^8$ represents hydrogen or $C_1$-$C_3$alkyl;

or a pharmaceutically acceptable salts or a solvate thereof.

In a first embodiment, compounds of Formula (IA, (I), (Ia) and (Ib) are disclosed wherein 1e is selected from either hydrogen, Fluoro, Chloro, —CHF$_2$, —CN, —CF$_3$ or methyl. In another embodiment, $R^1$ is selected from either hydrogen, Fluoro, Chloro, CHF$_2$, —CN, —CF$_3$ or methyl and at least one of $R^1$ and $R^3$ is Fluoro or hydrogen. In yet a further embodiment, at least one of $R^1$ and $R^3$ is Fluoro, and the other $R^1$ or $R^3$ is selected from hydrogen, Fluoro, Chloro, —CHF$_2$, —CN, —CF$_3$ or methyl.

In yet another embodiment, compounds of the present invention are disclosed wherein $R^4$ is methyl.

In a further embodiment, compounds of the present invention are disclosed wherein $R^6$ contains a 3-7 membered saturated ring optionally containing one oxygen, such 3-7 membered saturated ring optionally substituted with methyl. In a further embodiment, $R^6$ is a 4 or 5 membered saturated ring containing one oxygen, such 4 or 5 membered saturated ring optionally substituted with methyl.

In another embodiment, $R^6$ is a branched $C_1$-$C_6$alkyl, optionally substituted with one or more substituents selected from the group consisting of Fluoro, —CN, —C(=O)—OR$^8$ or —C(=O)—N(R$^8$)$_2$. In a further embodiment, $R^6$ is a branched $C_1$-$C_6$alkyl.

Another embodiment of the present invention relates to those compounds of Formula (IA) or any subgroup thereof as mentioned in any of the other embodiments wherein one or more of the following restrictions apply:

(a) $R^4$ is methyl and $R^6$ is selected from the group consisting of $C_1$-$C_6$alkyl optionally being substituted with one or more Fluoro;

(b) $R^2$ is Hydrogen or Fluoro.

(c) $R^1$ and $R^3$ are independently selected from the group consisting of Hydrogen, Fluoro, Chloro —CN and methyl.

(d) At least one $R^7$ is Chloro or methyl.

(e) $R^2$ is Hydrogen or Fluoro and $R^1$ and $R^3$ are independently selected from the group consisting of Hydrogen, Fluoro, Chloro and —CN.

(f) $R^6$ contains a 3-7 membered saturated ring optionally containing one oxygen, more specifically $R^6$ is a 4 or 5 membered saturated ring optionally containing one oxygen, such 4 or 5 membered saturated ring optionally substituted with one or more substituents selected from $C_1$-$C_3$alkyl optionally substituted with one or more Fluoro or Fluoro.

(g) $R^6$ comprises a branched $C_3$-$C_6$alkyl optionally substituted with one or more Fluoro, or wherein $R^6$ comprises a $C_3$-$C_6$cycloalkyl wherein such $C_3$-$C_6$cycloalkyl is substituted with one or more Fluoro or substituted with $C_1$-$C_4$alkyl substituted with one or more Fluoro, or wherein $R^6$ comprises a $C_3$-$C_6$cycloalkyl optionally substituted with one or more Fluoro and/or substituted with $C_1$-$C_3$alkyl optionally substituted with one or more Fluoro.

(h) $R^4$ is methyl; $R^6$ is selected from the group consisting of $C_1$-$C_6$alkyl optionally being substituted with one or more Fluoro and $R^2$ is Fluoro.

Further combinations of any of the embodiments are also envisioned to be in the scope of the present invention.

Preferred compounds according to the invention are compound or a stereoisomer or tautomeric form thereof with a Formula (IA), (I), (Ia), (Ib), as represented in the synthesis of compounds section and of which the activity is displayed in Table 1.

In a further aspect, the present invention concerns a pharmaceutical composition comprising a therapeutically or prophylactically effective amount of a compound of Formula (IA) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (IA), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (IA) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (IA) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (IA).

The compounds of Formula (IA), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of Formula (IA) or any subgroup thereof, as specified herein with other anti-HBV agents. The term "combination" may relate to a product or kit containing (a) a compound of Formula (IA), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of Formula (IA) or any subgroup thereof with at least one anti-HBV agent. In a particular embodiment, the invention concerns combination of a compound of Formula (IA) or any subgroup thereof with at least two anti-HBV agents. In a particular embodiment, the invention concerns combination of a compound of Formula (IA) or any subgroup thereof with at least three anti-HBV agents. In a particular embodiment, the invention concerns combination of a compound of Formula (IA) or any subgroup thereof with at least four anti-HBV agents.

The term anti-HBV agent also includes compounds capable of treating HBV infection via immunomodulation. Examples of immunomodulators are interferon-α (IFN-α), pegylated interferon-α or stimulants of the innate immune system such as Toll-like receptor 7 and/or 8 agonists. One embodiment of the present invention relates to combinations of a compound of Formula (IA) or any subgroup thereof, as specified herein with an immunomodulating compound, more specifically a Toll-like receptor 7 and/or 8 agonist.

The combination of previously known anti-HBV agents, such as interferon-α (IFN-α), pegylated interferon-α, 3TC, adefovir or a combination thereof, and, a compound of Formula (IA) or any subgroup thereof can be used as a medicine in a combination therapy.

Generic Synthesis

The substituents represented by $R^{1,2,3}$, $R^6$ or $R^7$ in this general synthesis section are meant to include any substituent or reactive species that is suitable for transformation into any $R^{1,2,3}$, $R^6$ or $R^7$ substituent according to the present invention without undue burden for the person skilled in the art.

Scheme 1

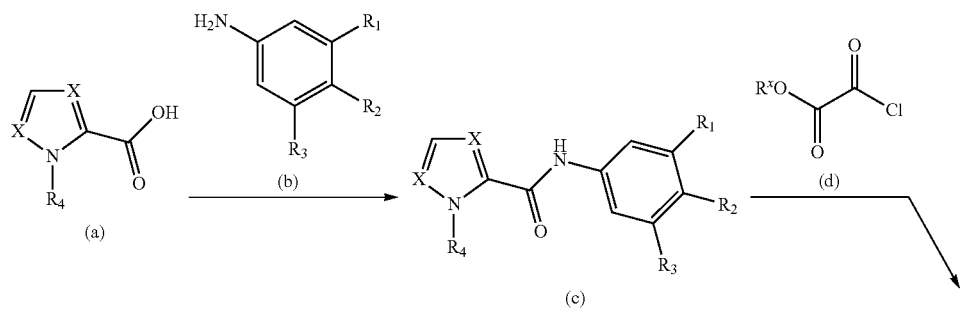

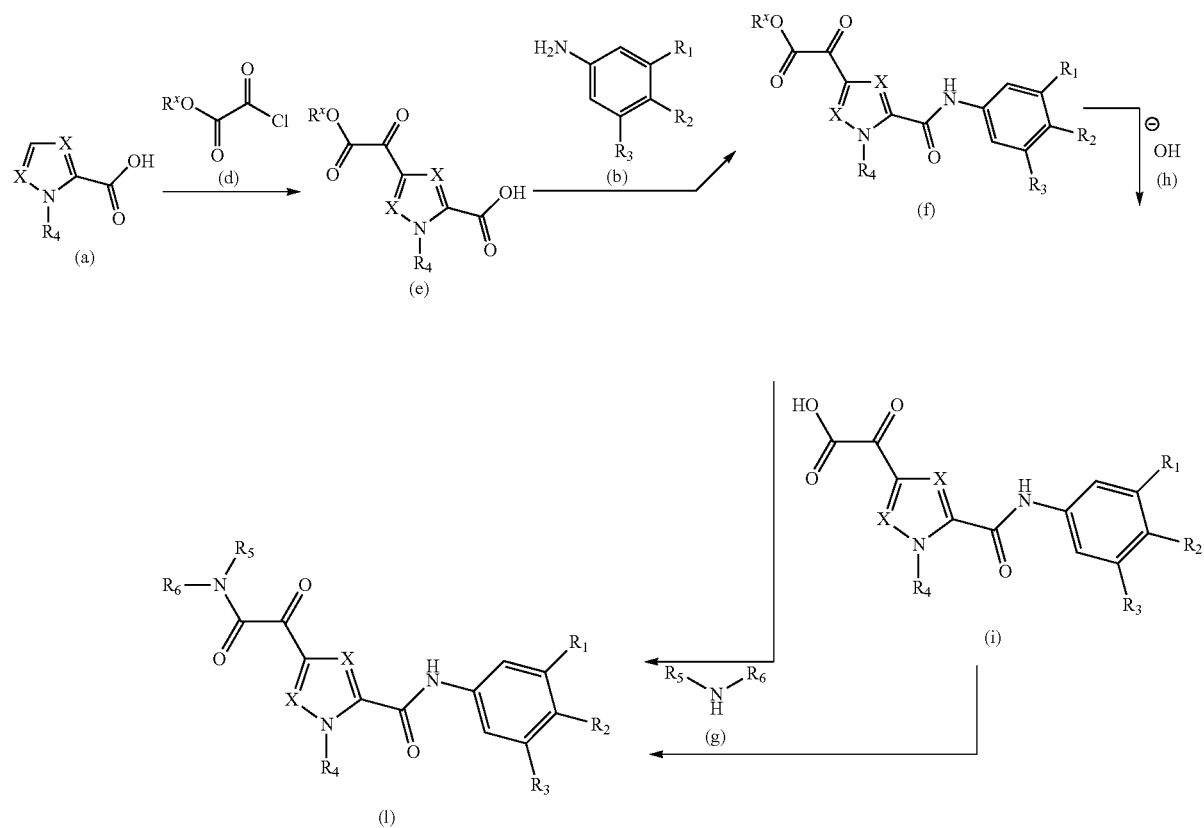
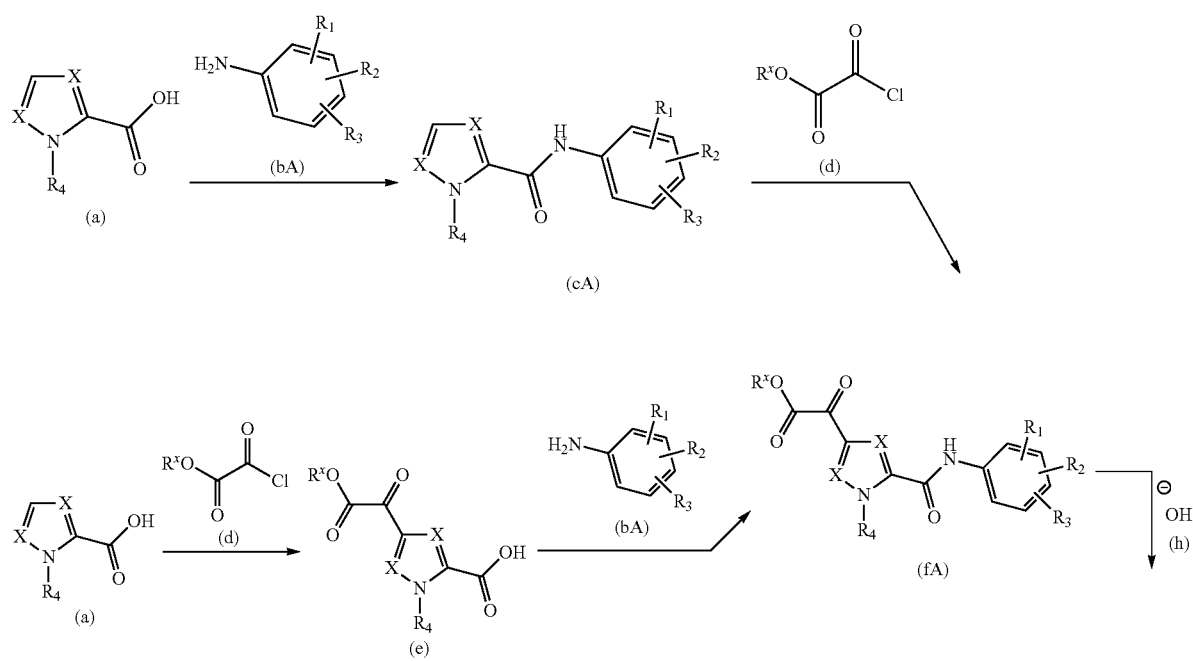
Scheme 1A

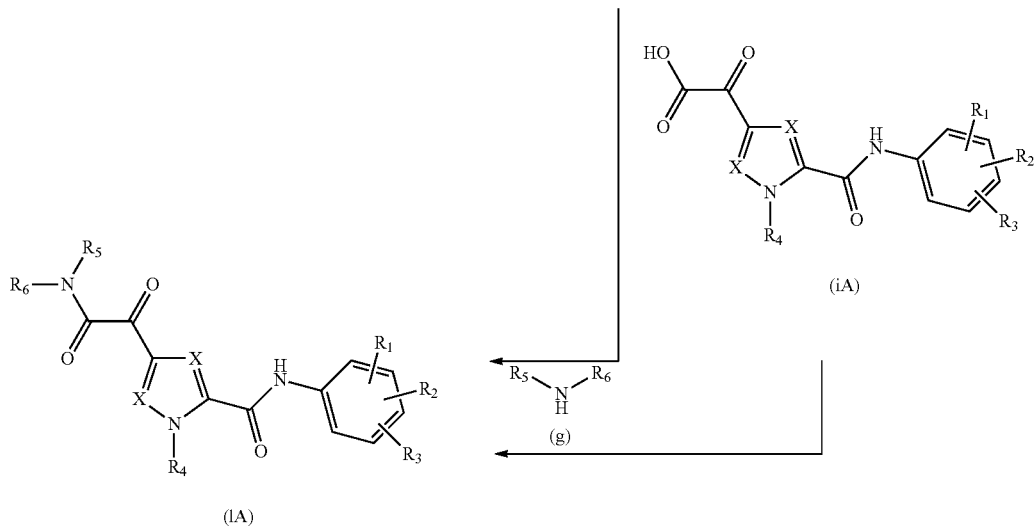

The synthesis of compounds of general Formula (I) can be performed as outlined in Scheme 1. Each $R^x$ independently represents lower alkyl, preferably $C_1$-$C_3$alkyl and even more preferred methyl or ethyl. A carboxylic acid of general formula (a) can be coupled with an aniline of general formula (b) using a peptide coupling reagent like for example HATU in the presence of an organic amine base such as TEA or DIPEA. The resulting compound of general formula (c) can be reacted with an oxalyl chloride mono-alkyl ester of general formula (d) in the presence of a Lewis acid like for example $AlCl_3$ to provide a compound of general formula (f). Alternatively, compounds of general formula (f) can be obtained by inversion of the order of the aforementioned reaction steps, in particular by reaction of a carboxylic acid of general formula (a) with oxalyl chloride monoalkyl ester of general formula (d) in the presence of a Lewis acid like for example $AlCl_3$ to provide a compound of general formula (e), followed by coupling of (e) with an aniline of general formula (b) using a peptide coupling reagent like for example HATU in the presence of a organic amine base such as TEA or DIPEA. Reaction of a compound of general formula (f) with an amine of general formula (g) in a suitable solvent such as for example EtOH, provides a compound of general formula (I). Alternatively, compounds of general formula (I) can be obtained from a compound of general formula (f) in a two-step procedures that involves hydrolysis of the ester moiety of a compound of general formula (f) with an inorganic base of general formula (h) like for example NaOH, followed by coupling of the resulting alpha-keto-acid of general formula (i) with an amine of general formula (g) using a peptide coupling reagent like for example HATU in the presence of a organic amine base such as TEA or DIPEA. Similarly as described for the synthesis of compounds of general Formula (I) in Scheme 1, the synthesis of compounds of general formula IA is described in Scheme 1A.

Scheme 2

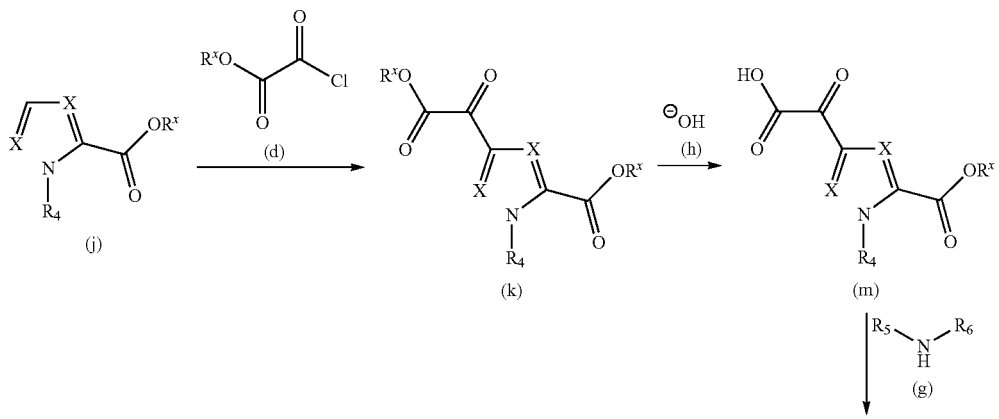

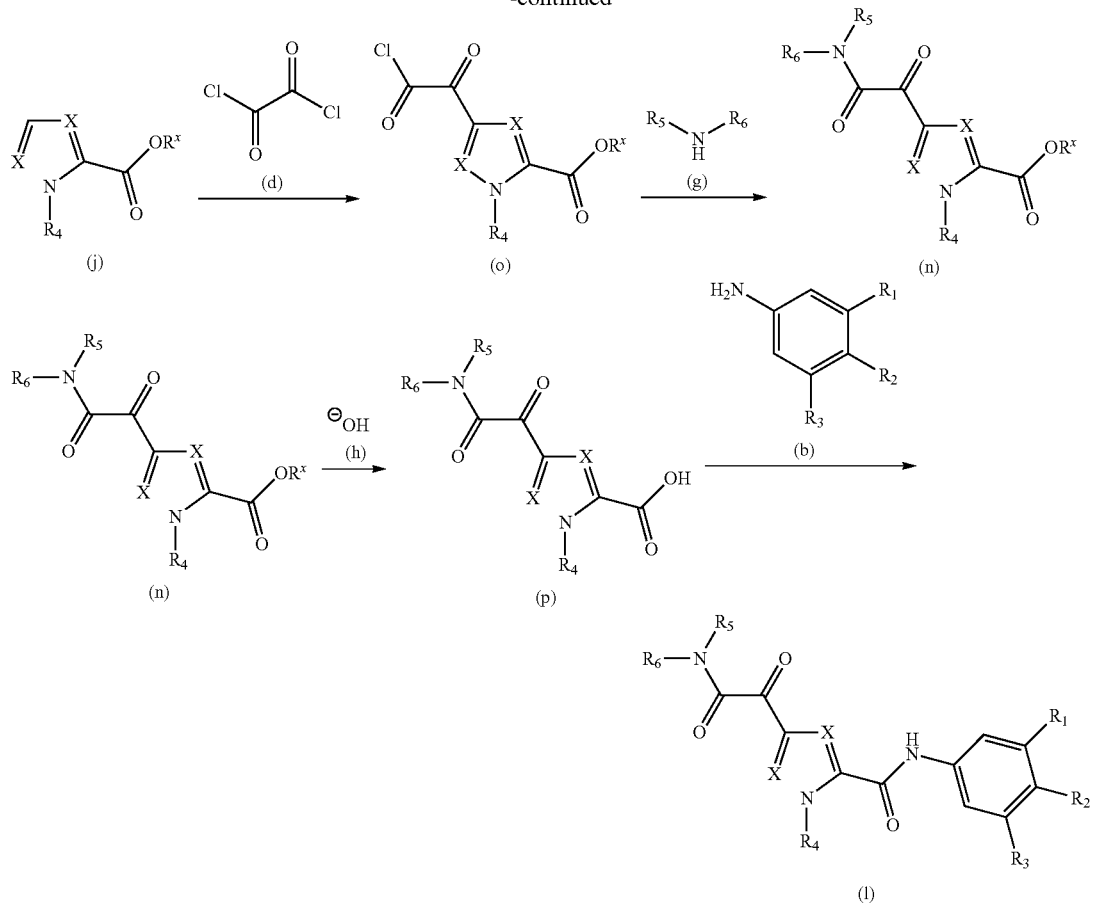

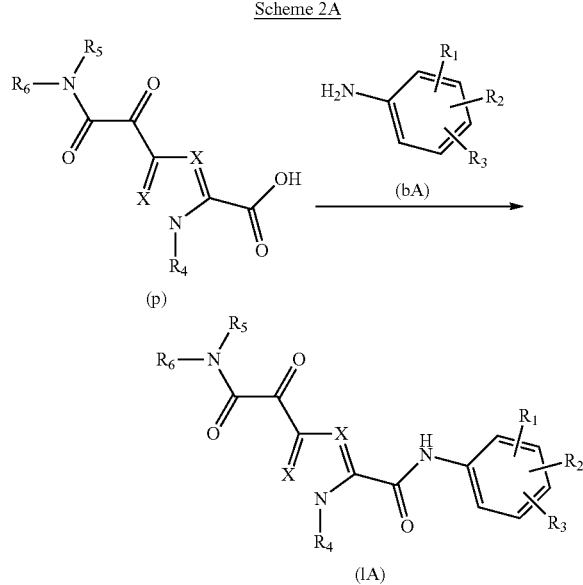

The synthesis of compounds of general formula (I) can also be performed as outlined in Scheme 2. Each $R^x$ independently represents lower alkyl, preferably $C_1$-$C_3$alkyl and even more preferred methyl or ethyl. A carboxylic ester of general formula (j) can be reacted with an oxalyl chloride monoalkyl ester of general formula (d) in the presence of a Lewis acid like for example $AlCl_3$ to provide a compound of general formula (k). Hydrolysis of (k) with an inorganic base of general formula (h) like NaOH provides the corresponding alpha-keto-acid of general formula (m). Compounds of general formula (n) can be obtained by coupling of (m) with an amine of general formula (g) using a peptide coupling reagent like for example HATU in the presence of a organic amine base such as TEA or DIPEA. Alternatively, compounds of general formula (n) can be obtained from carboxylic ester of general formula (j) in a two-step one-pot procedure that includes reaction of (j) with oxalyl chloride, followed by treatment of the intermediate of general formula (o) with an amine of general formula (g). A compound of general formula (n) can be hydrolysed with an inorganic base of general formula (h) like for example NaOH. The resulting carboxylic acid of general formula (p) can be coupled with an aniline of general formula (b) using a peptide coupling reagent like for example HATU in the presence of a organic amine base such as TEA or DIPEA, to provide compounds of general formula (I). Similarly as described for the synthesis of compounds of general Formula (I) from a compound of general formula (p) and aniline (b) shown in Scheme 2, the synthesis of compounds of general formula IA can be performed from aniline (bA) and a compound of general formula (p) as described in Scheme 2A.

Alternatively, intermediates of the general formula (cA) and compounds of the general formula (IA) can be synthesized as depicted in scheme 3A. In this case a compound of general formula (j) or (n) is reacted with an aniline of general formula (bA) under influence of a base like lithium bis(trimethylsilyl)amide (LiHMDS), resulting in compound of general formula (cA) and (IA) respectively.

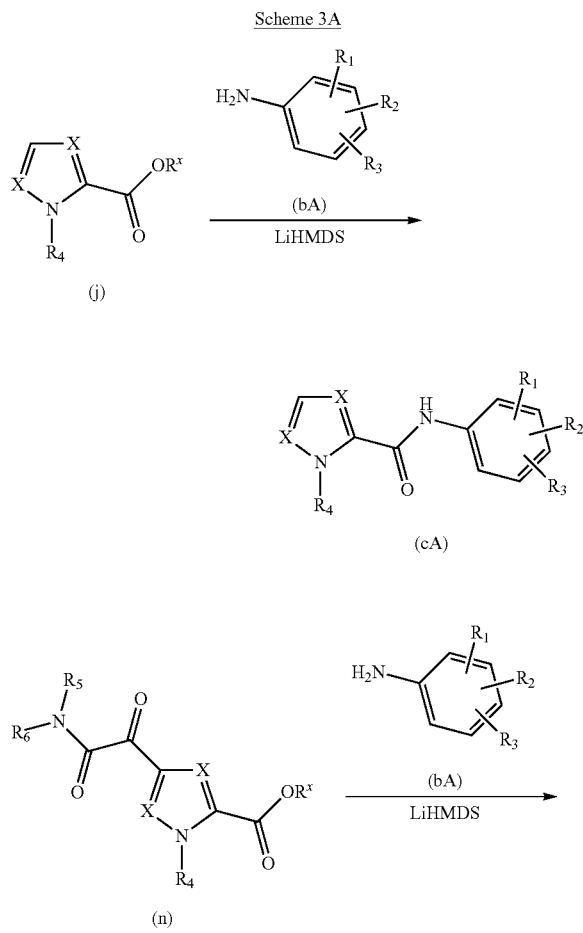

Scheme 3A

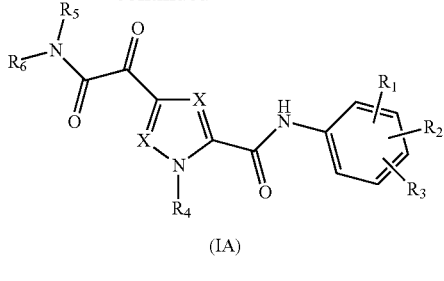

(IA)

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to 1the $[M+H]^+$ (protonated molecule) and/or EM-Elf (deprotonated molecule). In case the compound was not directly ionizable the type of adduct is specified (i.e. $[M+NH_4]^+$, $[M+HCOO]^-$, etc. . . . ). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector.

LCMS Methods (Flow expressed in mL/min; column temperature (T) in ° C.; Run time in minutes).

| Method code | Instrument | Column | Mobile phase | Gradient | Flow Col T | Run time |
|---|---|---|---|---|---|---|
| A | Waters: Acquity® UPLC® - DAD and SQD | Waters: HSS T3 (1.8 µm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.8 55 | 3.5 |
| B | Waters: Acquity ® UPLC ® - DAD and SQD | Waters: BEH C18 (1.7 µm, 2.1*50 mm) | A: 10 mM $CH_3COONH_4$ in 95% $H_2O$ - 5% $CH_3CN$ B: $CH_3CN$ | From 95% A to 5% A in 1.3 min, held for 0.7 min. | 0.8 55 | 2 |
| C | Waters: Acquity® UPLC® - DAD and SQD | Waters: HSS T3 (1.8 µm, 2.1*100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 55 | 3.5 |
| D | Waters: Alliance®- DAD - ZQ and | Waters: Xterra MS C18 (3.5 µm, | A: 25 mM $CH_3COONH_4$ in 95% H2O + 5% $CH_3CN$ | From 100% A to 1%, A, 49% B and 50% C in | 1.6 40 | 11 |

| Method code | Instrument | Column | Mobile phase | Gradient | Flow Col T | Run time |
|---|---|---|---|---|---|---|
| | ELSD 2000 Alltech | 4.6*100 mm) | B: CH3CN C: CH3OH D: (40% CH3CN and 40% CH3OH and 20% H2O with 0.25% CH3COOH | 6.5 min, to 1% A and 99% B in 0.5 min, to 100% D in 1 min held for 1.0 min to 100% A in 0.5 min and held for 1.5 min. | | |

SYNTHESIS OF EXAMPLES

Compound 1: (R)-4-(2-(sec-butylamino)-2-oxoacetyl)-N-(4-fluoro-3-methylphenyl)-1-methyl-1H-pyrrole-2-carboxamide

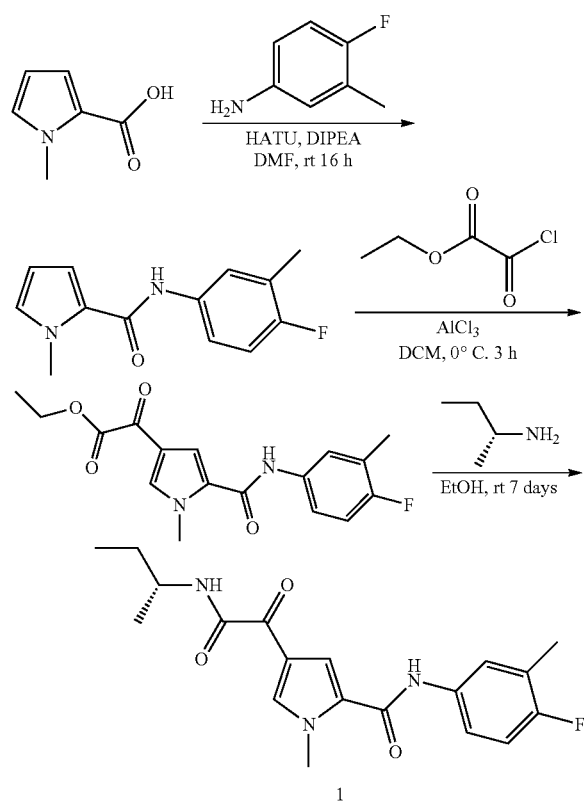

1-Methyl-1H-pyrrole-2-carboxylic acid (2.0 g, 16 mmol), 4-fluoro-3-methylaniline (2.0 g, 16 mmol) and N,N-diisopropylethylamine (DIPEA, 6.2 g, 48 mmol) were dissolved in 30 mL DMF and cooled on ice under $N_2$. 2-(7-Aza-1H-benzotriazole-1-yl)-1,1,3,3-tetramethyl-uronium hexafluorophosphate (HATU, 6.69 g, 17.6 mmol) was added, the ice bath was removed and the mixture was stirred overnight at room temperature. The reaction mixture was diluted with 200 mL EtOAc and washed with 1N HCl, NaHCO3 solution and brine. The organic layer was dried over $Na_2SO_4$, filtered, and concentrated under reduced pressure. The residue was crystallized from a mixture of 30 mL MeOH and 15 mL water. The crystals were filtered off and dried in vacuum to provide N-(4-fluoro-3-methylphenyl)-1-methyl-1H-pyrrole-2-carboxamide (3.22 g) as gray needles, mp=111.3° C. LC method B; Rt: 0.99 min. m/z: 233.2 $(M+H)^+$ Exact mass: 232.1. $^1$H NMR (400 MHz, DMSO-$d_6$) δ ppm 2.22 (s, 3 H), 3.87 (s, 3 H), 6.08 (dd, J=4.0, 2.6 Hz, 1 H), 6.95-7.03 (m, 2 H), 7.07 (t, J=9.1 Hz, 1 H), 7.44-7.54 (m, 1 H), 7.62 (dd, J=7.3, 2.4 Hz, 1 H), 9.69 (s, 1 H).

N-(4-Fluoro-3-methylphenyl)-1-methyl-1H-pyrrole-2-carboxamide (2.0 g, 8.6 mmol) was dissolved in 30 mL dichloromethane and cooled on ice under $N_2$. A solution of ethyl chlorooxoacetate (2.94 g, 21.5 mmol) in 5 ml dichloromethane was added drop wise and the mixture was stirred for 30 min at 0° C. Aluminium(III) chloride (3.44 g, 25.8 mmol) was added in portions and the reaction mixture was stirred at 0° C. for 3 hours. The reaction mixture was poured into 100 ml vigorously stirred ice water and extracted with EtOAc (2×). The combined organic layers were washed with NaHCO3 solution and brine, dried over $Na_2SO_4$, filtered, and concentrated under reduced pressure. The residue was crystallized from 40 ml EtOH, the crystals were filtered off and dried in vacuum to provide ethyl 2-(5-(4-fluoro-3-methylphenylcarbamoyl)-1-methyl-1H-pyrrol-3-yl)-2-oxoacetate (1.29 g) as a white solid, mp=126.3° C. LC method B; Rt: 1.04 min. m/z: 333.1 $(M+H)^+$ Exact mass: 332.1. $^1$H NMR (400 MHz, DMSO-$d_6$) δ ppm 1.33 (t, J=7.2 Hz, 3 H), 2.23 (d, J=1.8 Hz, 3 H), 3.95 (s, 3 H), 4.35 (q, J=7.0 Hz, 2 H), 7.10 (t, J=9.2 Hz, 1 H), 7.48-7.55 (m, 1 H), 7.58 (d, J=1.8 Hz, 1 H), 7.65 (dd, J=7.0, 2.4 Hz, 1 H), 8.01 (d, J=1.5 Hz, 1 H), 10.07 (s, 1 H).

Ethyl 2-(5-(4-fluoro-3-methylphenylcarbamoyl)-1-methyl-1H-pyrrol-3-yl)-2-oxoacetate (300 mg, 0.9 mmol) and (R)-(−)-2-aminobutane (196 mg, 2.7 mmol) were mixed in 5 ml EtOH and stirred at room temperature in a closed vessel for 7 days. The reaction mixture was concentrated under reduced pressure and then purified by preparative HPLC (stationary phase: RP Vydac Denali C18—10 μm, 200 g, 5 cm), mobile phase: 0.25% NH4HCO3 solution in water, CH3CN). The product fractions were concentrated, dissolved in MeOH and concentrated again yielding (R)-4-(2-(sec-butylamino)-2-oxoacetyl)-N-(4-fluoro-3-methylphenyl)-1-methyl-1H-pyrrole-2-carboxamide (Compound 1, 238 mg), as a white powder, mp=136.5° C. LC method B; Rt: 1.07 min. m/z: 358.1 $(M-H)^-$ Exact mass: 359.1. $^1$H NMR (400 MHz, DMSO-$d_6$) δ ppm 0.84 (t, J=7.4 Hz, 3 H), 1.12 (d, J=6.6 Hz, 3 H), 1.39-1.61 (m, 2 H), 2.23 (d, J=1.5 Hz, 3 H), 3.72-3.88 (m, 1 H), 3.95 (s, 3 H), 7.09 (t, J=9.2 Hz, 1 H), 7.47-7.58 (m, 1 H), 7.64 (d, J=1.8 Hz, 1 H), 7.66 (dd, J=7.2, 2.5 Hz, 1 H), 8.13 (s, 1 H), 8.38-8.53 (m, 1 H), 10.04 (s, 1 H).

Compound 2: N-(4-fluoro-3-methylphenyl)-4-(2-(isopropylamino)-2-oxoacetyl)-1-methyl-1H-pyrrole-2-carboxamide

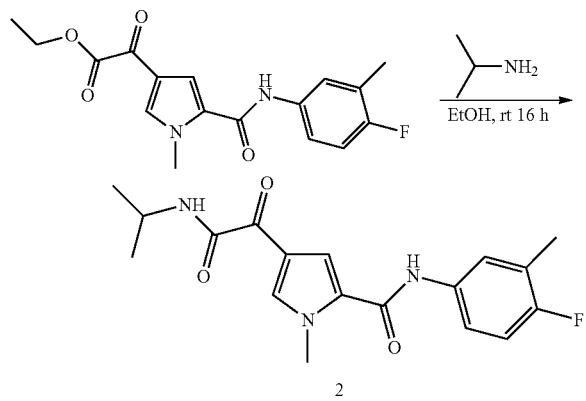

Compound 2 was prepared similarly as Compound 1 by reaction of ethyl 2-(5-(4-fluoro-3-methylphenylcarbamoyl)-1-methyl-1H-pyrrol-3-yl)-2-oxoacetate with 10 equivalents of isopropylamine by overnight stirring at room temperature in EtOH in a closed vessel. The reaction mixture was concentrated under reduced pressure and then purified by preparative HPLC (stationary phase: RP Vydac Denali C18—10 μm, 200 g, 5 cm), mobile phase: 0.25% NH$_4$HCO$_3$ solution in water, CH$_3$CN). The product fractions were concentrated, dissolved in MeOH and concentrated again yielding N-(4-fluoro-3-methylphenyl)-4-(2-(isopropylamino)-2-oxoacetyl)-1-methyl-1H-pyrrole-2-carboxamide (Compound 2, 229 mg), as a foam. LC method A; Rt: 1.84 min. m/z: 344.1 (M–H)$^-$ Exact mass: 345.2. $^1$H NMR (400 MHz, DMSO-d$_6$) δ ppm 1.15 (d, J=6.6 Hz, 6 H), 2.23 (d, J=1.8 Hz, 3 H), 3.95 (s, 3 H), 3.96-4.07 (m, 1 H), 7.09 (t, J=9.2 Hz, 1 H), 7.49-7.57 (m, 1 H), 7.63 (d, J=1.8 Hz, 1 H), 7.66 (dd, J=7.2, 2.5 Hz, 1 H), 8.14 (d, J=1.5 Hz, 1 H), 8.52 (d, J=8.1 Hz, 1 H), 10.04 (s, 1 H).

Compound 3: 4-(2-(tert-butylamino)-2-oxoacetyl)-N-(4-fluoro-3-methylphenyl)-1-methyl-1H-pyrrole-2-carboxamide

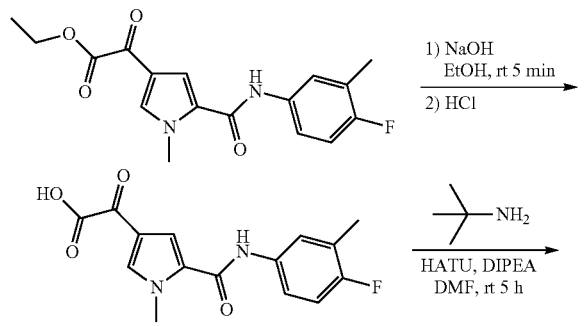

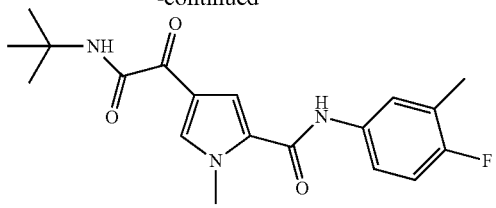

Ethyl 2-(5-(4-fluoro-3-methylphenylcarbamoyl)-1-methyl-1H-pyrrol-3-yl)-2-oxoacetate (980 mg, 2.9 mmol) was dissolved in 20 ml EtOH. A 1N aqueous solution of NaOH (8.8 mL, 8.8 mmol) was added drop wise. The reaction mixture was stirred for 5 min at room temperature and was then cooled on ice. 1N HCl was added until pH=2. The reaction mixture was diluted by the addition of water (50 mL) causing the formation of a white precipitate. The solid material was filtered off, rinsed with water, and dried in vacuum to provide 2-(5-(4-fluoro-3-methylphenylcarbamoyl)-1-methyl-1H-pyrrol-3-yl)-2-oxoacetic acid (530 mg) as white crystals, mp=180.8° C. LC method B; Rt: 0.61 min. m/z: 303.1 (M–H)$^-$ Exact mass: 304.1. $^1$H NMR (400 MHz, DMSO-d$_6$) δ ppm 2.23 (d, J=1.8 Hz, 3 H), 3.95 (s, 3 H), 7.09 (t, J=9.2 Hz, 1 H), 7.49-7.55 (m, 1 H), 7.57 (d, J=1.8 Hz, 1 H), 7.65 (dd, J=7.0, 2.4 Hz, 1 H), 7.97 (d, J=1.5 Hz, 1 H), 10.06 (s, 1 H), 14.05 (br. s., 1 H).

2-(5-(4-Fluoro-3-methylphenylcarbamoyl)-1-methyl-1H-pyrrol-3-yl)-2-oxoacetic acid (530 mg, 1.74 mmol)), tert-butylamine (127 mg, 1.74 mmol), and N,N-diisopropylethylamine (DIPEA, 675 mg, 5.2 mmol) were dissolved in 10 mL DMF and cooled on ice under N$_2$. 2-(7-Aza-1H-benzotriazole-1-yl)-1,1,3,3-tetramethyluronium hexafluorophosphate (HATU, 728 mg, 1.92 mmol) was added, the ice bath was removed and the mixture was stirred at room temperature for 5 hours. The reaction mixture was diluted with EtOAc (100 mL) and washed with 1N HCl, NaHCO$_3$ solution, and brine. The organic layer was dried over Na$_2$SO$_4$, filtered and concentrated under reduced pressure. The residue was crystallized from a mixture of 10 mL MeOH and 5 mL water. The crystals were filtered off and dried in vacuum to provide 4-(2-(tert-butylamino)-2-oxoacetyl)-N-(4-fluoro-3-methyl-phenyl)-1-methyl-1H-pyrrole-2-carboxamide (Compound 3, 517 mg) as a white powder. LC method B; Rt: 1.12 min. m/z: 358.2 (M–H)$^-$ Exact mass: 359.2. $^1$H NMR (400 MHz, DMSO-d$_6$) δ ppm 1.36 (s, 9 H), 2.23 (d, J=1.8 Hz, 3 H), 3.95 (s, 3 H), 7.09 (t, J=9.2 Hz, 1 H), 7.50-7.56 (m, 1 H), 7.61 (d, J=1.8 Hz, 1 H), 7.66 (dd, J=7.0, 2.2 Hz, 1 H), 7.95 (s, 1 H), 8.10 (d, J=1.5 Hz, 1 H), 10.05 (s, 1 H).

Compound 4: N-(4-fluoro-3-methylphenyl)-1-methyl-4-(2-(3-methyloxetan-3-ylamino)-2-oxoacetyl)-1H-pyrrole-2-carboxamide

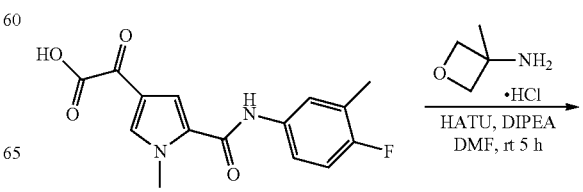

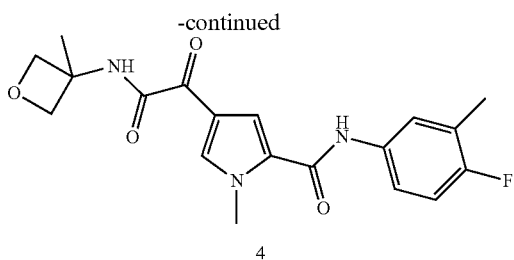

4

2-(5-(4-Fluoro-3-methylphenylcarbamoyl)-1-methyl-1H-pyrrol-3-yl)-2-oxoacetic acid (410 mg, 1.35 mmol), 3-methyl-3-oxetanamine hydrochloride (183 mg, 1.48 mmol), and N,N-diisopropylethylamine (DIPEA, 870 mg, 6.74 mmol) were dissolved in 10 mL of DMF and cooled on ice under $N_2$. 2-(7-Aza-1H-benzotriazole-1-yl)-1,1,3,3-tetramethyluronium hexafluorophosphate (HATU, 563 mg, 1.48 mmol) was added, the ice bath was removed and the mixture was stirred at room temperature for 5 hours. The reaction mixture was diluted with 100 mL EtOAc and washed with 1N HCl, NaHCO$_3$ solution, and brine. The organic layer was evaporated under reduced pressure. The residue was purified by Preparative HPLC (stationary phase: Uptisphere C18 ODB—10 µm, 200 g, 5 cm), mobile phase: 0.25% NH$_4$HCO$_3$ solution in water, MeOH). The product fractions were concentrated, dissolved in MeOH, and concentrated again. The residue was crystallized from a mixture of 10 mL MeOH and 5 mL water. The crystals were filtered off and dried in vacuum to provide N-(4-fluoro-3-methylphenyl)-1-methyl-4-(2-(3-methyloxetan-3-yl-amino)-2-oxoacetyl)-1H-pyrrole-2-carboxamide (Compound 4, 183 mg) as a white powder, mp=145.1° C. LC method A; Rt: 1.63 min. m/z: 372.0 (M–H)$^-$ Exact mass: 373.1. $^1$H NMR (400 MHz, DMSO-d$_6$) δ ppm 1.58 (s, 3 H), 2.23 (d, J=1.8 Hz, 3 H), 3.95 (s, 3 H), 4.35 (d, J=6.8 Hz, 2 H), 4.72 (d, J=6.4 Hz, 2 H), 7.09 (t, J=9.2 Hz, 1 H), 7.48-7.58 (m, 1 H), 7.65 (d, J=1.8 Hz, 1 H), 7.67 (d, J=2.4 Hz, 1 H), 8.17 (d, J=1.3 Hz, 1 H), 9.26 (s, 1 H), 10.05 (s, 1 H).

Compound 5: (R)—N-(4-fluoro-3-methylphenyl)-1-methyl-4-(2-oxo-2-(1,1,1-trifluoropropan-2-ylamino)acetyl)-1H-pyrrole-2-carboxamide

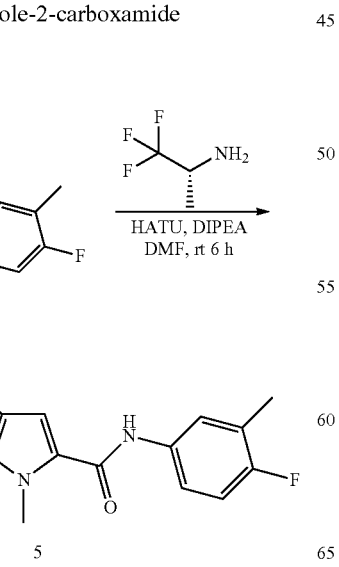

2-(5-(4-Fluoro-3-methylphenylcarbamoyl)-1-methyl-1H-pyrrol-3-yl)-2-oxoacetic acid (300 mg, 0.95 mmol), (R)-1,1,1-trifluoro-2-propylamine (118 mg, 1.04 mmol), and N,N-diisopropylethylamine (DIPEA, 367 mg, 2.84 mmol) were dissolved in 5 mL DMF under $N_2$. 2-(7-Aza-1H-benzotriazole-1-yl)-1,1,3,3-tetramethyluronium hexafluoro-phosphate (HATU, 396 mg, 1.04 mmol) was added and the mixture was stirred at room temperature for 6 hours. The reaction mixture was diluted with 100 mL EtOAc and washed with 1N HCl, NaHCO$_3$ solution and brine. The organic layer was evaporated under reduced pressure. The residue was crystallized from a mixture of 10 mL MeOH and 5 mL water. The crystals were filtered off and dried in vacuum to provide (R)—N-(4-fluoro-3-methylphenyl)-1-methyl-4-(2-oxo-2-(1,1,1-trifluoropropan-2-ylamino)acetyl)-1H-pyrrole-2-carboxamide (Compound 5, 182 mg) as a white powder, mp=156.9° C. LC method B; Rt: 1.10 min. m/z: 398.2 (M–H)$^-$ Exact mass: 399.1. $^1$H NMR (400 MHz, DMSO-d$_6$) δ ppm 1.35 (d, J=7.0 Hz, 3 H), 2.23 (d, J=1.8 Hz, 3 H), 3.95 (s, 3 H), 4.59-4.79 (m, 1 H), 7.09 (t, J=9.1 Hz, 1 H), 7.45-7.58 (m, 1 H), 7.60-7.71 (m, 2 H), 8.10 (d, J=1.3 Hz, 1 H), 9.32 (d, J=9.0 Hz, 1 H), 10.07 (s, 1 H).

Compound 6: (S)—N-(4-fluoro-3-methylphenyl)-1-methyl-4-(2-oxo-2-(tetrahydrofuran-3-ylamino)acetyl)-1H-pyrrole-2-carboxamide

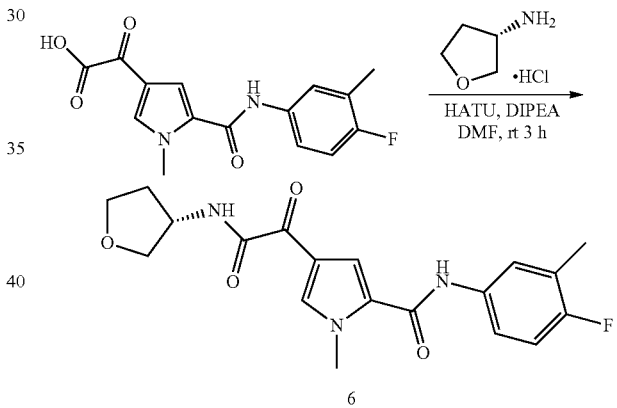

2-(5-(4-Fluoro-3-methylphenylcarbamoyl)-1-methyl-1H-pyrrol-3-yl)-2-oxoacetic acid (300 mg, 0.95 mmol), (S)-tetrahydrofuran-3-amine hydrochloride (128 mg, 1.04 mmol) and N,N-diisopropylethylamine (DIPEA, 611 mg, 4.73 mmol) were dissolved in 5 mL of DMF under $N_2$. 2-(7-Aza-1H-benzotriazole-1-yl)-1,1,3,3-tetramethyluronium hexafluoro-phosphate (HATU, 396 mg, 1.04 mmol) was added and the mixture was stirred at room temperature for 3 hours. The reaction mixture was diluted with 100 mL EtOAc and washed with 1N HCl, NaHCO$_3$ solution, and brine. The organic layer was evaporated under reduced pressure. The residue was crystallized from a mixture of 10 mL MeOH and 5 mL water. The crystals were filtered off and dried in vacuum to provide (S)—N-(4-fluoro-3-methylphenyl)-1-methyl-4-(2-oxo-2-(tetrahydrofuran-3-ylamino)acetyl)-1H-pyrrole-2-carboxamide (Compound 6, 248 mg) as a white powder, mp=155.7° C. LC method B; Rt: 0.90 min. m/z: 372.2 (M–H)$^-$ Exact mass: 373.1. $^1$H NMR (400 MHz, DMSO-d$_6$) δ ppm 1.86-1.99 (m, 1 H), 2.07-2.18 (m, 1 H), 2.23 (d, J=1.8 Hz, 3 H), 3.57 (dd, J=8.9, 4.5 Hz, 1 H), 3.71 (td, J=8.1, 5.7 Hz, 1 H), 3.78-3.87 (m, 2 H), 3.95 (s, 3

H), 4.30-4.42 (m, 1 H), 7.09 (t, J=9.2 Hz, 1 H), 7.49-7.56 (m, 1 H), 7.62 (d, J=1.8 Hz, 1 H), 7.66 (dd, J=7.2, 2.3 Hz, 1 H), 8.11 (d, J=1.3 Hz, 1 H), 8.88 (d, J=6.8 Hz, 1 H), 10.05 (s, 1 H).

Compound 7: methyl 2-(2-(5-(4-fluoro-3-methyl-phenylcarbamoyl)-1-methyl-1H-pyrrol-3-yl)-2-oxoacetamido)-2-methylpropanoate

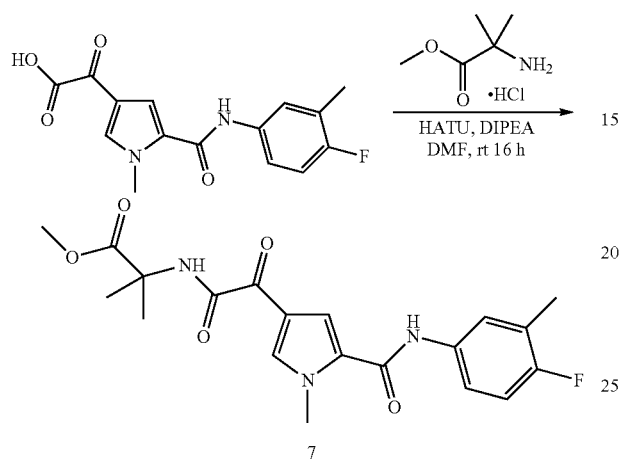

2-(5-(4-Fluoro-3-methylphenylcarbamoyl)-1-methyl-1H-pyrrol-3-yl)-2-oxoacetic acid (800 mg, 2.58 mmol), 2,2-dimethylglycine methylester hydrochloride (435 mg, 2.83 mmol) and N,N-diisopropylethylamine (DIPEA, 1.67 mg, 12.9 mmol) were dissolved in 15 mL of DMF and cooled on ice under $N_2$. 2-(7-Aza-1H-benzotriazole-1-yl)-1,1,3,3-tetramethyl-uronium hexafluorophosphate (HATU, 1078 mg, 2.83 mmol) was added, the ice bath was removed and the mixture was stirred overnight at room temperature. The reaction mixture was diluted with 150 mL EtOAc and washed with 1N HCl, NaHCO₃ solution, and brine. The organic layer was evaporated under reduced pressure. The residue was crystallized from a mixture of 20 mL MeOH and 5 mL water. The crystals were filtered off and dried in vacuum to provide methyl 2-(2-(5-(4-fluoro-3-methylphenylcarbamoyl)-1-methyl-1H-pyrrol-3-yl)-2-oxoacetamido)-2-methylpropanoate (Compound 7, 905 mg) as a white powder, mp=161.0° C. LC method B; Rt: 1.04 min. m/z: 402.2 (M−H)⁻ Exact mass: 403.2. ¹H NMR (400 MHz, DMSO-d₆) δ ppm 1.46 (s, 6 H), 2.23 (d, J=1.8 Hz, 3 H), 3.64 (s, 3 H), 3.95 (s, 3 H), 7.09 (t, J=9.2 Hz, 1 H), 7.49-7.57 (m, 1 H), 7.62 (d, J=1.8 Hz, 1 H), 7.66 (dd, J=7.2, 2.3 Hz, 1 H), 8.07 (d, J=1.3 Hz, 1 H), 8.93 (s, 1 H), 10.07 (s, 1 H).

Compound 8: 4-{[(2-Amino-1,1-dimethyl-2-oxoethyl)amino](oxo)acetyl}-N-(4-fluoro-3-methylphenyl)-1-methyl-1H-pyrrole-2-carboxamide

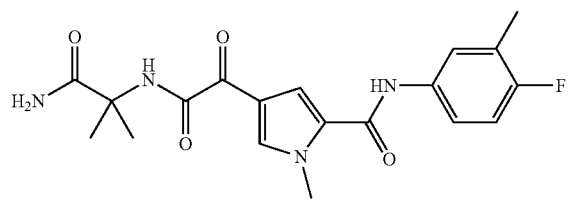 [SMILES: Cc1cc(NC(=O)c2cc(C(=O)C(=O)NC(C)(C)C(N)=O)cn2C)ccc1F]

Compound 8 (300 mg, 0.74 mmol) was dissolved in 7 M NH₃ in MeOH (15 mL) and stirred for 2 days at room temperature. The volatiles were removed under reduced pressure and the residue was dispensed in 7 M NH₃ in MeOH (50 mL) and stirred for 2 days more. The volatiles were removed under reduced pressure and the residue was purified via prep. HPLC followed by trituration with diisopropylether, resulting in compound 8 (96 mg) as an off white powder. LC method B; Rt: 0.86 min. m/z: 387.2 (M−H)⁻ Exact mass: 388.2. Differential scanning calorimetry: From 30 to 300° C. at 10° C./min: Peak: 237.0° C. ¹H NMR (400 MHz, DMSO-d₆) δ ppm 1.52 (s, 6 H), 2.23 (d, J=1.8 Hz, 3 H), 3.95 (s, 3 H), 7.09 (t, J=9.2 Hz, 1 H), 7.17 (br. s., 1 H), 7.43 (br. s., 1 H), 7.50-7.57 (m, 1 H), 7.63-7.70 (m, 2 H), 8.25 (d, J=1.3 Hz, 1 H), 8.55 (s, 1 H), 10.06 (s, 1 H).

Compound 9: 4-[{[(1R)-2-Cyano-1-methylethyl]amino}(oxo)acetyl]-N-(4-fluoro-3-methyl-phenyl)-1-methyl-1H-pyrrole-2-carboxamide

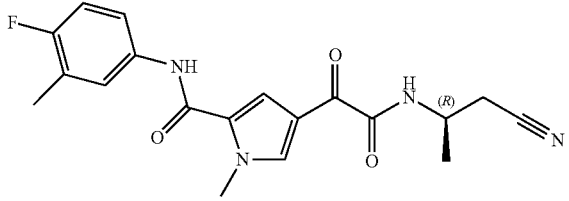

Compound 9 (430 mg) was prepared similarly as described for compound 5 using (3R)-3-aminobutanenitrile instead of (R)-1,1,1-trifluoro-2-propylamine. LC method B; Rt: 0.95 min. m/z: 369.1 (M−H)⁻ Exact mass: 370.1. ¹H NMR (400 MHz, DMSO-d₆) δ ppm 1.23 (d, J=6.6 Hz, 3 H), 2.23 (d, J=1.8 Hz, 3 H), 2.70-2.85 (m, 2 H), 3.95 (s, 3 H), 4.12-4.28 (m, 1 H), 7.09 (t, J=9.2 Hz, 1 H), 7.49-7.57 (m, 1 H), 7.66 (d, J=1.8 Hz, 1 H), 7.67 (d, J=2.2 Hz, 1 H), 8.17 (d, J=1.3 Hz, 1 H), 8.94 (d, J=8.4 Hz, 1 H), 10.06 (s, 1 H). Differential scanning calorimetry: From 30 to 300° C. at 10° C./min: Peak: 138.3° C.

Compound 10: 4-(2-(tert-butylamino)-2-oxoacetyl)-N-(3,4-difluorophenyl)-1-methyl-1H-pyrrole-2-carboxamide

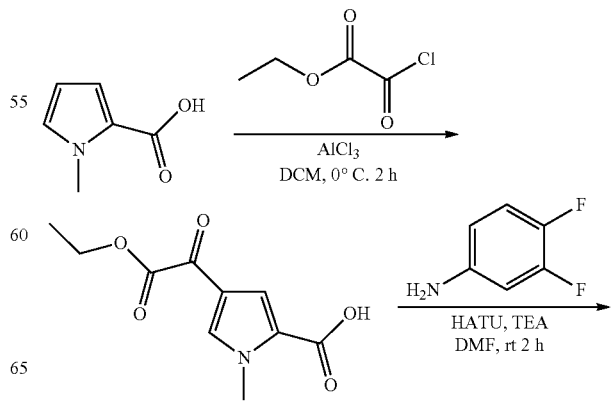

-continued

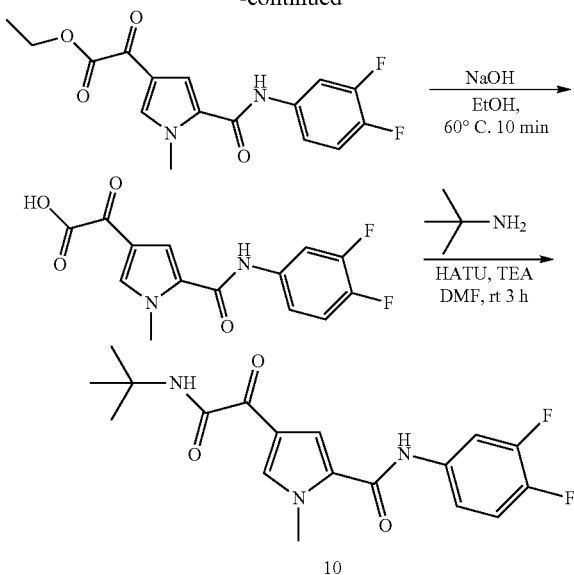

1-Methyl-1H-pyrrole-2-carboxylic acid (2.0 g, 16 mmol) was dissolved in 50 mL dichloromethane and cooled on ice under $N_2$. A solution of ethyl chlorooxoacetate (5.45 g, 40 mmol) in 10 ml dichloromethane was added drop wise and the mixture was stirred for 10 min at 0° C. Aluminium(III) chloride (6.39 g, 48 mmol) was added in portions and the reaction mixture was stirred at 0° C. for 2 hours. The reaction mixture was poured into 200 mL vigorously stirred ice water causing precipitation of a white solid. The precipitate was filtered off and rinsed with water, isopropanol, and diisopropyl ether, and dried in vacuum to afford 4-(2-ethoxy-2-oxoacetyl)-1-methyl-1H-pyrrole-2-carboxylic acid (1.44 g) as a white powder. LC method B; Rt: 0.38 min. m/z: 224.0 (M−H)⁻ Exact mass: 225.1. $^1$H NMR (400 MHz, DMSO-$d_6$) δ ppm 1.31 (t, J=7.0 Hz, 3 H), 3.92 (s, 3 H), 4.33 (q, J=7.1 Hz, 2 H), 7.25 (d, J=1.5 Hz, 1 H), 8.01 (s, 1 H), 12.86 (br. s., 1 H).

To a solution of 4-(2-ethoxy-2-oxoacetyl)-1-methyl-1H-pyrrole-2-carboxylic acid (750 mg, 3.30 mmol) and triethylamine (917 μL, 6.59 mmol) in DMF (7.5 mL), 2-(7-aza-1H-benzotriazole-1-yl)-1,1,3,3-tetramethyluronium hexafluorophosphate (HATU, 1504 mg, 3.96 mmol) was added and the mixture was stirred at room temperature for 10 min. 3,4-Difluoroaniline (851 mg, 6.59 mmol) was added and the mixture was stirred for 2 hours. The mixture was poured out into 100 mL water and the precipitate was filtered off and rinsed with water. The wet powder was dissolved in dichloromethane, dried over $Na_2SO_4$, filtered, and concentrated under reduced pressure to provide ethyl 2-(5-(3,4-difluorophenyl-carbamoyl)-1-methyl-1H-pyrrol-3-yl)-2-oxoacetate (947 mg) as a brown powder. LC method B; Rt: 1.04 min. m/z: 335.1 (M−H)⁻ Exact mass: 336.3.

A solution of ethyl 2-(5-(3,4-difluorophenylcarbamoyl)-1-methyl-1H-pyrrol-3-yl)-2-oxoacetate (937 mg, 2.79 mmol) in 30 ml EtOH was treated with 1N NaOH solution (8.36 mL, 8.36 mmol) and the reaction mixture was heated to 60° C. for 10 min. The reaction mixture was cooled to room temperature and neutralized by the addition of triethylamine hydrochloride (1.53 g, 11.14 mmol). The mixture was evaporated under reduced pressure and the dry residue was co-evaporated twice with toluene (50 mL) to remove remaining traces of water. The crude reaction product 2-(5-(3,4-difluorophenylcarbamoyl)-1-methyl-1H-pyrrol-3-yl)-2-oxoacetic acid (LC method B; Rt: 0.59 min. m/z: 307.1 (M−H)⁻ Exact mass: 308.2) was taken up in dry DMF (20 mL) and divided in two equal portions of 10 mL each for the synthesis of Compounds 10 and 11.

For the synthesis of Compound 10, a solution of crude 2-(5-(3,4-difluorophenylcarbamoyl)-1-methyl-1H-pyrrol-3-yl)-2-oxoacetic acid (roughly 1.4 mmol) in 10 mL of DMF was mixed with triethylamine (582 μL, 4.2 mmol) and 2-(7-aza-1H-benzotriazole-1-yl)-1,1,3,3-tetramethyluronium hexafluorophosphate (HATU, 637 mg, 1.67 mmol) and stirred for 10 min at room temperature. tert-Butylamine (204 mg, 2.79 mmol) was added and the mixture was stirred at room temperature for 3 hours. The reaction mixture was poured out into 100 mL water and the precipitate was filtered off and washed with water. The powder was purified by chromatography over silica gel using a solvent gradient from 0% to 100% EtOAc in heptane as the mobile phase, to afford 4-(2-(tert-butylamino)-2-oxoacetyl)-N-(3,4-difluorophenyl)-1-methyl-1H-pyrrole-2-carboxamide (Compound 10, 220 mg) as a white powder, mp=170.7° C. LC method B; Rt: 1.12 min. m/z: 362.2 (M−H)⁻ Exact mass: 363.1. $^1$H NMR (400 MHz, DMSO-$d_6$) δ ppm 1.37 (s, 9 H), 3.95 (s, 3 H), 7.40 (dt, J=10.6, 9.2 Hz, 1 H), 7.48-7.54 (m, 1 H), 7.64 (d, J=1.8 Hz, 1 H), 7.88 (ddd, J=13.4, 7.6, 2.5 Hz, 1 H), 7.96 (br. s, 1 H), 8.13 (d, J=1.7 Hz, 1 H), 10.26 (s, 1 H).

Compound 11: N-(3,4-difluorophenyl)-1-methyl-4-(2-(3-methyloxetan-3-ylamino)-2-oxoacetyl)-1H-pyrrole-2-carboxamide

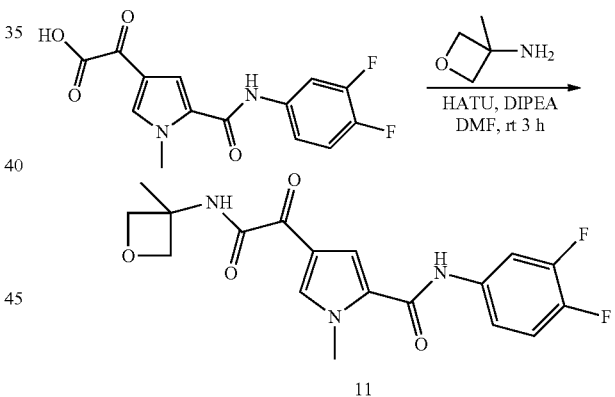

A solution of crude 2-(5-(3,4-difluorophenylcarbamoyl)-1-methyl-1H-pyrrol-3-yl)-2-oxoacetic acid (roughly 1.4 mmol; as described in the procedure for the synthesis of Compound 10) in 10 mL DMF was mixed with triethylamine (776 μL, 5.58 mmol) and 2-(7-aza-1H-benzotriazole-1-yl)-1,1,3,3-tetramethyluronium hexafluorophosphate (HATU, 637 mg, 1.67 mmol) and stirred for 10 min at room temperature. 3-Methyl-3-oxetanamine (243 mg, 2.79 mmol) was added and the mixture was stirred at room temperature for 3 hours. The reaction mixture was poured out into 100 mL water and the precipitate was filtered off and washed with water. The solid residue was re-crystallized from a mixture of 10 mL MeOH and 5 mL water, filtered off and dried in vacuum to afford N-(3,4-difluoro-phenyl)-1-methyl-4-(2-(3-methyl oxetan-3-ylamino)-2-oxoacetyl)-1H-pyrrole-2-carboxamide (Compound 11, 221 mg) as a beige powder, mp=180.7° C. LC method B; Rt: 0.92 min. m/z:

376.2 (M−H)⁻ Exact mass: 377.1. ¹H NMR (400 MHz, DMSO-d₆) δ ppm 1.58 (s, 3 H), 3.96 (s, 3 H), 4.35 (d, J=6.6 Hz, 2 H), 4.72 (d, J=6.4 Hz, 2 H), 7.36-7.45 (m, 1 H), 7.48-7.56 (m, 1 H), 7.68 (d, J=1.5 Hz, 1 H), 7.89 (ddd, J=13.4, 7.5, 2.4 Hz, 1 H), 8.20 (br. d, J=1.1 Hz, 1 H), 9.27 (br. s, 1 H), 10.26 (br. s, 1 H).

Compound 12: 4-(2-(tert-butylamino)-2-oxoacetyl)-1-methyl-N-(3-(trifluoromethyl)phenyl)-1H-pyrrole-2-carboxamide

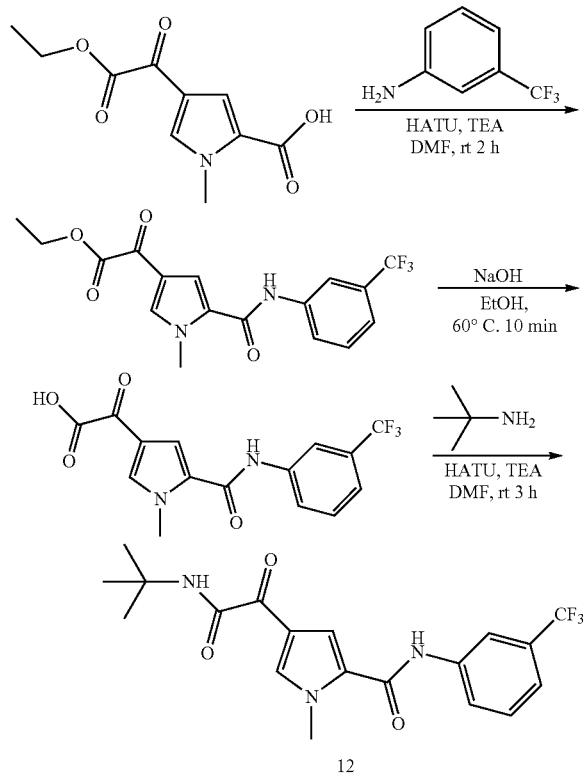

12

4-(2-Ethoxy-2-oxoacetyl)-1-methyl-1H-pyrrole-2-carboxylic acid (750 mg, 3.30 mmol) and triethylamine (917 µL, 6.59 mmol) were mixed in 7.5 mL of DMF. 2-(7-Aza-1H-benzo-triazole-1-yl)-1,1,3,3-tetramethyluronium hexafluorophosphate (HATU, 1504 mg, 3.96 mmol) was added and the mixture was stirred for 10 min. 3-Trifluoromethylaniline (1062 mg, 6.59 mmol) was added and the mixture was stirred for 2 hours at room temperature and was subsequently heated to 40° C. for 30 min. The mixture was poured out into 100 mL water and the precipitate was filtered off and washed with water. The powder was dried in vacuum to provide ethyl 2-(1-methyl-5-(3-(trifluoromethyl)phenyl-carbamoyl)-1H-pyrrol-3-yl)-2-oxoacetate (650 mg) as a beige powder. LC method B; Rt: 1.12 min. m/z: 367.1 (M−H)⁻ Exact mass: 368.1.

A solution of ethyl 2-(1-methyl-5-(3-(trifluoromethyl) phenylcarbamoyl)-1H-pyrrol-3-yl)-2-oxoacetate (650 mg, 1.76 mmol) in 30 ml EtOH was treated with 1N NaOH solution (5.3 mL, 5.3 mmol) and the reaction mixture was stirred at room temperature for 20 min. The reaction mixture was neutralized by the addition of triethylamine hydrochloride (1.22 g, 8.82 mmol). The mixture was evaporated under reduced pressure and the dry residue was co-evaporated twice with 50 ml toluene to remove remaining traces of water. The crude reaction product 2-(1-methyl-5-(3-(trifluoromethyl)phenylcarbamoyl)-1H-pyrrol-3-yl)-2-oxoacetic acid (LC method B; Rt: 0.68 min. m/z: 339.1 (M−H)⁻ Exact mass: 340.1) was taken up in 10 ml of dry DMF and divided in two equal portions of 5 mL each for the synthesis of Compounds 12 and 13.

For the synthesis of Compound 12, a solution of crude 2-(1-methyl-5-(3-(trifluoromethyl)-phenylcarbamoyl)-1H-pyrrol-3-yl)-2-oxoacetic acid (roughly 0.88 mmol) in 5 mL of DMF was mixed with triethylamine (490 µL, 3.53 mmol) and 2-(7-aza-1H-benzotriazole-1-yl)-1,1,3,3-tetramethyluronium hexafluorophosphate (HATU, 1006 mg, 2.64 mmol) and stirred for 10 min at room temperature. tert-Butylamine (193 mg, 2.65 mmol) was added and the mixture was stirred at room temperature for 3 hours. The reaction mixture was poured out into 100 mL water and the precipitate was filtered off and washed with water. The powder was purified by chromatography over silica gel using a solvent gradient from 0% to 100% EtOAc in heptane as the mobile phase, to afford 4-(2-(tert-butylamino)-2-oxoacetyl)-1-methyl-N-(3-(trifluoromethyl)phenyl)-1H-pyrrole-2-carboxamide (Compound 12, 321 mg) as an amorphous white powder. LC method B; Rt: 1.19 min. m/z: 394.2 (M−H)⁻ Exact mass: 395.2. ¹H NMR (360 MHz, DMSO-d₆) δ ppm 1.38 (s, 9 H), 3.98 (s, 3 H), 7.43 (d, J=7.7 Hz, 1 H), 7.58 (br. t, J=8.1, 8.1 Hz, 1 H), 7.72 (d, J=1.8 Hz, 1 H), 7.99-8.04 (m, 2 H), 8.16 (d, J=1.1 Hz, 1 H), 8.21-8.26 (m, 1 H), 10.39 (s, 1 H).

Compound 13: 1-methyl-4-(2-(3-methyloxetan-3-ylamino)-2-oxoacetyl)-N-(3-(trifluoro-methyl)phenyl)-1H-pyrrole-2-carboxamide

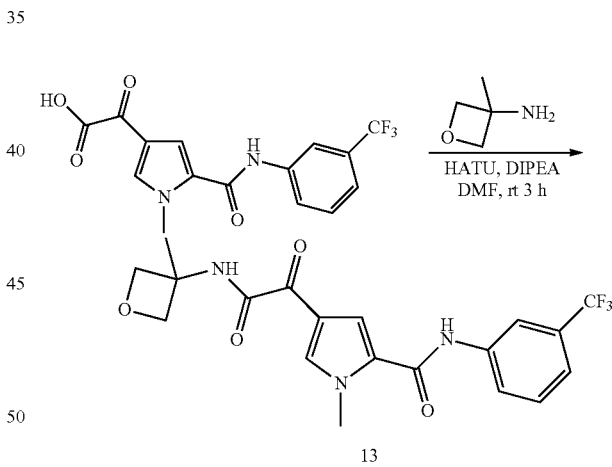

13

A solution of crude 2-(1-methyl-5-(3-(trifluoromethyl) phenylcarbamoyl)-1H-pyrrol-3-yl)-2-oxoacetic acid (roughly 0.88 mmol; as described in the procedure for the synthesis of Compound 12) in 5 mL of DMF was mixed with triethylamine (490 µL, 2.65 mmol) and 2-(7-aza-1H-benzotriazole-1-yl)-1,1,3,3-tetramethyluronium hexafluorophosphate (HATU, 1005 mg, 2.65 mmol) and stirred for 10 min at room temperature. 3-Methyl-3-oxetanamine (230 mg, 2.65 mmol) was added and the mixture was stirred at room temperature for 3 hours. The reaction mixture was poured out into 100 mL water and the precipitate was filtered off and washed with water. The solid residue was dried in vacuum to afford 1-methyl-4-(2-(3-methyloxetan-3-ylamino)-2-oxoacetyl)-N-(3-(trifluoromethyl)phenyl)-1H-pyrrole-2-carboxamide (Compound 13, 316 mg) as an amorphous white powder. LC method B; Rt: 1.01 min. m/z: 408.2 (M−H)⁻ Exact mass: 409.1. $^1$H NMR (400 MHz, DMSO-d$_6$) δ ppm 1.58 (s, 3 H), 3.97 (s, 3 H), 4.35 (d, J=6.6 Hz, 2 H), 4.72 (d, J=6.4 Hz, 2 H), 7.43 (d, J=7.7 Hz, 1 H), 7.58 (br. t, J=7.9, 7.9 Hz, 1 H), 7.74 (d, J=1.8 Hz, 1 H), 7.98-8.04 (m, 1 H), 8.18-8.24 (m, 2 H), 9.28 (s, 1 H), 10.36 (s, 1 H).

Compound 14: 4-(2-(tert-butylamino)-2-oxoacetyl)-N-(3-chloro-4,5-difluorophenyl)-1-methyl-1H-pyrrole-2-carboxamide 2) Elution with a mixture of heptane:DCM in a ratio of 50:50 provided methyl 4-(2-(tert-butylamino)-2-oxoacetyl)-1-methyl-1H-pyrrole-2-carboxylate (830 mg) as the second fraction. $^1$H NMR (360 MHz, DMSO-d$_6$) δ ppm 1.35 (s, 9 H), 3.78 (s, 3 H), 3.93 (s, 3 H), 7.32 (d, J=1.8 Hz, 1 H), 8.02 (s, 1 H), 8.13 (d, J=1.8 Hz, 1 H)

Methyl 4-(2-(tert-butylamino)-2-oxoacetyl)-1-methyl-1H-pyrrole-2-carboxylate (780 mg, 2.9 mmol) was dissolved in 10 mL of MeOH and to the stirred solution 1N NaOH (6.44 mL, 6.44 mmol) was added. After overnight stirring at room temperature, 1N HCl (7 mL) was added

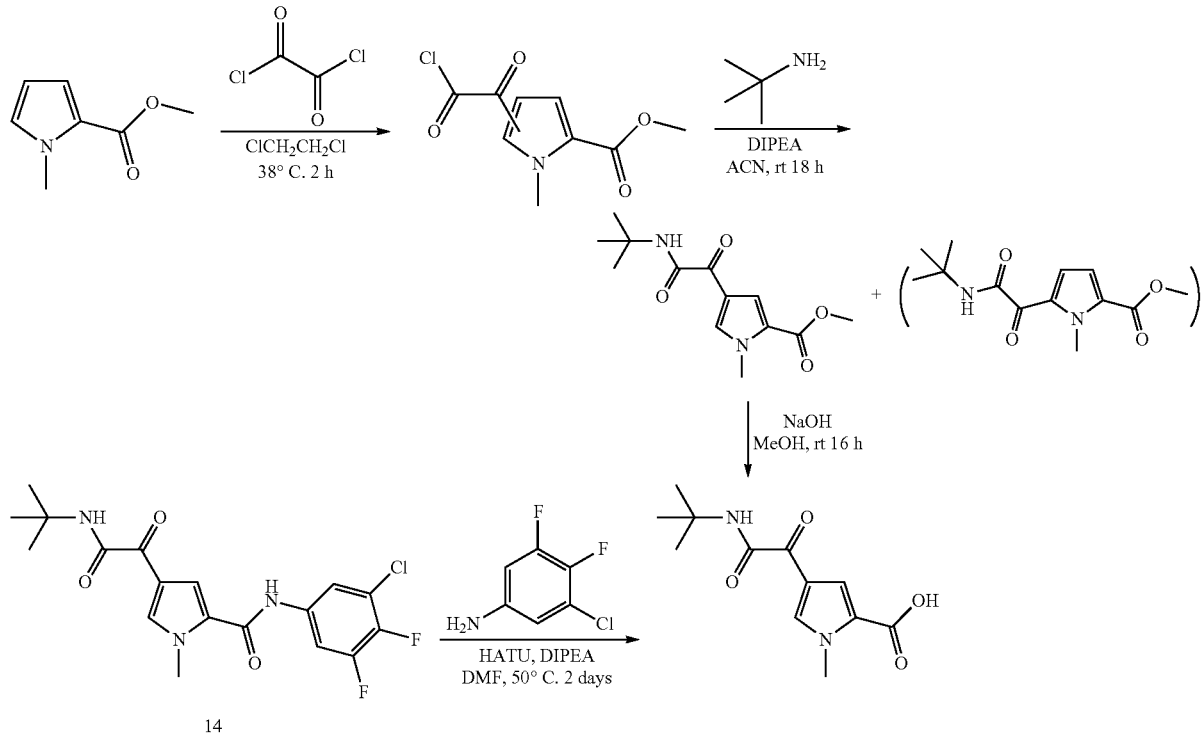

14

Oxalylchloride (2 mL, 23.3 mmol) was added slowly to a stirred solution of methyl 1-methyl-1H-pyrrole-2-carboxylate (2 g, 14.4 mmol) in 10 ml dichloroethane at room temperature. The mixture was subsequently heated to 38° C. for 2 hours. The solvent was removed under reduced pressure and the residue was dissolved in 25 mL of acetonitrile and added portion wise to a stirred solution of tert-butylamine (3.05 mL, 28.7 mmol), and DIPEA (4.95 mL, 28.7 mmol) in 25 mL of acetonitrile. After overnight stirring, the volatiles were removed by evaporation under reduced pressure. The residue was mixed with water, extracted with 2-methyl tetrahydrofuran, dried over Na$_2$SO$_4$, filtered, and evaporated under reduced pressure. The residue was purified by flash chromatography over silica gel using a solvent mixture of heptane and dichloromethane as the mobile phase. Product fractions were combined and evaporated, and finally co-evaporated with MeOH under reduced pressure:

1) Elution with a mixture of heptane:DCM in a ratio of 60:40 provided methyl 5-(2-(tert-butylamino)-2-oxoacetyl)-1-methyl-1H-pyrrole-2-carboxylate (820 mg) as the first fraction. $^1$H NMR (360 MHz, DMSO-d$_6$) δ ppm 1.34 (s, 9 H), 3.82 (s, 3 H), 4.17 (s, 3 H), 6.91 (d, J=4.4 Hz, 1 H), 6.99 (d, J=4.4 Hz, 1 H), 8.35 (s, 1 H).

slowly. Precipitation was completed by the addition of 30 mL water and after stirring for 5 min, the solids were filtered off, washed with water, and dried in vacuum to provide 4-(2-(tert-butylamino)-2-oxoacetyl)-1-methyl-1H-pyrrole-2-carboxylic acid (700 mg) as a white powder. LC method B; Rt: 0.49 min. m/z: 251.1 (M−H)⁻ Exact mass: 252.1. $^1$H NMR (400 MHz, DMSO-d$_6$) δ ppm 1.35 (s, 9 H), 3.91 (s, 3 H), 7.25 (d, J=1.8 Hz, 1 H), 7.96 (s, 1 H), 8.06 (d, J=1.5 Hz, 1 H), 12.78 (br. s., 5 H).

4-(2-(tert-butylamino)-2-oxoacetyl)-1-methyl-1H-pyrrole-2-carboxylic acid (250 mg, 1 mmol), 3-chloro-4,5-difluoroaniline (162 mg, 1 mmol) and N,N-diisopropylethylamine (DIPEA, 384 mg, 3 mmol) were dissolved in 5 mL DMF under N$_2$. 2-(7-Aza-1H-benzo-triazole-1-yl)-1,1,3,3-tetramethyluronium hexafluorophosphate (HATU, 414 mg, 1.09 mmol) was added and the mixture was stirred at 50° C. for 2 days. The reaction mixture was diluted with 100 mL EtOAc and washed with 1N HCl, NaHCO$_3$ solution, and brine. The organic layer was evaporated under reduced pressure and the residue was crystallized from a mixture of 10 mL MeOH and 4 mL water. The crystals were filtered off and dried in vacuum to provide 4-(2-(tert-butylamino)-2-oxoacetyl)-N-(3-chloro-4,5-difluorophenyl)-1-methyl-1H- pyrrole-2-carboxamide (Compound 14, 249 mg) as an amorphous beige powder. LC method B; Rt: 1.25 min. m/z: 396.2 (M–H)⁻ Exact mass: 397.1. ¹H NMR (400 MHz, DMSO-d$_6$) δ ppm 1.36 (s, 9 H), 3.95 (s, 3 H), 7.66 (d, J=1.8 Hz, 1 H), 7.79-7.88 (m, 2 H), 7.97 (s, 1 H), 8.15 (d, J=1.3 Hz, 1 H), 10.33 (s, 1 H).

Compound 15: 4-(2-(tert-butylamino)-2-oxoacetyl)-N-(3-cyano-4-fluorophenyl)-1-methyl-1H-pyrrole-2-carboxamide

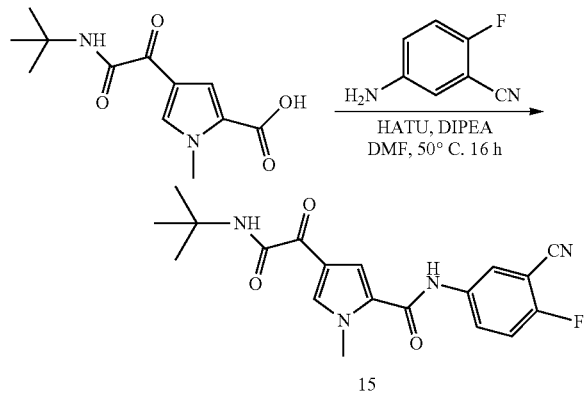

4-(2-(tert-Butylamino)-2-oxoacetyl)-1-methyl-1H-pyrrole-2-carboxylic acid (250 mg, 1 mmol), 3-cyano-4-fluoroaniline (134 mg, 1 mmol), and N,N-diisopropylethylamine (DIPEA, 384 mg, 3 mmol) were dissolved in 5 mL of DMF under N$_2$. 2-(7-Aza-1H-benzotriazole-1-yl)-1,1,3,3-tetramethyluronium hexafluorophosphate (HATU, 414 mg, 1.09 mmol) was added and the mixture was stirred overnight at 50° C. The reaction mixture was diluted with 100 mL EtOAc and washed with 1N HCl, NaHCO$_3$ solution, and brine.

The organic layer was evaporated under reduced pressure and the residue was crystallized from a mixture of 10 mL MeOH and 5 mL water. The crystals were filtered off and dried in vacuum to provide 4-(2-(tert-butylamino)-2-oxoacetyl)-N-(3-cyano-4-fluorophenyl)-1-methyl-1H-pyrrole-2-carboxamide (Compound 15, 292 mg) as an amorphous beige powder. LC method B; Rt: 1.08 min. m/z: 369.2 (M–H)⁻ Exact mass: 370.1. ¹H NMR (400 MHz, DMSO-d$_6$) δ ppm 1.37 (s, 9 H), 3.96 (s, 3 H), 7.52 (t, J=9.1 Hz, 1 H), 7.67 (d, J=2.0 Hz, 1 H), 7.97 (s, 1 H), 8.03 (ddd, J=9.2, 5.0, 2.8 Hz, 1 H), 8.14 (d, J=1.3 Hz, 1 H), 8.23 (dd, J=5.8, 2.8 Hz, 1 H), 10.39 (s, 1 H).

Compound 16: N-(3-Cyano-4-fluorophenyl)-1-methyl-4-{[(3-methyloxetan-3-yl)amino]-(oxo)acetyl}-1H-pyrrole-2-carboxamide Oxalylchloride (7.41 mL, 0.086 mol) was added slowly to a stirring solution of methyl 1-methylpyrrole-2-carboxylate (6 g, 0.0431 mol) in dichloroethane (30 mL). The reaction mixture was stirred as an open vessel for 1 minute, then stirred in a closed vessel at T-int=38° C. (oil-bath=45° C.) for 3 hours, and at room temperature for 18 hours. Methyl 4-(2-chloro-2-oxo-acetyl)-1-methyl-pyrrole-2-carboxylate (1.45 g) was filtered off, washed with dichloroethane (2×), and used as such. Methyl 4-(2-chloro-2-oxo-acetyl)-1-methyl-pyrrole-2-carboxylate (1.45 g, 6.32 mmol) was added portionwise to a stirring solution of 3-methyloxetan-3-amine (1.1 g, 12.6 mmol), DIPEA (2.2 mL, 12.6 mmol), in acetonitrile (50 mL) under N$_2$-atm. The reaction mixture was stirred at room temperature for 1 hour. The volatiles were evaporated. The residue was stirred in H$_2$O (15 mL), filtered off, washed with H$_2$O (3×), and dried at 50° C., resulting in methyl 1-methyl-4-[2-[(3-methyloxetan-3-yl)-amino]-2-oxo-acetyl]pyrrole-2-carboxylate (839 mg). LC method A; Rt: 1.29 min. m/z: 278.9 (M–H)⁻ Exact mass: 280.1. ¹H NMR (400 MHz, DMSO-d$_6$) δ ppm 1.56 (s, 3 H), 3.78 (s, 3 H), 3.93 (s, 3 H), 4.34 (d, J=6.6 Hz, 2 H), 4.70 (d, J=6.4 Hz, 2 H), 7.37 (d, J=2.0 Hz, 1 H), 8.20 (d, J=1.3 Hz, 1 H), 9.25 (s, 1 H). NaOH (1M in H$_2$O, 6.6 mL) was added to a stirring mixture of methyl 1-methyl-4-[2-[(3-methyloxetan-3-yl)amino]-2-oxo-acetyl]-pyrrole-2-carboxylate (939 mg, 2.99 mmol) in MeOH (10 mL). The reaction mixture was stirred at room temperature for 5 h. HCl 1N (7 mL) was added slowly, and precipitation occurred. After stirring for 10 minutes, the mixture was left standing for 16 hours, filtered off, washed with H$_2$O-MeOH 3/1 (2×), and dried at 50° C. in vacuo resulting in 1-methyl-4-[2-[(3-methyloxetan-3-yl)amino]-2-oxo-acetyl]pyrrole-2-carboxylic acid (0.66 g). ¹H NMR (400 MHz, DMSO-d$_6$) δ ppm 1.56 (s, 3 H), 3.92 (s, 3 H), 4.34 (d, J=6.6 Hz, 2 H), 4.70 (d, J=6.4 Hz, 2 H), 7.31 (d, J=1.8 Hz, 1 H), 8.15 (d, J=1.5 Hz, 1 H), 9.22 (s, 1 H), 12.80 (br. s., 1 H). Triethylamine (0.504 mL, 3.63 mmol) was added to a stirring mixture of 1-methyl-4-[2-[(3-methyloxetan-3-yl)amino]-2-oxo-acetyl]pyrrole-2-carboxylic acid (0.322 g, 1.21 mmol), and CH$_3$CN (dried on molecular sieves, 7.5 mL) under N$_2$-atm. To the resulting solution was added 5-amino-2-fluorobenzonitrile (0.187 g, 1.33 mmol) then HATU (0.483 g, 1.27 mmol). The reaction mixture was stirred at 50° C. for 18 hours. The reaction mixture was allowed to reach room temperature, and poured slowly into stirring H$_2$O (25 mL). After stirring for 10 minutes, the product was filtered off, washed with H$_2$O (3×), and dried at 50° C. in vacuo, resulting in compound 16 (291 mg). LC method A; Rt: 1.55 min. m/z: 383.0 (M–H)⁻ Exact mass: 384.1. ¹H NMR (400 MHz, DMSO-d$_6$) δ ppm 1.58 (s, 3 H), 3.96 (s, 3H), 4.35 (d, J=6.6 Hz, 2 H), 4.72 (d, J=6.4 Hz, 2 H), 7.53 (dd, J=9.1 Hz, 1 H), 7.71 (d, J=1.8 Hz, 1 H), 8.04 (ddd, J=9.2, 4.8, 2.6 Hz, 1 H), 8.20-8.26 (m, 2 H), 9.28 (s, 1 H), 10.40 (s, 1 H).

Compound 17: N-(3-Chloro-4,5-difluorophenyl)-1-methyl-4-{[(3-methyloxetan-3-yl)-amino](oxo)acetyl}-1H-pyrrole-2-carboxamide

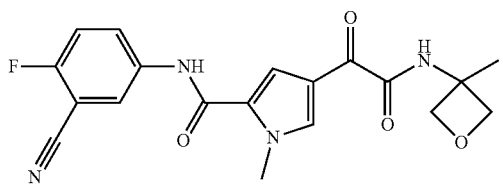 [SMILES: Cn1cc(C(=O)C(=O)NC2(C)COC2)cc1C(=O)Nc1ccc(F)c(C#N)c1]

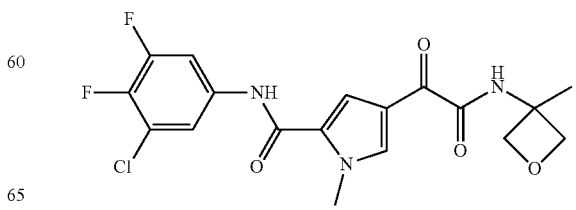

Compound 17 (251 mg) was prepared similarly as described for compound 16 using 3-chloro-4,5-difluoro-aniline instead of 5-amino-2-fluorobenzonitrile. LC method B; Rt: 1.06 min. m/z: 410.2 (M–H)⁻ Exact mass: 411.1. ¹H NMR (400 MHz, DMSO-d₆) δ ppm 1.58 (s, 3 H), 3.95 (s, 3 H), 4.35 (d, J=6.6 Hz, 2 H), 4.72 (d, J=6.4 Hz, 2 H), 7.70 (d, J=1.5 Hz, 1 H), 7.79-7.88 (m, 2 H), 8.22 (d, J=1.3 Hz, 1 H), 9.28 (s, 1 H), 10.34 (s, 1 H).

Compound 18: N-(3-Chloro-4,5-difluorophenyl)-1-methyl-4-(oxo{[(1R)-2,2,2-trifluoro-1-methylethyl]amino}acetyl)-1H-pyrrole-2-carboxamide

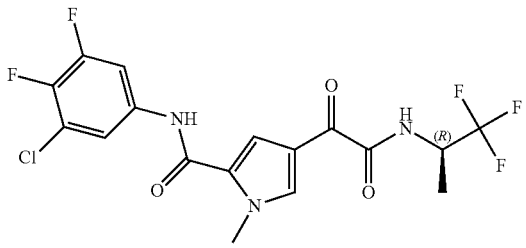

Ethyl 2-chloro-2-oxo-acetate (12.3 g, 89.8 mmol) was dissolved in CH₂Cl₂ (70 mL), and the mixture was cooled on ice/N₂. AlCl₃ (14.4 g, 108 mmol) was added. A solution of methyl 1-methylpyrrole-2-carboxylate (5 g, 35.9 mmol) in CH₂Cl₂ (30 mL) was added dropwise over 15 minutes while cooling on ice. The mixture was stirred at 0° C. for 2 hours. The mixture was poured out in ice water (300 mL) and stirred for 10 minutes. The organic layer was separated. The aqueous layer was extracted with EtOAc (2×100 mL). The combined organic layers were washed with water, dried (Na₂SO₄), and concentrated in vacuo, resulting in an oil which was triturated from diisopropylether (100 mL), resulting in methyl 4-(2-ethoxy-2-oxo-acetyl)-1-methyl-pyrrole-2-carboxylate (6.1 g), containing 2-(5-methoxy-carbonyl-1-methyl-pyrrol-3-yl)-2-oxo-acetic acid as a white powder. ¹H NMR (400 MHz, DMSO-d₆) δ ppm 1.31 (t, J=7.2 Hz, 3 H), 3.79 (s, 3 H), 3.94 (s, 3 H), 4.33 (q, J=7.2 Hz, 2 H), 7.30 (d, J=2.0 Hz, 1 H), 8.06 (d, J=1.8 Hz, 1 H). LC method B; Rt: 0.84 min. m/z: 240.2 (M+H)⁺ Exact mass: 239.1. Methyl 4-(2-ethoxy-2-oxo-acetyl)-1-methyl-pyrrole-2-carboxylate (6.1 g) was suspended in EtOH (40 mL) and the mixture was cooled on ice. NaOH (1M, 24.5 mL), and H₂O was added (30 mL), and the mixture was stirred at 0° C. for 30 minutes. 1N HCl was added until pH=1. Brine (50 mL) was added, and the aqueous layer was extracted with EtOAc (5×). The combined organic layers were washed with brine, dried on Na2SO4, and evaporated to dryness, resulting in a white powder (5.45 g). The powder was re-crystallized from acetonitrile (50 mL) to provide 2-(5-methoxycarbonyl-1-methyl-pyrrol-3-yl)-2-oxo-acetic acid (2.48 g) as a white powder. LC method A; Rt: 0.69 min. m/z: 210.0 (M–H)⁻ Exact mass: 211.0. 2-(5-methoxycarbonyl-1-methyl-pyrrol-3-yl)-2-oxo-acetic acid (2.48 g, 11.6 mmol) (2R)-1,1,1-trifluoropropan-2-amine (1.3 g, 11.6 mmol), and DIPEA (4.5 g, 34.8 mmol) were mixed in DMF (30 mL), and the mixture was cooled in an ice bath. HATU (4.9 g, 12.8 mmol) was added and after 45 minutes the mixture was further stirred at room temperature. After 4 hours the reaction mixture was filtered off, the precipitate was washed with EtOAc, and dried in vacuo, resulting in methyl 1-methyl-4-[2-oxo-2-[[(1R)-2,2,2-trifluoro-1-methylethyl]amino]acetyl]pyrrole-2-carboxylate as a white powder (1.4 g). ¹H NMR (400 MHz, DMSO-d₆) δ ppm 1.34 (d, J=7.0 Hz, 3 H), 3.78 (s, 3 H), 3.93 (s, 3 H), 4.51-4.85 (m, 1 H), 7.35 (d, J=1.8 Hz, 1 H), 8.10-8.15 (1 H), 9.32 (d, J=8.8 Hz, 1 H). LC method B; Rt: 0.93 min. m/z: 305.1 (M–H)⁻ Exact mass: 306.1. The filtrate was mixed with 200 mL EtOAc, washed with 1N HCl, NaHCO₃, and brine, and evaporated to dryness, resulting in a white powder (2.3 g). Methyl 1-methyl-4-[2-oxo-2-[[(1R)-2,2,2-trifluoro-1-methyl-ethyl]amino]acetyl]pyrrole-2-carboxylate (3.7 g) was mixed with MeOH (35 mL). To the resulting suspension, NaOH (1M, 34.9 mL) was added, and the reaction mixture was heated at reflux. After 1 hour, the mixture was cooled on ice, and concentrated HCl was added until pH=1-2. A white precipitate was formed, isolated by filtration, rinsed with water and, dried in vacuo at 50° C., resulting in 1-methyl-4-[2-oxo-2-[[(1R)-2,2,2-trifluoro-1-methyl-ethyl]amino]acetyl]pyrrole-2-carboxylic acid (2.94 g) as an off-white powder. ¹H NMR (400 MHz, DMSO-d₆) δ ppm 1.34 (d, J=7.0 Hz, 3 H), 3.92 (s, 3 H), 4.51-4.86 (m, 1 H), 7.29 (d, J=2.0 Hz, 1 H), 8.07 (d, J=1.3 Hz, 1 H), 9.29 (d, J=9.0 Hz, 1 H), 12.83 (br. s., 1 H). LC method B; Rt: 0.49 min. m/z: 291.1 (M–H)⁻ Exact mass: 292.1. 1-methyl-4-[2-oxo-2-[[(1R)-2,2,2-trifluoro-1-methylethyl]amino]acetyl]pyrrole-2-carboxylic acid (300 mg, 1.03 mmol), 3-chloro-4,5-difluoro-aniline hydrochloride (205 mg, 1.03 mmol), HATU (429 mg, 1.13 mmol) and DIPEA (663 mg, 5.1 mmol) were mixed in DMF (8 mL), and stirred at room temperature for 15 minutes, and next at 50-60° C. After 2 hour and 15 minutes at 50-60° C., 1 equiv. more 3-chloro-4,5-difluoro-aniline hydro-chloride was added and the mixture was stirred at 50° C. overweekend. EtOAc (100 mL) was added and the mixture was washed with 1N HCl, NaHCO₃ and brine. After concentration in vacuo, the obtained residue was purified by preparative HPLC (Stationary phase: Uptisphere C18 ODB—10 µm), Mobile phase: 0.25% NH₄HCO₃ solution in water, CH₃CN), resulting in compound 18 (253 mg). LC method B; Rt: 1.20 min. m/z: 436.1 (M–H)⁻ Exact mass: 437.1. ¹H NMR (400 MHz, DMSO-d₆) δ ppm 1.36 (d, J=7.0 Hz, 3 H), 3.95 (s, 3 H), 4.58-4.81 (m, 1 H), 7.68 (d, J=1.8 Hz, 1 H), 7.75-7.89 (m, 2 H), 8.14 (d, J=1.5 Hz, 1 H), 9.33 (br. s., 1 H), 10.30 (br. s., 1 H).

Compound 19: 4-[(tert-Butylamino)(oxo)acetyl]-N-(3-cyano-4-fluorophenyl)-1,3,5-trimethyl-1H-pyrrole-2-carboxamide

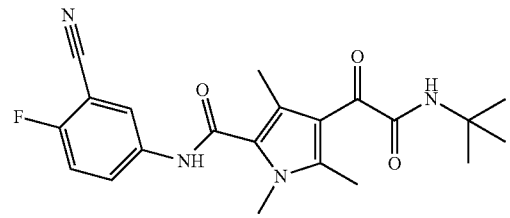 [SMILES: Cc1c(C(=O)C(=O)NC(C)(C)C)c(C)n(C)c1C(=O)Nc1ccc(F)c(C#N)c1]

Ethyl 1,3,5-trimethylpyrrole-2-carboxylate (2 g, 11.0 mmol) was dissolved in CH₂Cl₂ (30 mL) and cooled on ice. A solution of ethyl 2-chloro-2-oxo-acetate (3.8 g, 27.6 mmol) in CH₂Cl₂ (10 mL) was added dropwise, followed by AlCl₃ (4.4 g, 33.1 mmol) in portions. The mixture was further stirred at 0° C. After 2.5 hours, the mixture was poured out into ice water (150 mL) and extracted with EtOAc (2×). The combined organic layers were washed with water and brine, dried ($Na_2SO_4$) and evaporated to dryness, resulting in crude ethyl 4-(2-ethoxy-2-oxo-acetyl)-1,3,5-trimethyl-pyrrole-2-carboxylate as an oil (4.6 g). LC method B; Rt: 1.06 min. m/z: 282.1 (M+H)$^+$ Exact mass: 281.1. Crude ethyl 4-(2-ethoxy-2-oxo-acetyl)-1,3,5-trimethyl-pyrrole-2-carboxylate (4.6 g) was taken up in EtOH (30 mL), NaOH was added (33.1 mL, 1M) was added and the mixture was stirred for 10 minutes at room temperature. The mixture was cooled on ice and 1N HCl was added until pH=1. Water (30 mL) was added and the precipitate was filtered off and dried in vacuo, resulting in 2-(5-ethoxycarbonyl-1,2,4-trimethyl-pyrrol-3-yl)-2-oxo-acetic acid (1.97 g), as a white powder. LC method B; Rt: 0.47 min. m/z: 252.2 (M–H)$^-$ Exact mass: 253.1. $^1$H NMR (400 MHz, DMSO-$d_6$) δ ppm 1.30 (t, J=7.2 Hz, 3 H), 2.39 (s, 3 H), 2.42 (s, 3 H), 3.73 (s, 3 H), 4.27 (q, J=7.0 Hz, 2 H). 2-(5-ethoxycarbonyl-1,2,4-trimethyl-pyrrol-3-yl)-2-oxo-acetic acid (930 mg, 3.5 mmol), 2-methylpropan-2-amine (258 mg, 3.5 mmol) and DIPEA (1.4 g, 10.6 mmol) were mixed in DMF (15 mL). HATU (1.47 g, 3.9 mmol) was added at 0° C. After 10 min, the ice bath was removed and the mixture was stirred at room temperature. After 3 hours, EtOAc (150 mL) was added and the mixture was washed with 1N HCl, $NaHCO_3$ and brine. After drying over $Na_2SO_4$ the mixture was concentrated to dryness, resulting in crude ethyl 4-[2-(tert-butylamino)-2-oxo-acetyl]-1,3,5-trimethyl-pyrrole-2-carboxylate (1.52 g). Crude ethyl 4-[2-(tert-butylamino)-2-oxo-acetyl]-1,3,5-trimethyl-pyrrole-2-carboxylate was dissolved in EtOH (20 mL), NaOH (1M, 10.6 mL) was added and the mixture was stirred at room temperature overnight. While cooling on ice, 1M HCl was added until pH=1 and the formed white precipitate was collected by filtration and dried in vacuo, resulting in 4-[2-(tert-butylamino)-2-oxo-acetyl]-1,3,5-trimethyl-pyrrole-2-carboxylic acid (760 mg). LC method B; Rt: 0.45 min. m/z: 279.1 (M–H)$^-$ Exact mass: 280.1. $^1$H NMR (400 MHz, DMSO-$d_6$) δ ppm 1.33 (s, 9 H), 2.39 (s, 3 H), 2.39 (s, 3 H), 3.74 (s, 3 H), 8.18 (s, 1 H). 4-[2-(tert-butylamino)-2-oxo-acetyl]-1,3,5-trimethyl-pyrrole-2-carboxylic acid (250 mg, 0.89 mmol), 5-amino-2-fluoro-benzonitrile (121 mg, 0.89 mmol), HATU (373 mg, 0.98 mmol) and DIPEA (346 mg, 2.68 mmol) were mixed in DMF (8 mL) and stirred at room temperature in a closed vessel for 3 hours at room temperature and further at 50-60° C. for 3 hours. 5 equiv. more 5-amino-2-fluoro-benzonitrile were added and the mixture was stirred at 50°-60° C. for 2 days. More HATU (100 mg) was added and the mixture was further stirred overnight. The reaction was quenched with a small amount of MeOH, EtOAc was added, the mixture was washed with 1N HCl, $NaHCO_3$ and brine, and concentrated in vacuo, resulting an oil (450 mg) which was purified by preparative HPLC (Stationary phase: RP Vydac Denali C18—10 μm, 200 g, 5 cm), Mobile phase: 0.25% $NH_4HCO_3$ solution in water, $CH_3CN$), resulting in compound 19 (150 mg) as an off-white powder. LC method A; Rt: 1.76 min. m/z: 397.0 (M–H)$^-$ Exact mass: 398.2. $^1$H NMR (400 MHz, DMSO-$d_6$) δ ppm 1.34 (s, 9 H), 2.27 (s, 3 H), 2.42 (s, 3 H), 3.59 (s, 3 H), 7.53 (t, J=9.1 Hz, 1 H), 7.98 (ddd, J=9.2, 4.8, 2.9 Hz, 1 H), 8.16-8.26 (m, 2 H), 10.49 (s, 1 H). Differential scanning calorimetry: From 30 to 300° C. at 10° C./min: Peak: 188.7° C.

Compound 20: 4-[(tert-Butylamino)(oxo)acetyl]-N-(3,4-difluorophenyl)-1,3,5-trimethyl-1H-pyrrole-2-carboxamide

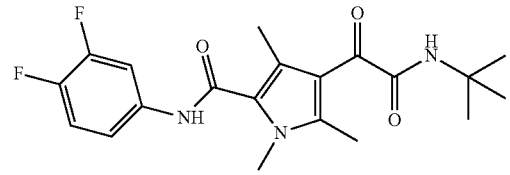 [SMILES: Cc1c(C(=O)C(=O)NC(C)(C)C)c(C)n(C)c1C(=O)Nc1ccc(F)c(F)c1]

Compound 20 (126 mg) was prepared similarly as described for compound 19, using 3,4-difluoroaniline instead of 5-amino-2-fluoro-benzonitrile. LC method A; Rt: 1.84 min. m/z: 390.0 (M–H)$^-$ Exact mass: 391.2. $^1$H NMR (400 MHz, DMSO-$d_6$) δ ppm 1.34 (s, 9 H), 2.26 (s, 3 H), 2.42 (s, 3 H), 3.58 (s, 3 H), 7.35-7.50 (m, 2 H), 7.80-7.93 (m, 1 H), 8.21 (s, 1 H), 10.37 (s, 1 H).

Compound 21: 4-[(tert-Butylamino)(oxo)acetyl]-N-(3,4-difluorophenyl)-1,3-dimethyl-1H-pyrrole-2-carboxamide

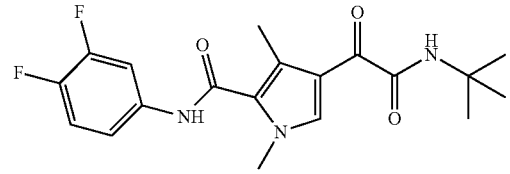 [SMILES: Cc1c(C(=O)C(=O)NC(C)(C)C)cn(C)c1C(=O)Nc1ccc(F)c(F)c1]

Ethyl 1,3-dimethylpyrrole-2-carboxylate (2 g, 11.72 mmol) was dissolved in $CH_2Cl_2$ (40 mL) under $N_2$-atmosphere. The mixture was cooled to 0° C. and ethyl 2-chloro-2-oxo-acetate (1.5 mL) dissolved in $CH_2Cl_2$ (10 mL) was added dropwise. $AlCl_3$ (3.1 g, 23.4 mmol) was added in portions to the reaction mixture at 0° C. The mixture was stirred at 0° C. for 1 hour. The mixture was poured out in ice water (150 mL). The organic layer was separated and the water layer was extracted with $CH_2Cl_2$. The organic fractions were combined, dried ($MgSO_4$), filtered and concentrated in vacuo to resulting in crude ethyl 4-(2-ethoxy-2-oxo-acetyl)-1,3-dimethyl-pyrrole-2-carboxylate. Crude Ethyl 4-(2-ethoxy-2-oxo-acetyl)-1,3-dimethyl-pyrrole-2-carboxylate was dissolved in EtOH (20 mL) and NaOH (23.4 mL, 1 M) was added. The mixture was stirred at room temperature for 10 minutes. The mixture was cooled on a ice bath and HCl (1M in $H_2O$, 23.4 mL, 1 M) was added dropwise. A precipitate was formed. water (20 mL) was added and the precipitate was filtered off, washed with water and diisopropylether and dried in vacuo, resulting in 2-(5-ethoxy-carbonyl-1,4-dimethyl-pyrrol-3-yl)-2-oxo-acetic acid (1.8 g) as a white solid. $^1$H NMR (400 MHz, DMSO-$d_6$) δ ppm 1.31 (t, J=7.1 Hz, 3 H), 2.52 (s, 3 H), 3.87 (s, 3 H), 4.27 (q, J=7.1 Hz, 2 H), 7.91 (s, 1 H), 14.01 (br. s., 1 H). 2-(5-ethoxycarbonyl-1,4-dimethyl-pyrrol-3-yl)-2-oxo-acetic acid (1.8 g, 7.524 mmol), 2-methylpropan-2-amine (877 μL, 8.3 mmol), Hunig's base (3.9 mL, 22.6 mmol) were mixed in DMF (30 mL). HATU (3.15 g, 8.3 mmol) was added portionwise at 0° C. After 30 min, the ice bath was removed and the mixture was stirred at 5° C. for 1 h. The mixture was poured out in EtOAc (200 mL) and washed with 1N HCl solution, sat. NaHCO₃ solution and brine. The organic layer was dried (MgSO₄), filtered and concentrated in vacuo resulting in an oil which was purified by silica gel column chromatography by eluding with CH₂Cl₂. The product fractions were collected and concentrated in vacuo resulting in ethyl 4-[2-(tert-butylamino)-2-oxo-acetyl]-1,3-dimethyl-pyrrole-2-carboxylate (1.8 g) which solidified on standing. LC method B; Rt: 1.16 min. m/z: 293.1 (M–H)⁻ Exact mass: 294.2.

Ethyl 4-[2-(tert-butylamino)-2-oxo-acetyl]-1,3-dimethyl-pyrrole-2-carboxylate (1.8 g, 6.1 mmol) was dissolved in 1,4-dioxane (22.5 mL, 264.1 mmol) and lithium hydroxide monohydrate (513 mg, 12.2 mmol) was added. The mixture was stirred at room temperature for 16 hours. The mixture was concentrated in vacuo. The residue was dissolved in water and neutralized with HCl (1M in H₂O) (11.7 mL, 1 M, 11.7 mmol). The precipitate was filtered off, washed with water and dried in vacuo resulting in 4-[2-(tert-butylamino)-2-oxo-acetyl]-1,3-dimethyl-pyrrole-2-carboxylic acid (1.3 g) as a white solid. 4-[2-(tert-butyl-amino)-2-oxo-acetyl]-1,3-dimethyl-pyrrole-2-carboxylic acid (600 mg, 2.253 mmol), 3,4-difluoroaniline (0.281 mL, 2.82 mmol) DIPEA (1.17 mL, 6.76 mmol) was dissolved in DMF (3.67 mL, 47.3 mmol), HATU (1070 mg, 2.8 mmol) was added and the mixture was stirred at 50° C. for 32 hours. The mixture was poured out in ice water (100 mL) and was extracted with EtOAc. The organic layer was separated, washed with brine, dried (MgSO₄), filtered and concentrated in vacuo. The products were purified silica gel column chromatography using gradient elution with Heptane-EtOAc 100-0 to 50-50. The product fractions were collected and concentrated in vacuo. The product was crystallized from 2-propanol/water, filtered off and dried in vacuo resulting in compound 21 (490 mg) as a solid. LC method B; Rt: 1.13 min. m/z: 376.2 (M–H)⁻ Exact mass: 377.2. ¹H NMR (400 MHz, DMSO-d₆) δ ppm 1.35 (s, 9 H) 2.38 (s, 3 H) 3.76 (s, 3 H) 7.37-7.48 (m, 2 H) 7.82-7.90 (m, 1 H) 7.96 (s, 1 H) 8.03 (s, 1 H) 10.38 (s, 1 H).

Compound 22: 4-[(tert-Butylamino)(oxo)acetyl]-N-(3-cyano-4-fluorophenyl)-1,3-dimethyl-1H-pyrrole-2-carboxamide

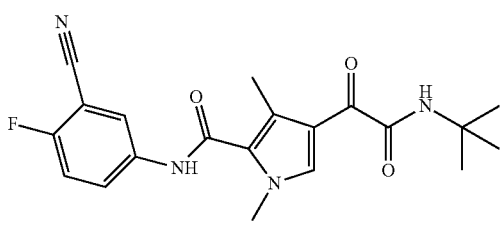 [SMILES: Cc1c(C(=O)C(=O)NC(C)(C)C)cn(C)c1C(=O)Nc1ccc(F)c(C#N)c1]

Compound 22 was prepared similarly as described for compound 21, using of 5-amino-2-fluoro-benzonitrile instead of 3,4-difluoroaniline. LC method B; Rt: 1.07 min. m/z: 383.2 (M–H)⁻ Exact mass: 384.2. ¹H NMR (400 MHz, DMSO-d₆) δ ppm 1.36 (s, 9 H) 2.39 (s, 3 H) 3.77 (s, 3 H) 7.54 (t, J=9.0 Hz, 1 H) 7.94-8.00 (m, 2 H) 8.04 (s, 1 H) 8.17-8.22 (m, 1 H) 10.50 (s, 1 H).

Compound 23: 4-[(tert-Butylamino)(oxo)acetyl]-3-chloro-N-(3-cyano-4-fluorophenyl)-1-methyl-1H-pyrrole-2-carboxamide

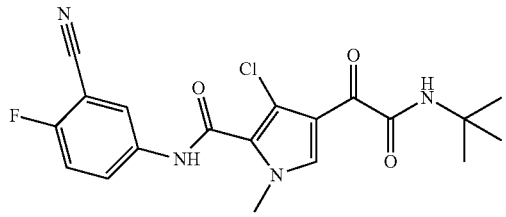 [SMILES: Cn1cc(C(=O)C(=O)NC(C)(C)C)c(Cl)c1C(=O)Nc1ccc(F)c(C#N)c1]

Sodium hydride (1.37 g, 34.3 mmol) was added portionwise over a period of 10 minutes to a mixture of methyl 3-chloro-1H-pyrrole-2-carboxylate (4.8 g, 28.6 mmol) and iodomethane (2.1 g, 34.3 mmol) in DMF (50 mL, 645.7 mmol) cooled with an ice bath. The reaction mixture was allowed to cool to room temperature and stirred for 1 hour. The reaction mixture was acidified with 1M HCl (8 mL) and evaporated to dryness. The residue was dissolved in CH₂Cl₂ (25 mL) and washed with water (25 mL). The product was purified by silica gel chromatography using gradient eluent heptane-EtOAc; 100-0 to 50-50. The product fractions were combined and concentrated in vacuo yielding methyl 3-chloro-1-methyl-pyrrole-2-carboxylate (4.2 g). Methyl 3-chloro-1-methyl-pyrrole-2-carboxylate (2 g, 11.5 mmol) was dissolved in CH₂Cl₂ (40 mL) under N₂ atmosphere. The mixture was cooled to 0° C. and ethyl 2-chloro-2-oxo-acetate (2.6 mL, 23.0 mmol) dissolved in CH₂Cl₂ (10 mL) was added dropwise. AlCl₃ (6.15 g, 46.1 mmol) was added in portions to the reaction mixture at 0° C. The mixture was stirred at 0° C. for 1 hour. The mixture was poured out in ice water (150 mL). The organic layer was separated and the water layer was extracted with CH₂Cl₂. The organic fractions were combined, dried (MgSO₄), filtered and concentrated in vacuo resulting in crude methyl 3-chloro-4-(2-ethoxy-2-oxo-acetyl)-1-methyl-pyrrole-2-carboxylate as an oil. This crude methyl 3-chloro-4-(2-ethoxy-2-oxo-acetyl)-1-methyl-pyrrole-2-carboxylate was dissolved in EtOH (30 mL) and NaOH (34.6 mL, 1 M, 34.6 mmol) was added. The mixture was stirred room temperature for 10 minutes. The mixture was cooled on an ice bath and HCl (1M in H₂O) was added dropwise till pH~4. A precipitate was formed. Water (20 mL) was added and the product was filtered off, washed with water and diisopropylether and dried in vacuo resulting in 2-(4-chloro-5-methoxy-carbonyl-1-methyl-pyrrol-3-yl)-2-oxo-acetic acid (1.93 g) as a white solid. 2-(4-chloro-5-methoxycarbonyl-1-methyl-pyrrol-3-yl)-2-oxo-acetic acid (1 g, 4.07 mmol), 2-methyl-propan-2-amine (0.48 mL, 4.48 mmol), Hunig's base (2.11 mL, 12.2 mmol) were mixed in DMF (16 mL). HATU (1.70 g, 4.48 mmol) was added portionwise at 0° C. After 10 minutes the ice bath was removed and the mixture was stirred for 1 hour. The mixture was poured out in ice water (150 mL). The mixture was extracted with EtOAc and the organic layer was separated, dried (MgSO₄), filtered and concentrated in vacuo resulting in an oil. The product was purified by silica gel chromatography by elution with CH₂Cl₂. The product fractions were collected and concentrated in vacuo resulting in methyl 4-[2-(tert-butylamino)-2-oxo-acetyl]-3-chloro-1-methyl-pyrrole-2-carboxylate (800 mg) which solidified on standing. LC method C; Rt: 1.92 min. m/z: 299.0 (M–H)– Exact mass: 300.1. Methyl 4-[2-(tert-butyl-amino)-2-oxo-acetyl]-

3-chloro-1-methyl-pyrrole-2-carboxylate (100 mg, 0.333 mmol) was dissolved in dry tetrahydrofuran (1 mL). To this was added 5-amino-2-fluorobenzonitrile (58.3 mg, 0.416 mmol) and the mixture was cooled in an ice water bath and purged with nitrogen. Lithium bis(trimethylsilyl)amide (1M in toluene, 0.67 mL, 1 M, 0.67 mmol) was added dropwise under cooling over a period of 2 minutes. The resulting mixture was stirred for 1 hour while cooling was continued, then the mixture was further stirred at room temperature for 16 hours. The mixture was quenched with sat. NH$_4$Cl-sol. The organic layer was separated, dried (MgSO$_4$), filtered and concentrated in vacuo. The product was purified by silica gel column chromatography using gradient elution with Heptane-EtOAc; 100-0->50-50. The product fractions were collected and concentrated in vacuo. The product was triturated in diisopropylether, filtered and dried in vacuo, resulting in compound 23 (37 mg) as a solid. LC method B; Rt: 1.11 min. m/z: 403.2 (M–H)– Exact mass: 404.1. $^1$H NMR (400 MHz, DMSO-d$_6$) δ ppm 1.36 (s, 9 H) 3.82 (s, 3 H) 7.56 (t, J=9.13 Hz, 1 H) 7.93-8.02 (m, 1 H) 8.11 (s, 1 H) 8.14 (s, 1 H) 8.20 (dd, J=5.8, 2.8 Hz, 1 H) 10.70 (s, 1 H).

Compound 24: 3-chloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

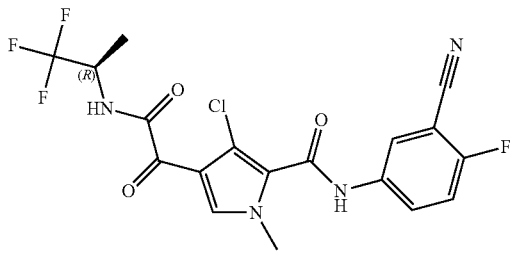

2-(4-chloro-5-methoxycarbonyl-1-methyl-pyrrol-3-yl)-2-oxo-acetic acid (1 g, 4.071 mmol), (R)-1,1,1-trifluoro-2-propylamine (582 mg, 4.89 mmol), Hunig's base (2.11 mL, 12.21 mmol) were mixed in DMF (16 mL). HATU (2012 mg, 5.29 mmol) was added portionwise at 5° C. The mixture was stirred at room temperature for 16 hours. The mixture was poured out in EtOAc (200 mL) and washed with 1N HCl solution, sat. NaHCO$_3$ solution and brine. The organic layer was dried (MgSO$_4$), filtered and concentrated in vacuo. The mixture was purified by silica gel column chromatography using gradient eluent (heptane-EtOAc; 100-0->50-50). The product fractions were collected and concentrated in vacuo resulting in methyl 3-chloro-1-methyl-4[2-oxo-2-[[(1R)-2,2,2-trifluoro-1-methyl-ethyl]amino]acetyl]pyrrole-2-carboxylate (657 mg) as a fluffy solid. Methyl 3-chloro-1-methyl-4-[2-oxo-2-[[(1R)-2,2,2-trifluoro-1-methyl-ethyl]amino]acetyl]pyrrole-2-carboxylate (657 mg, 1.928 mmol) was dissolved in 1,4-dioxane (7.1 mL,) and water (1.6 mL, 87.4 mmol). Lithium hydroxide monohydrate (162 mg, 3.86 mmol) was added. The mixture was stirred at room temperature for 16 hours. The mixture was concentrated in vacuo. The residue was dissolved in water and neutralized with HCl (1M in H$_2$O) (3.86 mL, 1 M, 3.86 mmol). The mixture was extracted with CH$_2$Cl$_2$ and the organic layer was separated, dried (MgSO$_4$), filtered and concentrated in vacuo. The residue was co-evaporated with diisopropylether, resulting in 3-chloro-1-methyl-4-[2-oxo-2-[[(1R)-2,2,2-trifluoro-1-methyl-ethyl]amino]acetyl]pyrrole-2-carboxylic acid (450 mg) as a white solid. 3-chloro-1-methyl-4-[2-oxo-2-[[(1R)-2,2,2-trifluoro-1-methyl-ethyl]amino]acetyl]pyrrole-2-carboxylic acid (450 mg, 1.38 mmol, 5-amino-2-fluorobenzonitrile (242 mg, 1.72 mmol), DIPEA (0.71 mL, 4.13 mmol) were dissolved in DMF (10 mL). HATU (655 mg, 1.72 mmol) was added and the mixture was stirred at 50° C. for 32 hours. The mixture was poured out in ice water (100 mL) and the precipitated product was filtered off and dried in vacuo. The product was crystallized from CH$_3$CN, filtered off and dried in vacuo, resulting in compound 24 (246 mg) as a fluffy white solid. $^1$H NMR (400 MHz, DMSO-d$_6$) δ ppm 1.35 (d, J=7.04 Hz, 3 H) 3.82 (s, 3 H) 4.63-4.72 (m, 1 H) 7.56 (t, J=9.13 Hz, 1 H) 7.98 (ddd, J=9.24, 4.84, 2.64 Hz, 1 H) 8.15 (s, 1 H) 8.21 (dd, J=5.83, 2.75 Hz, 1 H) 9.39 (d, J=8.80 Hz, 1 H) 10.74 (s, 1 H). LC method C; Rt: 1.97 min. m/z: 443.2 (M–H)– Exact mass: 444.1.

Compound 64: N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

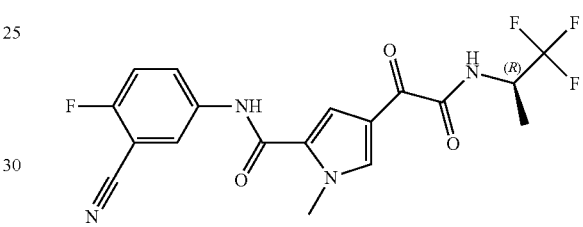

Methyl-4-[2-oxo-2-[[(1R)-2,2,2-trifluoro-1-methyl-ethyl]amino]acetyl]pyrrole-2-carboxylic acid (1700 mg, 5.82 mmol)) was dispersed in DMF (5 mL). Then DIPEA (3.0 mL, 17.45 mmol) was added and this mixture was stirred for 20 minutes. Then HATU (2433 mg, 6.4 mmol) was added followed by 5-amino-2-fluorobenzonitrile (1584 mg, 11.6 mmol). The reaction mixture was stirred at room temperature for 2 hours. Then this mixture was injected directly onto a silica plug. The mixture was purified by silica gel column chromatography using gradient elution from heptane to EtOAc. (100:0 to 0:100) yielding compound 64 as a bright white powder (2.1 g). LC method C; Rt: 1.94 min. m/z: 409.0 (M–H)$^-$ Exact mass: 410.1. $^1$H NMR (400 MHz, DMSO-d$_6$) δ ppm 1.30-1.41 (m, 3 H), 3.94-4.01 (m, 3 H), 4.60-4.79 (m, 1 H), 7.48-7.59 (m, 1 H), 7.67-7.73 (m, 1 H), 7.99-8.08 (m, 1 H), 8.11-8.17 (m, 1 H), 8.20-8.27 (m, 1 H), 9.23-9.45 (m, 1 H), 10.43 (br. s., 1 H)

Compound 25: 5-bromo-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

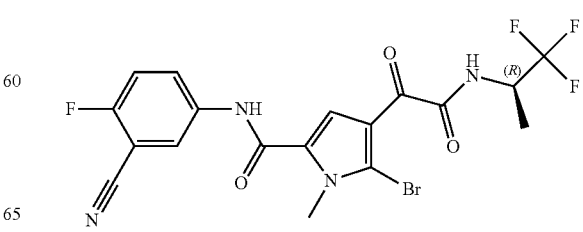

Compound 26: 3-bromo-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

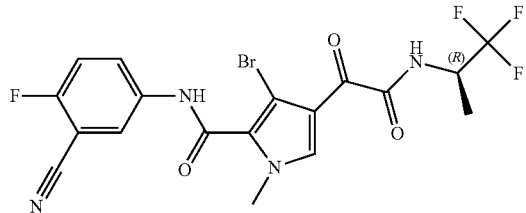

Compound 27: 3,5-dibromo-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

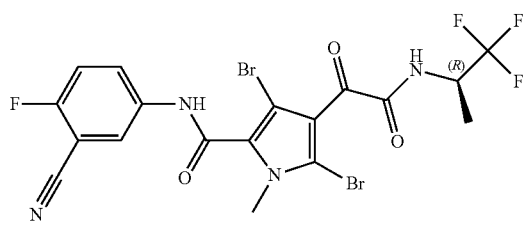

A mixture of compound 64 (2.1 g, 4.99 mmol) in acetonitrile (80 mL) and DMF (15 mL) was cooled to 0° C. To this was added NBS (888 mg, 4.99 mmol) portionwise while stirring. The resulting mixture was stirred at room temperature for 2 hours. The resulting mixture was concentrated in vacuo and the crude was purified using silica gel column chromatography (gradient elution: EtOAc-heptane 0:100 to 100:0) and further via preparative HPLC (Stationary phase: Uptisphere C18 ODB—10 µm, 200 g, 5 cm, Mobile phase: 0.25% NH$_4$HCO$_3$ solution in water, CH$_3$CN). The collected fractions were concentrated in vacuo and co-evaporated twice using ACN/MeOH (2×20 mL/20 mL). Resulting in compound 25 (714 mg), 26 (225 mg) and 27 (117 mg) as bright white powders. Also compound 64 was recuperated (14.2 mg). Compound 25: $^1$H NMR (400 MHz, DMSO-d$_6$) δ ppm 1.35 (d, J=7.0 Hz, 3 H), 3.95 (s, 3 H), 4.58-4.82 (m, 1 H), 7.54 (t, J=9.1 Hz, 1 H), 7.81 (s, 1 H), 7.98-8.05 (m, 1 H), 8.20 (dd, J=5.8, 2.8 Hz, 1 H), 9.23-9.58 (m, 1 H), 10.58 (br. s., 1 H). LC method B; Rt: 1.13 min. m/z: 487.0 (M−H)− Exact mass: 488.0. Compound 26: $^1$H NMR (400 MHz, DMSO-d$_6$) δ ppm 1.35 (d, J=7.0 Hz, 3 H), 3.81 (s, 3 H), 4.60-4.76 (m, 1 H), 7.57 (t, J=9.1 Hz, 1 H), 7.95-8.02 (m, 1 H), 8.17 (s, 1 H), 8.21 (dd, J=5.7, 2.6 Hz, 1 H), 9.31-9.44 (m, 1 H), 10.81 (br. s., 1 H). LC method B; Rt: 1.08 min. m/z: 489.0 (M−H)− Exact mass: 490.0. Compound 27: $^1$H NMR (400 MHz, DMSO-d$_6$) δ ppm 1.35 (d, J=7.0 Hz, 3 H), 3.74 (s, 3 H), 4.59-4.80 (m, 1 H), 7.57 (t, J=9.1 Hz, 1 H), 7.91-8.01 (m, 1 H), 8.20 (dd, J=5.7, 2.6 Hz, 1 H), 9.50 (d, J=6.4 Hz, 1 H), 10.96 (br. s., 1 H). LC method B; Rt: 1.06 min. m/z: 566.9 (M−H)− Exact mass: 567.9.

Compound 28: N-(3-cyano-4-fluoro-phenyl)-1,5-dimethyl-4-[2-oxo-2-[[(1R)-2,2,2-trifluoro-1-methyl-ethyl]amino]acetyl]pyrrole-2-carboxamide

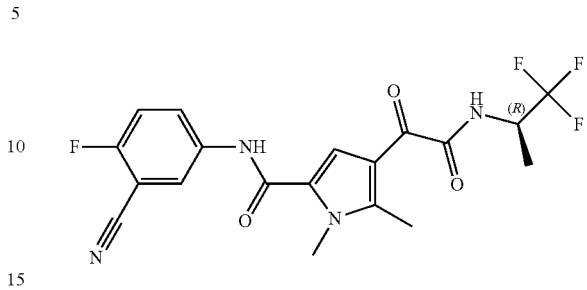

Compound 25 (50 mg, 0.1 mmol), tetramethyltin (0.03 mL, 0.2 mmol) in DMF (0.49 mL, 6.29 mmol) was flushed with nitrogen during 5 minutes.
Tetrakis(triphenylphosphine)palladium(0) (11.8 mg, 0.01 mmol) was added and the reaction mixture was irradiated at 140° C. during 30 minutes by microwave irradiation. The reaction mixture was concentrated and the obtained residue was purified by silica gel column chromatography (gradient from 0 till 100% EtOAc in heptane). The product fractions were concentrated yielding compound 28 as a white powder (104 mg). LC method B; Rt: 1.09 min. m/z: 423.1 (M−H)− Exact mass: 424.1. $^1$H NMR (400 MHz, DMSO-d$_6$) δ ppm 1.34 (d, J=7.0 Hz, 3 H), 2.58 (s, 3 H), 3.85 (s, 3 H), 4.64-4.77 (m, 1 H), 7.52 (t, J=9.1 Hz, 1 H), 7.65 (s, 1 H), 8.02 (ddd, J=9.2, 4.9, 2.6 Hz, 1 H), 8.21 (dd, J=5.9, 2.6 Hz, 1 H), 9.31 (d, J=8.8 Hz, 1 H), 10.46 (br. s., 1 H)

Compound 29: 5-bromo-3-chloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

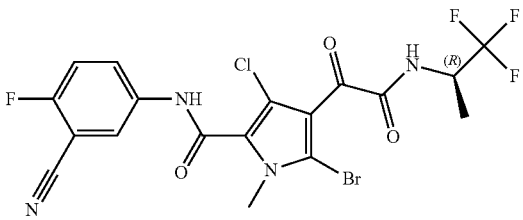

Methyl 3-chloro-1-methyl-4-[2-oxo-2-[[(1R)-2,2,2-trifluoro-1-methyl-ethyl]amino]acetyl]-pyrrole-2-carboxylate (1.9 g, 5.577 mmol) was suspended in acetonitrile (100 mL) and DMF (19 mL). NBS (1489 mg, 8.37 mmol) was added and the mixture was stirred at room temperature for 16 hours. The mixture was concentrated in vacuo. The product was partioned between water and EtOAc. The organic layer was separated, dried (MgSO$_4$), filtered and concentrated in vacuo. The product was purified by silica gel chromatography using gradient eluent Heptane-EtOAc; 100-0 to 50-50. The product fractions were collected and concentrated in vacuo resulting in methyl 5-bromo-3-chloro-1-methyl-4-[2-oxo-2-[[(1R)-2,2,2-trifluoro-1-methyl-ethyl]amino]acetyl]pyrrole-2-carboxylate (1.75 g) as a pale yellow solid. Methyl 5-bromo-3-chloro-1-methyl-4-[2-oxo-2-[[(1R)-2,2,2-trifluoro-1-methyl-ethyl]amino]acetyl]pyrrole-2-carboxylate (1 g, 2.383 mmol) was dissolved in 1,4-dioxane (9 mL) and water (2 mL). Lithium hydroxide monohydrate (200 mg, 4.77 mmol) was added and the mixture was stirred at room temperature for 16 hour. The mixture was concentrated in vacuo and the residue dissolved in water. HCl (1M in $H_2O$) (4.767 mL, 1 M, 4.767 mmol) was added and a precipitate was formed. After stirring for 5 minutes the product was filtered off and dried under vacuum resulting in 5-bromo-3-chloro-1-methyl-4-[2-oxo-2-[[(1R)-2,2,2-trifluoro-1-methyl-ethyl]amino]acetyl]pyrrole-2-carboxylic acid (856 mg) as a white solid. $Et_3N$ (0.88 mL, 6.33 mmol) was added to 5-bromo-3-chloro-1-methyl-4-[2-oxo-2-[[(1R)-2,2,2-trifluoro-1-methyl-ethyl]amino]acetyl]-pyrrole-2-carboxylic acid (856 mg, 2.111 mmol), HATU (1003 mg, 2.64 mmol), 5-amino-2-fluorobenzonitrile (385 mg, 2.74 mmol) in DMF (4.6 mL, 58.9 mmol) and the reaction mixture was stirred 4 hours at 65° C. The mixture was cooled to room temperature and poured out in ice water. The mixture was extracted with EtOAc and the organic layer was separated, dried ($MgSO_4$), filtered and concentrated in vacuo. A purification was performed via Preparative HPLC (Stationary phase: Uptisphere C18 ODB—10 μm, 200 g, 5 cm, Mobile phase: 0.25% $NH_4HCO_3$ solution in water, $CH_3CN$) resulting in compound 29 (203 mg). LC method B; Rt: 1.06 min. m/z: 520.9 $(M-H)^-$ Exact mass: 522.0. $^1H$ NMR (400 MHz, DMSO-$d_6$) δ ppm 1.34 (d, J=7.0 Hz, 3 H) 3.76 (s, 3 H) 4.62-4.74 (m, 1 H) 7.56 (t, J=9.1 Hz, 1 H) 7.97 (ddd, J=9.2, 4.8, 2.9 Hz, 1 H) 8.20 (dd, J=5.7, 2.6 Hz, 1 H) 9.32-9.65 (m, 1 H) 10.30-11.17 (m, 1 H).

Compound 30: 3-chloro-N-(3-cyano-4-fluoro-phenyl)-1,5-dimethyl-4-[2-oxo-2-[[(1R)-2,2,2-trifluoro-1-methyl-ethyl]amino]acetyl]pyrrole-2-carboxamide

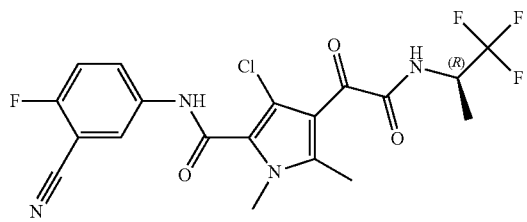

A microwave vial was charged with methyl 5-bromo-3-chloro-1-methyl-4-[2-oxo-2-[[(1R)-2,2,2-trifluoro-1-methyl-ethyl]amino]acetyl]pyrrole-2-carboxylate (200 mg, 0.477 mmol) and tetramethyltin (139.0 μL, 1.291 g/mL, 0.95 mmol) dissolved in DMF (1.5 mL). The mixture was purged with $N_2$ for 5 minutes. Tetrakis(triphenylphosphine)palladium(0) (55.1 mg, 0.048 mmol) was added and the vial was capped. The mixture was irradiated at 140° C. for 30 minutes. The mixture was concentrated in vacuo. The product was purified by silica gel chromatography (using gradient eluent Heptane-EtOAc; 100-0 to 50-50. The product fractions were collected and concentrated in vacuo resulting in methyl 3-chloro-1,5-dimethyl-4-[2-oxo-2-[[(1R)-2,2,2-trifluoro-1-methyl-ethyl]amino]acetyl]pyrrole-2-carboxylate (94 mg) as a white solid. Methyl 3-chloro-1,5-dimethyl-4-[2-oxo-2-[[(1R)-2,2,2-trifluoro-1-methyl-ethyl]amino]acetyl]pyrrole-2-carboxylate (94 mg, 0.265 mmol) was dissolved in 1,4-dioxane (1 mL) and water (0.22 mL, 12.0 mmol). Lithium hydroxide monohydrate (22.2 mg, 0.53 mmol) was added and the mixture was stirred at room temperature for 16 hours. The mixture was concentrated in vacuo and then dissolved in water. HCl (1M in $H_2O$) (0.53 mL, 1 M, 0.53 mmol) was added and the mixture was stirred for 5 minutes at room temperature The mixture was extracted with Me-THF and the organic layer was dried ($MgSO_4$), filtered and concentrated in vacuo resulting in 3-chloro-1,5-dimethyl-4-[2-oxo-2-[[(1R)-2,2,2-trifluoro-1-methyl-ethyl]amino]acetyl]pyrrole-2-carboxylic acid (85 mg) as a solid. 3-chloro-1,5-dimethyl-4-[2-oxo-2-[[(1R)-2,2,2-trifluoro-1-methyl-ethyl]amino]acetyl]pyrrole-2-carboxylic acid (85 mg, 0.249 mmol), 5-amino-2-fluorobenzonitrile (43.8 mg, 0.31 mmol) and DIPEA (0.129 mL, 0.75 g/mL, 0.748 mmol) was dissolved in DMF (1.8 mL). HATU (118.6 mg, 0.31 mmol) was added and the mixture was stirred at 50° C. for 16 hour. The mixture was concentrated in vacuo. The residue was partioned between water and EtOAc. The organic layer was separated, dried ($MgSO_4$), filtered and concentrated in vacuo. A purification was performed via preparative HPLC (Stationary phase: RP)(Bridge Prep C18 OBD—10 μm, 30×150 mm, Mobile phase: 0.25% $NH_4HCO_3$ solution in water, $CH_3CN$) resulting in 3-chloro-N-(3-cyano-4-fluoro-phenyl)-1,5-dimethyl-4-[2-oxo-2-[[(1R)-2,2,2-trifluoro-1-methyl-ethyl]amino]acetyl]pyrrole-2-carboxamide (40 mg) as a white solid. LC method B; Rt: 1.03 min. m/z: 457.0 $(M-H)^-$ Exact mass: 458.1. $^1H$ NMR (400 MHz, DMSO-$d_6$) δ ppm 1.32 (d, J=7.0 Hz, 3 H) 2.47 (s, 3 H) 3.66 (s, 3 H) 4.62-4.74 (m, 1 H) 7.55 (t, J=9.1 Hz, 1 H) 7.95-8.02 (m, 1 H) 8.21 (dd, J=5.8, 2.5 Hz, 1 H) 9.37 (d, J=8.8 Hz, 1 H) 10.75 (s, 1 H).

Compound 31: 3-chloro-N-(3-cyano-4-fluoro-phenyl)-5-cyclopropyl-1-methyl-4-[2-oxo-2-[[(1R)-2,2,2-trifluoro-1-methyl-ethyl]amino]acetyl]pyrrole-2-carboxamide

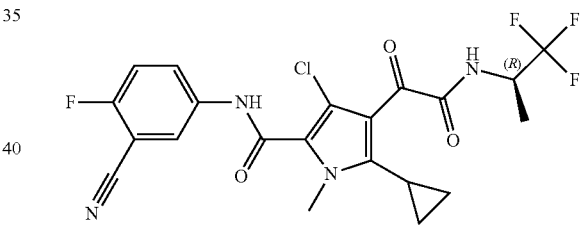

A microwave vial was charged with methyl 5-bromo-3-chloro-1-methyl-4-[2-oxo-2-[[(1R)-2,2,2-trifluoro-1-methyl-ethyl]amino]acetyl]pyrrole-2-carboxylate (150 mg, 0.36 mmol), potassium cyclopropyltrifluoroborate (79.4 mg, 0.54 mmol), $Cs_2CO_3$ (349 mg, 1.07 mmol), DME (4 mL) and water (0.4 mL). The mixture was purged with $N_2$ for 5 minutes. Tetrakis(triphenylphosphine)palladium(0) (82.6 mg, 0.072 mmol) was added and the vial was capped. The mixture was stirred at 110° C. for 16 hours. The mixture was cooled and the residue partioned between sat. $NH_4Cl$-sol and Me-THF. The organic layer was separated, dried ($MgSO_4$), filtered and concentrated in vacuo. The product was purified by silica gel chromatography (10 g, liquid phase) using gradient eluent Heptane-EtOAc; 100-0 to 50-50. The product fractions were collected and concentrated in vacuo resulting in methyl 3-chloro-5-cyclopropyl-1-methyl-4-[2-oxo-2-[[(1R)-2,2,2-trifluoro-1-methyl-ethyl]amino]acetyl]-pyrrole-2-carboxylate (114 mg) as a solid. 3-chloro-N-(3-cyano-4-fluoro-phenyl)-5-cyclo-propyl-1-methyl-4-[2-oxo-2-[[(1R)-2,2,2-trifluoro-1-methyl-ethyl]amino]acetyl]pyrrole-2-carboxamide (22 mg) was synthesized similarly as described for compound 30 using methyl 3-chloro-5-cyclopropyl-1-methyl-4-[2-oxo-2-[[(1R)-2,2,2- trifluoro-1-methyl-ethyl]-amino]acetyl]pyrrole-2-carboxylate instead of methyl 3-chloro-1,5-dimethyl-4-[2-oxo-2-[[(1R)-2,2,2-trifluoro-1-methyl-ethyl]amino]acetyl]pyrrole-2-carboxylate. LC method C; Rt: 1.99 min. m/z: 483.0 (M−H)− Exact mass: 484.0. $^1$H NMR (400 MHz, DMSO-$d_6$) δ ppm 0.47-0.57 (m, 2 H) 0.94-1.05 (m, 2 H) 1.30-1.38 (m, 3 H) 1.77-1.86 (m, 1 H) 3.77 (s, 3 H) 4.61-4.73 (m, 1 H) 7.54 (t, J=9.1 Hz, 1 H) 7.92-7.99 (m, 1 H) 8.20 (dd, J=5.7, 2.6 Hz, 1 H) 9.32 (d, J=9.0 Hz, 1 H) 10.75 (br. s., 1 H)

Compound 32: 4-[2-(tert-butylamino)-2-oxo-acetyl]-3-chloro-N-(3-cyano-4-fluoro-phenyl)-1,5-dimethyl-pyrrole-2-carboxamide

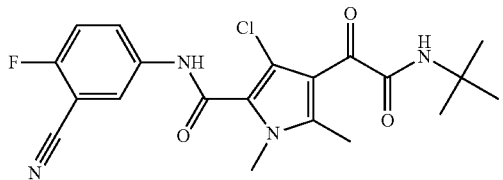

Compound 32 (81 mg) was synthesized similarly as described for compound 30, using methyl 5-bromo-4-[2-(tert-butylamino)-2-oxo-acetyl]-3-chloro-1-methyl-pyrrole-2-carboxylate instead of methyl 5-bromo-3-chloro-1-methyl-4-[2-oxo-2-[[(1R)-2,2,2-trifluoro-1-methyl-ethyl]amino]acetyl]pyrrole-2-carboxylate. LC method B; Rt: 1.03 min. m/z: 417.1 (M−H)− Exact mass: 418.1. $^1$H NMR (400 MHz, DMSO-$d_6$) δ ppm 1.34 (s, 9 H) 2.46 (s, 3 H) 3.65 (s, 3 H) 7.55 (t, J=9.1 Hz, 1 H) 7.94-8.04 (m, 1 H) 8.21 (dd, J=5.7, 2.6 Hz, 1 H) 8.27 (s, 1 H) 10.70 (s, 1 H).

Compound 33: 4-[2-(tert-butylamino)-2-oxo-acetyl]-3-chloro-N-(3-cyano-4-fluoro-phenyl)-1-methyl-5-(trifluoromethyl)pyrrole-2-carboxamide

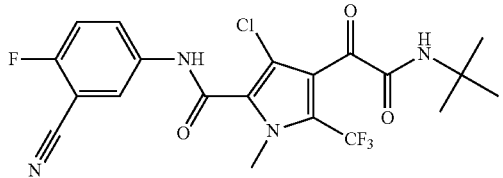

Compound 50 (100 mg, 0.207 mmol) was dissolved in DMF (2 mL). 4-methylmorpholine (45.5 μL, 0.413 mmol), copper (I) iodide (19.7 mg, 0.103 mmol) and fluorosulfonyl-(difluoro)acetic acid methyl ester (78.1 μL, 0.62 mmol) were added. The resulting mixture was stirred at 70° C. for 16 hours. The mixture was cooled and water was added. Saturated ammonium chloride solution (10 mL) was added to the reaction mixture. Then this was extracted using EtOAc (3×15 mL). The combined extracts were dried (MgSO$_4$), filtered and concentrated in vacuo. The obtained residue was purified using column chromatography on silica (gradient elution: ethylacetate: heptane from 0 to 100%). The product fractions were collected and concentrated in vacuo resulting in compound 33 (60 mg) as a white fluffy solid. LC method C; Rt: 2.16 min. m/z: 471.1 (M−H)− Exact mass: 472.1. $^1$H NMR (400 MHz, DMSO-$d_6$) δ ppm 1.33 (s, 9 H) 3.84 (s, 3 H) 7.59 (t, J=9.13 Hz, 1 H) 7.93-8.02 (m, 1 H) 8.21 (dd, J=5.72, 2.64 Hz, 1 H) 8.37 (s, 1 H) 11.15 (s, 1 H). Differential scanning calorimetry: From 30 to 300° C. at 10° C./min: Peak: 195.7° C.

Compound 34: 4-[2-(tert-butylamino)-2-oxo-acetyl]-N-(3-cyano-4-fluoro-phenyl)-3-fluoro-1-methyl-pyrrole-2-carboxamide

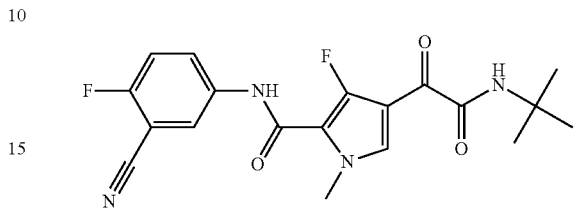

Sodium hydride (5.3 g, 138.7 mmpol, 60%) was added portionwise to ethyl 3-fluoro-1H-pyrrole-2-carboxylate (18.2 g, 115.6 mmol) and iodomethane (19.7 g, 138.7 mmol) in DMF (150 mL) under nitrogen in an ice bath and stirred overnight at room temperature. The reaction mixture was acidified with 1M HCl and concentrated. The obtained residue was dissolved in water/EtOAc. The organic layer was dried over Na$_2$SO$_4$, filtered and concentrated. The residue was dissolved in CH$_3$CN (150 mL), washed with heptane and concentrated at 60° C. and 40 mbar yielding a brown liquid which was submitted to silica gel column chromatography using a gradient from 10 till 25% EtOAc in heptane. The product fractions were concentrated yielding ethyl 3-fluoro-1-methyl-pyrrole-2-carboxylate as a clear oil (10.7 g). More ethyl 3-fluoro-1-methyl-pyrrole-2-carboxylate (1.7 g) was recuperated from the evaporated solvent. Ethyl 3-fluoro-1-methyl-pyrrole-2-carboxylate (1.96 g, 11.5 mmol), ethyl 2-chloro-2-oxo-acetate (1.99 mL, 17.46 mmol) was dissolved in DCM (100 mL) and cooled in an ice bath. AlCl$_3$ (3.06 g, 22.9 mmol) was added and the solution was stirred at 0° C. during 1 hour. The reaction mixture was stirred further 1 hour at room temperature. 1 extra eq of AlCl$_3$ was added and stirred 1 hour. The reaction mixture was cooled in an ice bath and quenched with ice water. The mixture was acidified with HCl 1M. The organic layer was dried over magnesium sulphate filtered and concentrated, resulting in crude ethyl 4-(2-ethoxy-2-oxo-acetyl)-3-fluoro-1-methyl-pyrrole-2-carboxylate (3.29 g). The residue was dissolved in EtOH (20 mL), NaOH (1M in H$_2$O) (11.5 mL, 1 M, 11.5 mmol) was added and the reaction mixture was stirred for 10 minutes. The reaction mixture was neutralised with HCl (1M in H$_2$O) (11.5 mL, 1 M, 11.5 mmol), partially concentrated and extracted with EtOAc/water. The organic layer was dried over magnesium sulphate, filtered and concentrated. The residue was purified by silica gel column chromatography using a gradient from 10 till 100% EtOAc in heptane. The fractions were concentrated yielding 2-(5-ethoxycarbonyl-4-fluoro-1-methyl-pyrrol-3-yl)-2-oxo-acetic acid (1.2 g) as a white powder. LC method C; Rt: 0.89 min. m/z: 242.0 (M−H)− Exact mass: 243.1. Et$_3$N (1.02 mL, 7.35 mmol) was added to a solution of 2-(5-ethoxycarbonyl-4-fluoro-1-methyl-pyrrol-3-yl)-2-oxo-acetic acid (596 mg, 2.45 mmol), 2-methylpropan-2-amine (223.9 mg, 3.06 mmol), and HATU (1164 mg, 3.061 mmol) in DMF (3 mL) and stirred 30 minutes at 65° C. The solution was subjected to silica gel column chromatography using a gradient from 10 till 100% EtOAc in heptane. The product fractions were concentrated yielding ethyl 4-[2-(tert-butylamino)-2-oxoacetyl]-3-fluoro-1-methyl-pyrrole-2-carboxylate (714 mg) as a clear oil which solidified upon standing. LC method C; Rt: 1.98 min. m/z: 299.1 (M+H)+ Exact mass: 298.1. A mixture of ethyl 4-[2-(tert-butylamino)-2-oxo-acetyl]-3-fluoro-1-methyl-pyrrole-2-carboxylate (204 mg, 0.684 mmol), LiOH (49.1 mg, 2.05 mmol) water (10 mL,) and THF (20 mL) was stirred overnight. HCl (1M, 2.1 mL) was added and the THF was distilled off. The formed white precipitate was filtered off and dried in vacuo at 50° C. overnight, resulting in 4-[2-(tert-butylamino)-2-oxo-acetyl]-3-fluoro-1-methyl-pyrrole-2-carboxylic acid (121 mg) as a white powder. LC method C; Rt: 1.03 min. m/z: 269.3 (M−H)− Exact mass: 270.1. $^1$H NMR (400 MHz, DMSO-d$_6$) δ ppm 1.34 (s, 9 H), 3.86 (s, 3 H), 7.97 (d, J=4.4 Hz, 1 H), 8.05 (s, 1 H), 13.05 (br. s, 1 H). Et$_3$N (0.18 mL, 1.29 mmol) was added to 4-[2-(tert-butylamino)-2-oxo-acetyl]-3-fluoro-1-methyl-pyrrole-2-carboxylic acid (115.9 mg, 0.43 mmol), HATU (203.8 mg, 0.54 mmol), 5-amino-2-fluoro-benzonitrile (116.76 mg, 0.86 mmol) dissolved in DMF (0.9 mL) and heated at 65° C. during 4 hours. The reaction mixture was subjected directly to silica gel column chromatography using a gradient from 10 till 100% EtOAc in heptane. The product fractions were concentrated resulting in compound 34 (171 mg) as white crystals which were dried overnight in vacuo at 50° C. LC method C; Rt: 2.03 min. m/z: 387.1 (M−H)− Exact mass: 388.1. Differential scanning calorimetry: From 30 to 300° C. at 10° C./min: Peak: 179.2° C. $^1$H NMR (360 MHz, DMSO-d$_6$) δ ppm 1.35 (s, 9 H), 3.85 (s, 3 H), 7.54 (t, J=9.1 Hz, 1 H), 7.93-7.99 (m, 1 H), 8.04 (d, J=4.4 Hz, 1 H), 8.12 (s, 1 H), 8.18 (dd, J=5.7, 2.7 Hz, 1 H), 10.37 (s, 1 H).

Compound 35: N-(3-cyano-4-fluoro-phenyl)-4-[2-[(3,3-difluoro-1-methyl-cyclobutyl)-amino]-2-oxo-acetyl]-3-fluoro-1-methyl-pyrrole-2-carboxamide

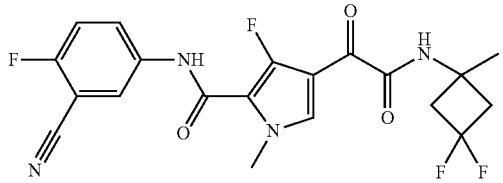

Compound 35 was prepared similarly as described for compound 34, using 4-[2-[(3,3-di-fluoro-1-methyl-cyclobutyl)amino]-2-oxo-acetyl]-3-fluoro-1-methyl-pyrrole-2-carboxylic acid instead of 4-[2-(tert-butylamino)-2-oxo-acetyl]-3-fluoro-1-methyl-pyrrole-2-carboxylic acid. Compound 35 (345 mg) was crystallised by addition of water to a MeOH solution. 4-[2-[(3,3-difluoro-1-methyl-cyclobutyl)amino]-2-oxo-acetyl]-3-fluoro-1-methyl-pyrrole-2-carboxylic acid was prepared similarly as described for 4-[2-(tert-butylamino)-2-oxo-acetyl]-3-fluoro-1-methyl-pyrrole-2-carboxylic acid using 3,3-difluoro-1-methylcyclobutan-amine hydrochloride (commercial from Pharmablock PBN20121019) instead of 2-methyl-propan-2-amine. LC method C; Rt: 1.99 min. m/z: 435.4 (M−H)− Exact mass: 436.1. Differential scanning calorimetry: From 30 to 300° C. at 10° C./min: Peak: 195.0° C. $^1$H NMR (400 MHz, DMSO-d$_6$) δ ppm 1.50 (s, 3 H), 2.61-2.73 (m, 2 H), 2.96-3.10 (m, 2 H), 3.85 (s, 3 H), 7.54 (t, J=9.1 Hz, 1 H), 7.97 (ddd, J=9.2, 4.9, 2.6 Hz, 1 H), 8.10 (d, J=4.4 Hz, 1 H), 8.18 (dd, J=5.7, 2.6 Hz, 1 H), 9.19 (s, 1 H), 10.34 (s, 1 H).

Compound 36: 4-[2-(tert-butylamino)-2-oxo-acetyl]-N-(3-cyano-4-fluoro-phenyl)-3-fluoro-1,5-dimethyl-pyrrole-2-carboxamide

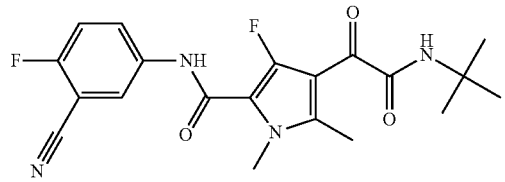 [SMILES: Cc1c(C(=O)C(=O)NC(C)(C)C)c(F)c(C(=O)Nc2ccc(F)c(C#N)c2)n1C]

Ethyl 4-[2-(tert-butylamino)-2-oxo-acetyl]-3-fluoro-1-methyl-pyrrole-2-carboxylate (510 mg, 1.71 mmol), NBS (456.4 mg, 2.56 mmol), DMF (2 mL), ACN (2 mL, 0.786 g/mL, 38.29 mmol) was stirred overnight. Another 1.5 eq NBS was added and the mixture was stirred 30 minutes further. The solution was purified directly by silica gel column chromatography using a gradient from 10 till 100% EtOAc in heptane. The product fractions were concentrated yielding ethyl 5-bromo-4-[2-(tert-butylamino)-2-oxo-acetyl]-3-fluoro-1-methyl-pyrrole-2-carboxylate (255 mg) as a clear oil. $^1$H NMR (360 MHz, DMSO-d$_6$) δ ppm 1.28 (t, J=7.1 Hz, 3 H), 1.32 (s, 9 H), 3.88 (s, 3 H), 4.29 (q, J=7.3 Hz, 2 H), 8.37 (s, 1 H). Tetrakis(triphenylphosphine)palladium(0) (65.9 mg, 0.057 mmol) was added to ethyl 5-bromo-4-[2-(tert-butylamino)-2-oxo-acetyl]-3-fluoro-1-methyl-pyrrole-2-carboxylate (215 mg, 0.57 mmol) and tetramethyltin (214.6 mg, 1.14 mmol) dissolved in DMF (3 mL) and the reaction mixture was heated at 140° C. during 90 minutes by microwave irradiation. The reaction mixture was filtered and concentrated. The obtained residue was purified by silica gel column chromatography using a gradient from 10 till 100% EtOAc in heptane. The product fractions were concentrated yielding ethyl 4-[2-(tert-butylamino)-2-oxo-acetyl]-3-fluoro-1,5-dimethyl-pyrrole-2-carboxylate (149 mg) as a clear colorless resin. $^1$H NMR (400 MHz, DMSO-d$_6$) δ ppm 1.27 (t, J=7.0 Hz, 3 H), 1.32 (s, 9 H), 2.48 (s, 3 H), 3.77 (s, 3 H), 4.26 (q, J=7.1 Hz, 2 H), 8.23 (s, 1 H). A mixture of ethyl 4-[2-(tert-butylamino)-2-oxo-acetyl]-3-fluoro-1,5-dimethyl-pyrrole-2-carboxylate (146 mg, 0.467 mmol), LiOH (33.5 mg, 1.4 mmol), THF (5 mL, 61.44 mmol), water (5 mL, 276.98 mmol) was stirred overnight. HCl (1M in H$_2$O (1.4 mL, 1 M, 1.40 mmol) was added and THF distilled off. The formed white precipitate was filtered off and dried in vacuo at 50° C. resulting in 4-[2-(tert-butylamino)-2-oxo-acetyl]-3-fluoro-1,5-dimethyl-pyrrole-2-carboxylic acid (95 mg) as a white powder. LC method C; Rt: 0.93 min. m/z: 283.1 (M−H)− Exact mass: 284.1. $^1$H NMR (360 MHz, DMSO-d$_6$) δ ppm 1.31 (s, 9 H), 2.48 (s, 3 H), 3.77 (s, 3 H), 8.24 (s, 1 H), 12.92 (br. s, 1 H). Et$_3$N (0.14 mL, 0.97 mmol) was added to a solution of 4-[2-(tert-butylamino)-2-oxo-acetyl]-3-fluoro-1,5-dimethyl-pyrrole-2-carboxylic acid (92 mg, 0.32 mmol), HATU (153.8 mg, 0.41 mmol) and 5-amino-2-fluoro-benzonitrile (88.1 mg, 0.65 mmol) in DMF (1 mL) and the mixture was stirred overnight at 40° C. The reaction mixture was purified directly by silica gel chromatography using a gradient from 10 to 100% EtOAc in heptane. The product fractions were concentrated. The residue was dissolved in methanol (10 mL). The product crystallised upon addition of water. The white crystals were filtered off and dried overnight in vacuo at 50° C., resulting in compound 36 (68 mg). LC method C; Rt: 1.99 min. m/z: 401.1 (M−H)− Exact mass: 402.2. Differential scanning calorimetry: From 30 to 300° C. at 10° C./min: Peak: 153.4° C. $^1$H NMR (400 MHz, DMSO-d$_6$) δ ppm 1.33 (s, 9 H), 2.50 (s, 3 H), 3.71 (s, 3 H), 7.52 (t, J=9.1 Hz, 1 H), 7.93-7.99 (m, 1 H), 8.16 (dd, J=5.9, 2.6 Hz, 1 H), 8.25 (s, 1 H), 10.36 (s, 1 H).

Compound 37: N-(3-cyano-4-fluoro-phenyl)-4-[2-[(3,3-difluoro-1-methyl-cyclobutyl)-amino]-2-oxo-acetyl]-3-fluoro-1,5-dimethyl-pyrrole-2-carboxamide

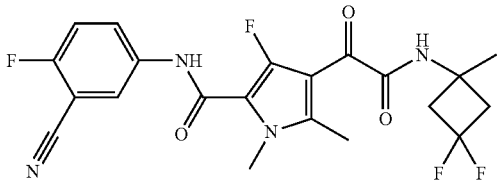

NBS (230.0 mg, 1.29 mmol) was added to a solution of compound 35 (282 mg, 0.646 mmol) in ACN (1 mL) and DMF (1 mL) and stirred 1 hour. The reaction mixture was purified by silica gel column chromatography using a gradient from 10 till 100% EtOAc in heptane. The product fractions were concentrated and the residue crystallised from methanol (20 mL) upon addition of water. The white powder, crude 5-bromo-N-(3-cyano-4-fluoro-phenyl)-4-[2-[(3,3-difluoro-1-methyl-cyclobutyl)amino]-2-oxo-acetyl]-3-fluoro-1-methyl-pyrrole-2-carboxamide (154 mg) was filtered off and dried in vacuo at 50° C. LC method C; Rt: 1.96 min. m/z: 513.0 (M–H)⁻ Exact mass: 514.0. Nitrogen was bubbled through a solution of crude 5-bromo-N-(3-cyano-4-fluoro-phenyl)-4-[2-[(3,3-difluoro-1-methyl-cyclobutyl)-amino]-2-oxo-acetyl]-3-fluoro-1-methyl-pyrrole-2-carboxamide (154 mg), tetramethyltin (112.5 mg, 0.60 mmol) in DMF (2 mL) during 5 minutes.

Tetrakis(triphenylphosphine)palladium(0) (34.5 mg, 0.030 mmol) was added and the reaction mixture was heated at 140° C. during 90 minutes by microwave irradiation. The solution was purified by silica gel column chromatography using a gradient from 10 till 100% EtOAc in heptane. The product fractions were concentrated. The residue was dissolved in methanol (10 mL) and the product crystallised upon addition of water. The white powder was dried in vacuo at 50° C., resulting in compound 37 (64 mg). LC method C;

Rt: 1.92 min. m/z: 449.1 (M–H)⁻ Exact mass: 450.1. ¹H NMR (400 MHz, DMSO-d₆) δ ppm 1.50 (s, 3 H), 2.51 (s, 3 H), 2.62-2.74 (m, 2 H), 2.90-3.03 (m, 2 H), 3.71 (s, 3 H), 7.53 (t, J=9.1 Hz, 1 H), 7.96 (ddd, J=9.2, 4.9, 2.6 Hz, 1 H), 8.16 (dd, J=5.7, 2.6 Hz, 1 H), 9.14 (s, 1 H), 10.40 (s, 1 H).

Compound 38: 3-chloro-N-(3-cyano-4-fluoro-phenyl)-1-methyl-4-[2-oxo-2-[[(1R)-1-(trifluoromethyl)propyl]amino]acetyl]pyrrole-2-carboxamide

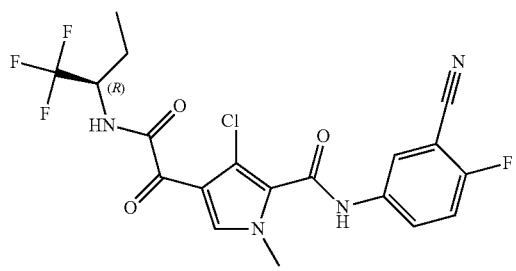

Compound 38 (91 mg) was synthesized similarly as described for compound 40 using (R)-1,1,1-trifluoro-2-butylamine instead of 3,3-difluoro-1-methylcyclobutanamine hydrochloride. LC method C; Rt: 2.08 min. m/z: 457.0 (M–H)– Exact mass: 458.1. ¹H NMR (400 MHz, DMSO-d₆) δ ppm 0.92 (t, J=7.3 Hz, 3 H) 1.68-1.85 (m, 2 H) 3.83 (s, 3 H) 4.40-4.52 (m, 1 H) 7.56 (t, J=9.1 Hz, 1 H) 7.98 (ddd, J=9.2, 4.8, 2.9 Hz, 1 H) 8.14 (s, 1 H) 8.21 (dd, J=5.7, 2.6 Hz, 1 H) 9.31 (d, J=9.2 Hz, 1 H) 10.74 (s, 1 H). Differential scanning calorimetry: From 30 to 300° C. at 10° C./min: Peak: 248.53° C.

Compound 39: 3-chloro-N-(3-cyano-4-fluoro-phenyl)-1-methyl-4-[2-oxo-2-[[1-(tri-fluoromethyl)cyclobutyl]amino]acetyl]pyrrole-2-carboxamide

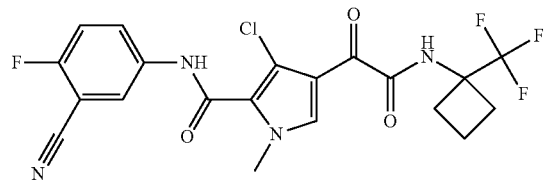 [SMILES: Cn1cc(C(=O)C(=O)NC2(C(F)(F)F)CCC2)c(Cl)c1C(=O)Nc1ccc(F)c(C#N)c1]

Compound 39 (152 mg) was synthesized similarly as described for compound 40 using 1-(trifluoromethyl)cyclobutan-1-amine instead of 3,3-difluoro-1-methylcyclobutanamine hydrochloride. LC method C; Rt: 2.08 min. m/z: 469.1 (M–H)⁻ Exact mass: 470.1. ¹H NMR (400 MHz, DMSO-d₆) δ ppm 1.87-2.03 (m, 2 H) 2.40-2.49 (m, 2 H) 2.53-2.67 (m, 2 H) 3.83 (s, 3 H) 7.56 (t, J=9.1 Hz, 1 H) 7.98 (ddd, J=9.2, 4.8, 2.8 Hz, 1 H) 8.15 (s, 1 H) 8.21 (dd, J=5.8, 2.8 Hz, 1 H) 9.32 (s, 1 H) 10.73 (br. s., 1 H). Differential scanning calorimetry: From 30 to 300° C. at 10° C./min: Peak: 242.2° C.

Compound 40: 3-chloro-N-(3-cyano-4-fluoro-phenyl)-4-[2-[(3,3-difluoro-1-methyl-cyclobutyl)amino]-2-oxo-acetyl]-1-methyl-pyrrole-2-carboxamide

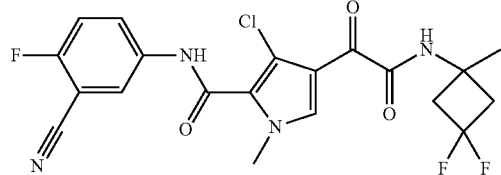 [SMILES: Cn1cc(C(=O)C(=O)NC2(C)CC(F)(F)C2)c(Cl)c1C(=O)Nc1ccc(F)c(C#N)c1]

Methyl 3-chloro-1-methyl-pyrrole-2-carboxylate (6.2 g, 35.7 mmol) and 5-amino-2-fluorobenzonitrile (6.27 g, 44.64 mmol) were dissolved in THF (100 mL). Lithium bis(trimethylsilyl)amide (1 M in THF) (44.6 mL, 1 M, 44.6 mmol) was added dropwise to the reaction mixture at room temperature. After 2 hours the mixture was poured out in sat. NH₄Cl-sol. The mixture was extracted with Me-THF. The organic layer was separated, dried (MgSO₄), filtered and concentrated in vacuo. The residue was triturated in CH₃CN and the product was filtered off. The product was washed with DIPE and dried under vacuum resulting in 3-chloro-N-(3-cyano-4-fluoro-phenyl)-1-methyl-pyrrole-2-carboxamide (5.8 g) as a pale pink solid. 3-chloro-N-(3-cyano-4- fluoro-phenyl)-1-methyl-pyrrole-2-carboxamide (5.8 g, 20.9 mmol) was dissolved in DCM (100 mL) and Me-THF (10 mL). The mixture was cooled on an ice bath. At 0-5° C. Aluminium(III) chloride (7.24 g, 54.31 mmol) was added portionwise. At 0-5° C. ethyl chlorooxoacetate (3.63 mL, 31.80 mmol) was added dropwise to the reaction mixture. The mixture was stirred for 30 minutes at 0-5° C. and was then allowed to rise to room temperature. The mixture was further stirred at room temperature for 32 hours. The mixture was fully converted to 2-[4-chloro-5-[(3-cyano-4-fluoro-phenyl)-carbamoyl]-1-methyl-pyrrol-3-yl]-2-oxo-acetic acid. The mixture was poured out on ice and the organic phase was distilled off. The water layer was extracted with Me-THF and the organic layer was separated, dried (MgSO$_4$), filtered and concentrated in vacuo. The residue was treated with 1 N NaOH solution and the water layer was washed with Me-THF. The water layer was acidified with 1N HCl solution. The water layer was extracted with Me-THF (2×) and the organic layers were combined, dried (MgSO$_4$), filtered and concentrated in vacuo resulting in 2-[4-chloro-5-[(3-cyano-4-fluoro-phenyl)carbamoyl]-1-methyl-pyrrol-3-yl]-2-oxo-acetic acid (3 g) as a white solid. Et$_3$N (0.238 mL, 0.728 g/mL, 1.716 mmol) was added to a solution of 2-[4-chloro-5-[(3-cyano-4-fluoro-phenyl)carbamoyl]-1-methyl-pyrrol-3-yl]-2-oxo-acetic acid (150 mg, 0.429 mmol), 3,3-difluoro-1-methylcyclobutan-amine hydrochloride (64.946 mg, 0.536 mmol), HATU (203.868 mg, 0.536 mmol) in DMF (0.5 mL,) and stirred 30 minutes at 65° C. The mixture was cooled and the solution was subjected to silica gel column chromatography using a gradient from 10 till 100% EtOAc in heptane. The product fractions were concentrated. The product was triturated in DIPE, filtered and dried in vacuo resulting in compound 40 (135 mg) as a white fluffy solid. LC method C; Rt: 2.02 min. m/z: 451.3 (M−H)$^-$ Exact mass: 452.1. $^1$H NMR (400 MHz, DMSO-d$_6$) δ ppm 1.50 (s, 3 H) 2.59-2.75 (m, 2 H) 2.95-3.11 (m, 2 H) 3.82 (s, 3 H) 7.56 (t, J=9.13 Hz, 1 H) 7.98 (ddd, J=9.13, 4.84, 2.75 Hz, 1 H) 8.16-8.25 (m, 2 H) 9.18 (s, 1 H) 10.71 (s, 1 H). Differential scanning calorimetry: From 30 to 300° C. at 10° C./min: Peak: 222.1° C.

Synthesis of 3-(trifluoromethyl)tetrahydrofuran-3-amine hydrochloride

A mixture of 3-oxotetrahydrofuran (30 g, 348.5 mmol), benzylamine (39.2 g, 365.8 mmol), MgSO$_4$ (21 g, 174.5 mmol) and CH$_2$Cl$_2$ (200 mL) was stirred at 28° C. for 24 hours. The mixture was filtrated. The filtrate was concentrated in vacuo and the obtained residue (63.1 g) was used directly in the next step. The obtained residue (63 g) was dissolved in acetonitrile (600 mL). Trifluoroacetic acid (45 g, 394 mmol), potassium hydrogenfluoride (22.5 g, 288 mmol) and DMF (60 mL) were added to the mixture at 0° C. The mixture was stirred at 0° for 10 minutes. (trifluoromethyl)trimethylsilane (77 g, 541 mmol) was added to the reaction mixture and the mixture was stirred at ambient temperature for 12 h. Saturated aqueous Na$_2$CO$_3$ (200 mL) was added and the mixture was stirred for 5 min. The mixture was diluted with water (500 mL), and extracted with ethyl acetate (3×300 mL). The combined organic layers were washed with water and brine, dried over Na$_2$SO$_4$ and evaporated under reduced pressure. The obtained residue was dissolved in 2M HCl/MeOH and the solvent was evaporated. The resulting hydrochloride salt was crystallized from CH$_3$CN to provide N-benzyl-3-(trifluoromethyl)tetrahydrofuran-3-amine (30.5 g). A mixture of N-benzyl-3-(trifluoromethyl)tetrahydrofuran-3-amine (30.5 g), palladium on alumina (1.5 g) and MeOH was stirred under H$_2$ (20 psi) atmosphere at 28° C. for 12 hours.

The mixture was filtered and the filtrate was concentrated in vacuo resulting in 3-(trifluoromethyl)tetrahydrofuran-3-amine hydrochloride (20.5 g). $^1$H NMR (400 MHz, DMSO-d$_6$) δ ppm 2.21-2.43 (m, 2 H) 3.83-4.16 (m, 4 H) 9.68 (br. s., 3 H).

Compound 41: 3-chloro-N-(3-cyano-4-fluoro-phenyl)-1,5-dimethyl-4-[2-oxo-2-[[3-(tri-fluoromethyl)tetrahydrofuran-3-yl]amino]acetyl]pyrrole-2-carboxamide

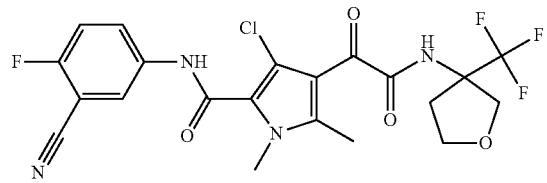 [SMILES: Cc1c(C(=O)C(=O)NC2(C(F)(F)F)CCOC2)c(Cl)c(C(=O)Nc2ccc(F)c(C#N)c2)n1C]

3-chloro-N-(3-cyano-4-fluoro-phenyl)-1,5-dimethyl-4-[2-oxo-2-[[3-(trifluoromethyl)-tetrahydrofuran-3-yl]amino]acetyl]pyrrole-2-carboxamide (58 mg) was synthesized similarly as described for compound 43 using racemic 3-(trifluoromethyl)tetrahydrofuran-3-amine instead of 1-(trifluoromethyl)cyclobutan-1-amine. LC method B; Rt: 0.98 min. m/z: 499.0 (M−H)− Exact mass: 500.1. $^1$H NMR (400 MHz, DMSO-d$_6$) δ ppm 2.25-2.40 (m, 1 H) 2.45-2.56 (m, 4 H) 3.66 (s, 3 H) 3.71-3.84 (m, 1 H) 3.85-3.96 (m, 1 H) 4.12-4.26 (m, 2 H) 7.55 (t, J=9.1 Hz, 1 H) 7.99 (ddd, J=9.2, 4.8, 2.9 Hz, 1 H) 8.21 (dd, J=5.7, 2.6 Hz, 1 H) 9.39 (s, 1 H) 10.75 (s, 1 H).

Compound 42: 3-chloro-N-(3-cyano-4-fluoro-phenyl)-1,5-dimethyl-4-[2-oxo-2-[[(1R)-1-(trifluoromethyl)propyl]amino]acetyl]pyrrole-2-carboxamide

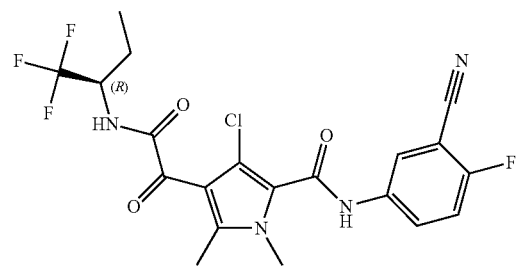

3-chloro-N-(3-cyano-4-fluoro-phenyl)-1,5-dimethyl-4-[2-oxo-2-[[(1R)-1-(trifluoro-methyl)propyl]amino]acetyl]pyrrole-2-carboxamide (5 mg) was synthesized similarly as described for compound 43 using (R)-1,1,1-trifluoro-2-butylamine instead of 1-(trifluoromethyl)cyclobutan-1-amine. LC method C; Rt: 1.97 min. m/z: 471.1 (M−H)− Exact mass: 472.1. $^1$H NMR (400 MHz, DMSO-d$_6$) δ ppm 0.97 (t, J=7.4 Hz, 3 H) 1.59-1.73 (m, 1 H) 1.73-1.87 (m, 1 H) 2.47 (s, 3 H) 3.66 (s, 3 H) 4.39-4.55 (m, 1 H) 7.55 (t, J=9.1 Hz, 1 H) 7.93-8.03 (m, 1 H) 8.21 (dd, J=5.7, 2.6 Hz, 1 H) 9.29 (d, J=8.8 Hz, 1 H) 10.75 (s, 1 H).

Compound 43: 3-chloro-N-(3-cyano-4-fluoro-phenyl)-1,5-dimethyl-4-[2-oxo-2-[[1-(tri-fluoromethyl)cyclobutyl]amino]acetyl]pyrrole-2-carboxamide

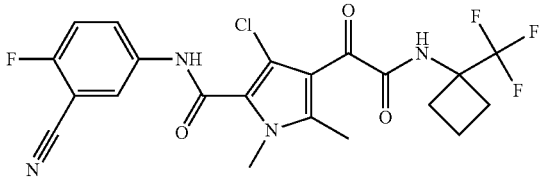 [SMILES: Cc1c(C(=O)C(=O)NC2(C(F)(F)F)CCC2)c(Cl)c(C(=O)Nc2ccc(F)c(C#N)c2)n1C]

3-chloro-N-(3-cyano-4-fluoro-phenyl)-1-methyl-pyrrole-2-carboxamide (4 g, 14.405 mmol) was dissolved in DCM (69 mL) and the mixture was cooled on an ice bath. At 0-5° C. ethyl chlorooxoacetate (2.50 mL, 21.9 mmol) was added. At 0-5° C. aluminium (III) chloride (4.99 g, 37.45 mmol) was added portionwise to the reaction mixture. The mixture was stirred for 30 minutes at 0-5° C. and was then allowed to rise to room temperature. The mixture was stirred at room temperature for 1 hour. The mixture was cooled to 0-5° C. with an ice bath. EtOH (20 mL) was carefully added. A clear solution was formed and the mixture was stirred at room temperature for 1 h. The mixture was quenched on ice. The organic layer was separated and the water layer was extracted with Me-THF. The organic layers were combined, dried (MgSO$_4$), filtered and concentrated in vacuo. The residue was suspended in little Me-THF and the product was filtered off resulting in ethyl 2-[4-chloro-5-[(3-cyano-4-fluoro-phenyl)carbamoyl]-1-methyl-pyrrol-3-yl]-2-oxo-acetate (1.8 g) as a white solid. Ethyl 2-[2-bromo-4-chloro-5-[(3-cyano-4-fluoro-phenyl)carbamoyl]-1-methyl-pyrrol-3-yl]-2-oxo-acetate (1.8 g) was synthesized similarly as described for 2-[2-bromo-4-chloro-5-[(3-cyano-4-fluoro-phenyl)carbamoyl]-1-methyl-pyrrol-3-yl]-2-oxo-acetic acid in the synthesis of compound 47 using ethyl 2-[4-chloro-5-[(3-cyano-4-fluoro-phenyl)carbamoyl]-1-methyl-pyrrol-3-yl]-2-oxo-acetate instead of 2-[4-chloro-5-[(3-cyano-4-fluoro-phenyl)carbamoyl]-1-methyl-pyrrol-3-yl]-2-oxo-acetic acid. Ethyl 2-[4-chloro-5-[(3-cyano-4-fluoro-phenyl)-carbamoyl]-1,2-dimethyl-pyrrol-3-yl]-2-oxo-acetate (700 mg) was synthesized similarly as described for 2-[4-chloro-5-[(3-cyano-4-fluoro-phenyl)carbamoyl]-1,2-dimethyl-pyrrol-3-yl]-2-oxo-acetic acid in the synthesis of compound 47 using ethyl 2-[2-bromo-4-chloro-5-[(3-cyano-4-fluoro-phenyl)carbamoyl]-1-methyl-pyrrol-3-yl]-2-oxo-acetate (1 g) instead of 2-[2-bromo-4-chloro-5-[(3-cyano-4-fluoro-phenyl)carbamoyl]-1-methyl-pyrrol-3-yl]-2-oxo-acetic acid. Ethyl 2-[4-chloro-5-[(3-cyano-4-fluoro-phenyl)carbamoyl]-1,2-dimethyl-pyrrol-3-yl]-2-oxo-acetate (700 mg, 1.787 mmol) was dissolved in 1,4-dioxane (6.6 mL, 77.2 mmol) and water (1.5 mL). Lithium hydroxide monohydrate (150 mg, 3.57 mmol) was added and the mixture was stirred at room temperature for 16 hours. The mixture was concentrated in vacuo and the residue dissolved in water. HCl (1M in H$_2$O) (3.6 mL, 1 M, 3.573 mmol) was added and a precipitate was formed. The product was filtered off and dried under vacuum resulting in 2-[4-chloro-5-[(3-cyano-4-fluoro-phenyl)carbamoyl]-1,2-dimethyl-pyrrol-3-yl]-2-oxo-acetic acid (400 mg) as a white solid. Compound 43 (33 mg) was synthesized similarly as described for compound 47 starting from 2-[4-chloro-5-[(3-cyano-4-fluoro-phenyl)carbamoyl]-1,2-dimethyl-pyrrol-3-yl]-2-oxo-acetic acid using 1-(trifluoromethyl)cyclobutan-1-amine instead of 3,3-difluoro-1-methylcyclobutanamine hydrochloride. LC method C; Rt: 1.97 min. m/z: 483.1 (M−H)⁻ Exact mass: 484.1. $^1$H NMR (400 MHz, DMSO-d$_6$) δ ppm 1.81-2.10 (m, 2 H) 2.42-2.57 (m, 7 H) 3.66 (s, 3 H) 7.55 (t, J=9.1 Hz, 1 H) 7.99 (ddd, J=9.1, 4.8, 2.8 Hz, 1 H) 8.21 (dd, J=5.7, 2.6 Hz, 1 H) 9.28 (s, 1 H) 10.75 (s, 1 H). Differential scanning calorimetry: From 30 to 300° C. at 10° C./min: Peak: 218.9° C.

Compound 44: 3-chloro-N-(3-cyano-4-fluoro-phenyl)-1,5-dimethyl-4-[2-[(3-methyloxetan-3-yl)amino]-2-oxo-acetyl]pyrrole-2-carboxamide

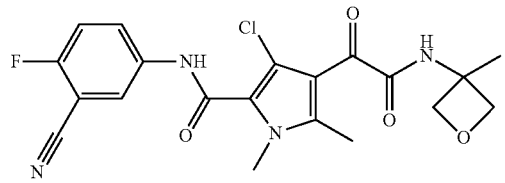 [SMILES: Cc1c(C(=O)C(=O)NC2(C)COC2)c(Cl)c(C(=O)Nc2ccc(F)c(C#N)c2)n1C]

Compound 44 (60 mg) was synthesized similarly as described for compound 47 using 3-methyloxetan-3-amine instead of 3,3-difluoro-1-methylcyclobutanamine hydrochloride. LC method C; Rt: 1.60 min. m/z: 431.1 (M−H)⁻ Exact mass: 432.1. $^1$H NMR (400 MHz, DMSO-d$_6$) δ ppm 1.59 (s, 3 H) 2.47 (s, 3 H) 3.66 (s, 3 H) 4.37 (d, J=6.4 Hz, 2 H) 4.70 (d, J=6.4 Hz, 2 H) 7.55 (t, J=9.1 Hz, 1 H) 7.99 (ddd, J=9.2, 4.8, 2.6 Hz, 1 H) 8.21 (dd, J=5.7, 2.6 Hz, 1 H) 9.23 (s, 1 H) 10.73 (s, 1 H). Differential scanning calorimetry: From 30 to 300° C. at 10° C./min: Peak: 210.4° C.

Compound 45: 3-chloro-N-(3-cyano-4-fluoro-phenyl)-4-[2-(isopropylamino)-2-oxo-acetyl]-1,5-dimethyl-pyrrole-2-carboxamide

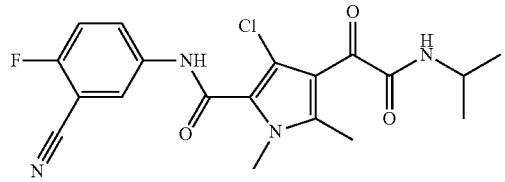 [SMILES: Cc1c(C(=O)C(=O)NC(C)C)c(Cl)c(C(=O)Nc2ccc(F)c(C#N)c2)n1C]

Compound 45 (59 mg) was synthesized similarly as described for compound 47 using isopropylamine instead of 3,3-difluoro-1-methylcyclobutanamine hydrochloride. LC method C; Rt: 1.76 min. m/z: 403.1 (M−H)⁻ Exact mass: 404.1. $^1$H NMR (400 MHz, DMSO-d$_6$) δ ppm 1.14 (d, J=6.6 Hz, 6 H) 2.45 (s, 3 H) 3.65 (s, 3 H) 3.90-4.02 (m, 1 H) 7.55 (t, J=9.1 Hz, 1 H) 7.98 (ddd, J=9.2, 4.8, 2.8 Hz, 1 H) 8.21 (dd, J=5.7, 2.6 Hz, 1 H) 8.58 (d, J=7.7 Hz, 1 H) 10.71 (s, 1 H). Differential scanning calorimetry: From 30 to 300° C. at 10° C./min: Peak: 238.3° C.

Compound 46: 3-chloro-N-(3-cyano-4-fluoro-phenyl)-4-[2-[[(1R)-2,2-difluoro-1-methyl-propyl]amino]-2-oxo-acetyl]-1,5-dimethyl-pyrrole-2-carboxamide

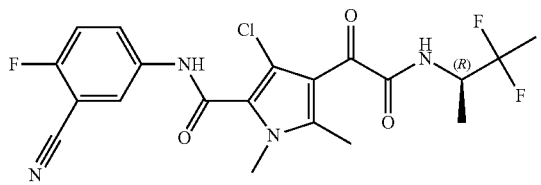

Compound 46 (64 mg) was synthesized similarly as described for compound 47 using (2R)-3,3-difluorobutan-2-amine instead of 3,3-difluoro-1-methylcyclobutanamine hydrochloride. LC method C; Rt: 1.85 min. m/z: 453.1 (M–H)– Exact mass: 454.1. $^1$H NMR (400 MHz, DMSO-d$_6$) δ ppm 1.21 (d, J=6.8 Hz, 3 H) 1.62 (t, J=19.3 Hz, 3 H) 2.47 (s, 3 H) 3.66 (s, 3 H) 4.23-4.39 (m, 1 H) 7.55 (t, J=9.1 Hz, 1 H) 7.93-8.02 (m, 1 H) 8.21 (dd, J=5.7, 0.6 Hz, 1 H) 9.03 (d, J=9.0 Hz, 1 H) 10.74 (s, 1 H) Differential scanning calorimetry: From 30 to 300° C. at 10° C./min: Peak: 240.5° C.

Compound 47: 3-chloro-N-(3-cyano-4-fluoro-phenyl)-4-[2-[(3,3-difluoro-1-methyl-cyclo-butyl)amino]-2-oxo-acetyl]-1,5-dimethyl-pyrrole-2-carboxamide

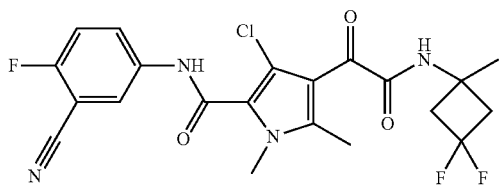 [SMILES: Cc1c(C(=O)C(=O)NC2(C)CC(F)(F)C2)c(Cl)c(C(=O)Nc2ccc(F)c(C#N)c2)n1C]

2-[4-chloro-5-[(3-cyano-4-fluoro-phenyl)carbamoyl]-1-methyl-pyrrol-3-yl]-2-oxo-acetic acid (250 mg, 0.715 mmol) was suspended in CH$_3$CN (4.9 mL, 93.3 mmol) and DMF (2.4 mL, 31.4 mmol). NBS (190.9 mg, 1.07 mmol) was added and the mixture was stirred at room temperature for 16 h. The CH$_3$CN was distilled of and the residue was poured out in water. The product was filtered off, washed with water and dried under vacuum resulting in 2-[2-bromo-4-chloro-5-[(3-cyano-4-fluoro-phenyl)carbamoyl]-1-methyl-pyrrol-3-yl]-2-oxo-acetic acid (306 mg). A solution of 2-[2-bromo-4-chloro-5-[(3-cyano-4-fluoro-phenyl)-carbamoyl]-1-methyl-pyrrol-3-yl]-2-oxo-acetic acid (306 mg, 0.714 mmol), tetramethyltin (0.208 mL, 1.43 mmol) in DMF (3.4 mL) was flushed with nitrogen during 5 minutes. Tetrakis(triphenylphosphine)palladium(0) (82.5 mg, 0.071 mmol) was added and the reaction mixture was heated at 140° C. during 30 min by microwave irradiation. The reaction mixture was concentrated resulting in 2-[4-chloro-5-[(3-cyano-4-fluoro-phenyl)carbamoyl]-1,2-dimethyl-pyrrol-3-yl]-2-oxo-acetic acid (260 mg) and used as such in the next step. Et$_3$N (0.397 mL, 2.9 mmol) was added to a solution of 2-[4-chloro-5-[(3-cyano-4-fluoro-phenyl)-carbamoyl]-1,2-dimethyl-pyrrol-3-yl]-2-oxo-acetic acid (260 mg, 0.715 mmol), 3,3-difluoro-1-methylcyclobutanamine hydrochloride (140.8 mg, 0.89 mmol), HATU (339.7 mg, 0.89 mmol) in DMF (0.5 mL) and stirred 30 minutes at 65° C. The mixture was cooled and the solution was subjected to silica gel column chromatography using a gradient from 10 till 100% EtOAc in heptane and further by preparative HPLC (Stationary phase: RP) (Bridge Prep C18 OBD—10 μm, 30×150 mm, Mobile phase: 0.25% NH$_4$HCO$_3$ solution in water, CH$_3$CN) resulting in compound 47 (68 mg) as a white fluffy solid. LC method D; Rt: 5.74 min. m/z: 465.0 (M–H)– Exact mass: 466.1. $^1$H NMR (400 MHz, DMSO-d$_6$) δ ppm 1.51 (s, 3 H) 2.47 (s, 3 H) 2.59-2.76 (m, 2 H) 2.93-3.08 (m, 2 H) 3.66 (s, 3 H) 7.55 (t, J=9.1 Hz, 1 H) 7.95-8.04 (m, 1 H) 8.21 (dd, J=5.5, 2.4 Hz, 1 H) 9.13 (s, 1 H) 10.73 (s, 1 H). Differential scanning calorimetry: From 30 to 300° C. at 10° C./min: Peak: 168.1° C.

Compound 48: 4-[2-(tert-butylamino)-2-oxo-acetyl]-3-chloro-N-(3-cyano-4-fluoro-phenyl)-5-cyclopropyl-1-methyl-pyrrole-2-carboxamide

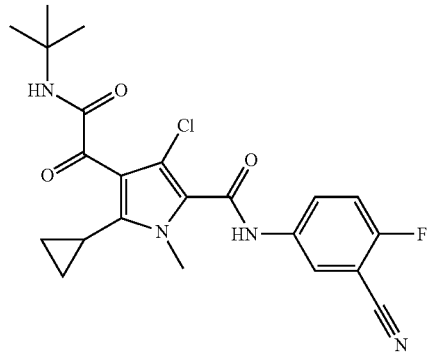 [SMILES: Cn1c(C(=O)Nc2ccc(F)c(C#N)c2)c(Cl)c(C(=O)C(=O)NC(C)(C)C)c1C1CC1]

Compound 48 (54 mg) was synthesized similarly as described for compound 31 using tert-Butylamine instead of (2R)-1,1,1-trifluoropropan-2-amine. LC method C; Rt: 2.04 min. m/z: 443.1 (M–H)$^-$ Exact mass: 444.1. $^1$H NMR (400 MHz, DMSO-d$_6$) δ ppm 0.47-0.57 (m, 2 H) 0.95-1.05 (m, 2 H) 1.35 (s, 9 H) 1.80-1.87 (m, 1 H) 3.76 (s, 3 H) 7.55 (t, J=9.13 Hz, 1 H) 7.93-8.02 (m, 1 H) 8.13 (s, 1 H) 8.20 (dd, J=5.72, 2.64 Hz, 1 H) 10.68 (s, 1 H). Differential scanning calorimetry: From 30 to 300° C. at 10° C./min: Peak: 198.8° C.

Compound 49: 4-[2-(tert-butylamino)-2-oxo-acetyl]-3-chloro-5-cyano-N-(3-cyano-4-fluoro-phenyl)-1-methyl-pyrrole-2-carboxamide

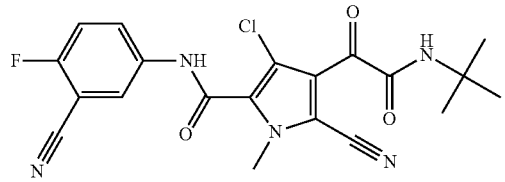 [SMILES: Cn1c(C#N)c(C(=O)C(=O)NC(C)(C)C)c(Cl)c1C(=O)Nc1ccc(F)c(C#N)c1]

A microwave vial was charged with compound 50 (100 mg, 0.207 mmol), copper (I) cyanide (27.8 mg, 0.31 mmol) in DMF (5.06 mL, 65.03 mmol). The vial was capped and irradiated at 160° C. for 30 minutes. The mixture was concentrated in vacuo. The residue was partioned between water and EtOAc. NH₄OH was added and the organic layer was separated, dried (MgSO₄), filtered and concentrated in vacuo. The obtained residue was purified using column chromatography on silica (gradient elution: ethyl acetate: heptane from 0 to 100%). The product fractions were collected and concentrated in vacuo. The product was triturated in DIPE, filtered off and dried under vacuum resulting in compound 49 (24 mg) as a pale yellow solid. LC method B; Rt: 1.05 min. m/z: 428.1 (M–H)⁻ Exact mass: 429.1. ¹H NMR (400 MHz, DMSO-d₆) δ ppm 1.32-1.38 (m, 9 H) 3.92 (s, 3 H) 7.60 (t, J=9.2 Hz, 1 H) 7.94-8.02 (m, 1 H) 8.21 (dd, J=5.9, 2.6 Hz, 1 H) 8.59 (s, 1 H) 11.16 (s, 1 H).

Synthesis of methyl 4-[2-(tert-butylamino)-2-oxo-acetyl]-3-chloro-1-methyl-pyrrole-2-carboxylate Et₃N (5.09 mL, 36.6 mmol) was added to a solution of 2-(4-chloro-5-methoxycarbonyl-1-methyl-pyrrol-3-yl)-2-oxo-acetic acid (3 g, 12.21 mmol), 2-methylpropan-2-amine (1.62 mL, 15.27 mmol), HATU (5.81 g, 15.27 mmol) in DMF (14.96 mL, 193.26 mmol) and stirred 30 minutes at 65° C. The solution was subjected to silica gel column chromatography using a gradient from 10 till 100% EtOAc in heptane. The product fractions were concentrated resulting in methyl 4-[2-(tert-butylamino)-2-oxo-acetyl]-3-chloro-1-methyl-pyrrole-2-carboxylate (3.2 g) as a clear oil, which solidified on standing. LC method B; Rt: 1.02 min. m/z: 299.1 (M–H)⁻ Exact mass: 300.1.

Compound 50: 5-bromo-4-[2-(tert-butylamino)-2-oxo-acetyl]-3-chloro-N-(3-cyano-4-fluoro-phenyl)-1-methyl-pyrrole-2-carboxamide

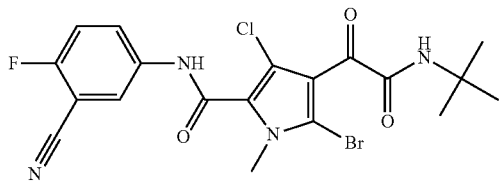 [SMILES: Cn1c(Br)c(C(=O)C(=O)NC(C)(C)C)c(Cl)c1C(=O)Nc1ccc(F)c(C#N)c1]

Compound 50 (500 mg) was synthesized similarly as described for compound 29 using methyl 4-[2-(tert-butylamino)-2-oxo-acetyl]-3-chloro-1-methyl-pyrrole-2-carboxylate instead of methyl 3-chloro-1-methyl-4-[2-oxo-2-[[(1R)-2,2,2-trifluoro-1-methyl-ethyl]-amino]acetyl] pyrrole-2-carboxylate. LC method B; Rt: 1.06 min. m/z: 481.0 (M–H)⁻ Exact mass: 482.0. ¹H NMR (400 MHz, DMSO-d₆) δ ppm 1.35 (s, 9 H) 3.75 (s, 3 H) 7.57 (t, J=9.13 Hz, 1 H) 7.94-8.03 (m, 1 H) 8.20 (dd, J=5.72, 2.64 Hz, 1 H) 8.38 (s, 1-H) 10.88 (s, 1 H). Differential scanning calorimetry: From 30 to 300° C. at 10° C./min: Peak: 204.4° C.

Compound 51: N-(3-cyano-4-fluoro-phenyl)-1-methyl-4-[2-oxo-2-[[(1S)-2,2,2-trifluoro-1-methyl-ethyl]amino]acetyl]pyrrole-2-carboxamide

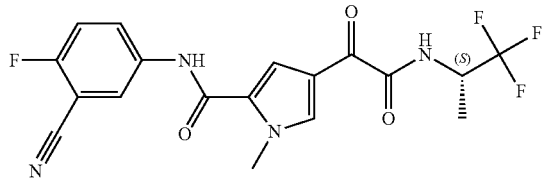

A solution of 2-(5-methoxycarbonyl-1-methyl-pyrrol-3-yl)-2-oxo-acetic acid (0.9 g, 3.45 mmol) in DMF (20 mL) was cooled to 5° C. in an ice water bath. Then DIPEA (1.8 mL, 10.36 mmol) and (S)-1,1,1-trifluoro-2-propylamine (468.5 mg, 4.14 mmol) were added and stirred in an ice water bath. A solution of HATU (1444 mg, 3.8 mmol) in DMF (10 mL) was added dropwise while cooling was continued. The obtained solution was stirred for 1 hour under cooling. The reaction was quenched with water (25 mL). A beige precipitation was formed which was collected on a filter and rinsed with water. Then it was dried in a vacuum oven at 55° C. for 24 hours resulting in methyl 1-methyl-4-[2-oxo-2-[[(1S)-2,2,2-trifluoro-1-methyl-ethyl]amino]acetyl]pyrrole-2-carboxylate (872 mg) as a beige solid. Methyl 1-methyl-4-[2-oxo-2-[[(1S)-2,2,2-trifluoro-1-methyl-ethyl]amino]acetyl]pyrrole-2-carboxylate (872 mg, 2.85-mmol) was dissolved in THF (20 mL), LiOH (272.8 mg, 11.39 mmol) in water (2 mL) was added. MeOH (2 mL) was added to dissolve all the reactants. The mixture was stirred overnight at room temperature and next concentrated in vacuo until only water remained. HCl (1M in H₂O) (11.4 mL, 1 M, 11.4 mmol) was added and this was extracted using Me-THF (3×10 mL). The combined extracts were washed with brine (20 mL), dried on Na₂SO₄, filtered, and concentrated in vacuo yielding 1-methyl-4-[2-oxo-2-[[(1S)-2,2,2-trifluoro-1-methyl-ethyl]amino]acetyl]pyrrole-2-carboxylic acid (823 mg) as a bright white powder. LC method B; Rt: 0.49 min. m/z: 291.0 (M–H)⁻ Exact mass: 292.1. 1-methyl-4-[2-oxo-2-[[(1S)-2,2,2-trifluoro-1-methyl-ethyl]amino]acetyl]-pyrrole-2-carboxylic acid (300 mg, 1.03 mmol) in DMF (1.6 mL) with DIPEA (0.53 mL, 3.08 mmol) was treated with HATU (429.4 mg, 1.13 mmol). The resulting mixture was stirred at room temperature for 30 minutes. Then 5-amino-2-fluorobenzonitrile (209.6 mg, 1.54 mmol) was added and the resulting mixture was stirred for 2 hours at room temperature. The mixture was injected as such on a silicaplug and purified using silica gel column chromatography (gradient elution: EtOAc-heptane 0:100 to 100:0). The desired fractions were concentrated under reduced pressure, resulting in compound 51 (260 mg). LC method B; Rt: 1.03 min. m/z: 409.1 (M–H)⁻ Exact mass: 410.1. ¹H NMR (400 MHz, DMSO-d₆) δ ppm 1.36 (d, J=7.0 Hz, 3 H), 3.97 (s, 3 H), 4.60-4.76 (m, 1 H), 7.53 (t, J=9.1 Hz, 1 H), 7.69 (d, J=1.8 Hz, 1 H), 8.03 (ddd, J=9.2, 4.9, 2.6 Hz, 1 H), 8.14 (d, J=1.3 Hz, 1 H), 8.23 (dd, J=5.8, 2.8 Hz, 1 H), 9.34 (d, J=8.1 Hz, 1 H), 10.42 (br. s., 1 H)

Compound 52: N-(3-cyano-4-fluoro-phenyl)-4-[2-(isopropylamino)-2-oxo-acetyl]-1,5-dimethyl-pyrrole-2-carboxamide

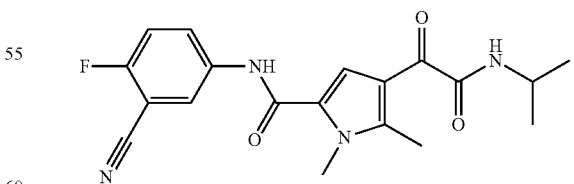

NaH (60% dispersion in mineral oil, 5875 mg, 147 mmol) was added portionwise to a solution of ethyl 5-methyl-1H-pyrrole-2-carboxylate (15000 mg, 97.92 mmol) and iodomethane (7.3 mL, 117.5 mmol) in DMF (40 mL). The reaction was stirred for 1 hour. HCl (1M in H₂O) (49.0 mL, 1 M, 49.0 mmol) was added. The resulting mixture was extracted using EtOAc (3×100 mL). The combined organics were washed with brine, dried on Na$_2$SO$_4$, filtered and concentrated in vacuo yielding crude ethyl 1,5-dimethylpyrrole-2-carboxylate (8.56 g) as a yellow powder which was used as such. Crude ethyl 1,5-dimethyl-pyrrole-2-carboxylate (8560 mg) was dissolved in THF (dried on molecular sieves) (144 mL) and 5-amino-2-fluorobenzonitrile (7666 mg, 56.3 mmol) was added. This mixture was cooled in an ice bath. Lithium bis(trimethylsilyl)amide (1M in toluene) (102.4 mL, 1 M) was added dropwise over a period of 10 minutes. The ice bath was removed and the mixture was stirred for 1 hour at room temperature. The mixture was quenched with saturated ammonium chloride (300 mL) and the resulting mixture was extracted using EtOAc (3×150 mL). The combined extracts were washed with brine (200 mL), dried on Na$_2$SO$_4$, filtered and concentrated in vacuo. The obtained residue was purified by column chromatography using gradient elution from heptane to EtOAc (100:0 to 0:100). The desired fractions were collected and concentrated in vacuo yielding N-(3-cyano-4-fluoro-phenyl)-1,5-dimethyl-pyrrole-2-carboxamide (10.2 g) as a slightly yellow powder which was used as such. LC method B; Rt: 0.98 min. m/z: 256.1 (M–H)$^-$ Exact mass: 257.1. N-(3-cyano-4-fluorophenyl)-1,5-dimethyl-pyrrole-2-carboxamide (5000 mg, 19.44 mmol) was dissolved in DCM (50 mL) and cooled on ice under nitrogen. A solution of ethyl 2-chloro-2-oxoacetate (3.3 mL) in DCM (10 mL) was added dropwise and the mixture was stirred for 15 minutes. AlCl$_3$ (5183 mg, 38.9 mmol) was added in portions. The mixture was stirred at 0° C. under N$_2$ for 5 hours. The mixture was diluted with Me-THF (200 mL) and this was added dropwise into ice water (500 mL). This mixture was extracted with EtOAc (3×150 mL). The combined organic layers were washed with water and brine, dried (Na$_2$SO$_4$) and evaporated to dryness, resulting in crude ethyl 2-[5-[(3-cyano-4-fluorophenyl)carbamoyl]-1,2-dimethyl-pyrrol-3-yl]-2-oxo-acetate (9.4 g) as a yellow powder which was used as such. LC method B; Rt: 1.04 min. m/z: 356.1 (M–H)$^-$ Exact mass: 357.1. Crude ethyl 2-[5-[(3-cyano-4-fluoro-phenyl)carbamoyl]-1,2-dimethyl-pyrrol-3-yl]-2-oxo-acetate (9.4 g, 26.4 mmol) was dissolved in THF (200 mL) and to this was added NaOH (1M in H$_2$O, 39.6 mL). The resulting mixture was stirred at room temperature for 30 minutes and next concentrated in vacuo until only water remained. Then HCl (aq/1M/40 mL) was added and this was extracted using Me-THF (3×100 mL). The combined extracts were washed with brine, dried on Na$_2$SO$_4$, filtered and concentrated in vacuo, resulting in crude 2-[5-[(3-cyano-4-fluoro-phenyl) carbamoyl]-1,2-dimethyl-pyrrol-3-yl]-2-oxo-acetic acid (8.02 g) as a yellow solid which was used as such. LC method B; Rt: 0.58 min. m/z: 328.0 (M–H)$^-$ Exact mass: 329.1. Crude 2-[5-[(3-cyano-4-fluoro-phenyl)carbamoyl]-1, 2-dimethyl-pyrrol-3-yl]-2-oxo-acetic acid (100 mg) in DMF (0.5 mL) with DIPEA (0.13 mL, 0.77 mmol) was treated with HATU (106.7 mg, 0.28 mmol). The resulting mixture was stirred at room temperature for 30 minutes. Then isopropylamine (18.09 mg, 0.31 mmol) was added and the resulting mixture was stirred for 2 hours at room temperature and next at 50° C. for 2 hours. The mixture was injected as such on a silicaplug and purified using silica gel column chromatography (gradient elution: EtOAc-heptane 0:100 to 100:0). And further by Preparative HPLC (RP SunFire Prep C18 OBD—10 µm, 30×150 mm). Mobile phase (0.25% NH$_4$HCO$_3$ solution in water, MeOH). The desired fractions were concentrated under reduced pressure and co-evaporated twice (2×15 mL MeOH) and the residue was dried in a vacuum oven at 55° C. for 18 hours resulting in compound 52 as an off white solid. LC method B; Rt: 0.99 min. m/z: 369.1 (M–H)$^-$ Exact mass: 370.1. $^1$H NMR (400 MHz, DMSO-d$_6$) δ ppm 1.15 (d, J=6.6 Hz, 6 H), 2.57 (s, 3 H), 3.84 (s, 3 H), 3.91-4.10 (m, 1 H), 7.52 (t, J=9.1 Hz, 1 H), 7.72 (s, 1 H), 8.02 (ddd, J=9.2, 5.0, 2.8 Hz, 1 H), 8.22 (dd, J=5.7, 2.6 Hz, 1 H), 8.51 (d, J=7.9 Hz, 1 H), 10.42 (s, 1 H).

Compound 53: N-(3-cyano-4-fluoro-phenyl)-1,5-dimethyl-4-[2-[[(1R)-1-methylpropyl]-amino]-2-oxo-acetyl]pyrrole-2-carboxamide

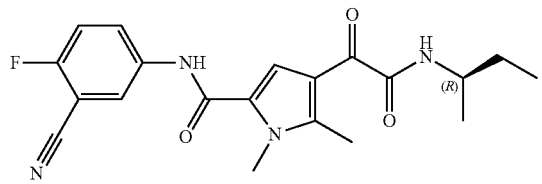

Compound 53 was prepared similarly as described for compound 52, using (R)-(–)-2-aminobutane instead of isopropylamine. LC method B; Rt: 1.06 min. m/z: 383.1 (M–H)$^-$ Exact mass: 384.2. $^1$H NMR (400 MHz, DMSO-d$_6$) δ 0.86 (t, J=7.3 Hz, 3 H), 1.12 (d, J=6.6 Hz, 3 H), 1.42-1.57 (m, 2 H), 2.57 (s, 3 H), 3.73-3.87 (m, 4 H), 7.52 (t, J=9.2 Hz, 1 H), 7.73 (s, 1 H), 8.02 (ddd, J=9.2, 5.0, 2.8 Hz, 1 H), 8.22 (dd, J=5.7, 2.6 Hz, 1 H), 8.45 (d, J=8.4 Hz, 1 H), 10.43 (s, 1 H).

Synthesis of (2R)-3,3-difluorobutan-2-amine (R)-2-((tert-butoxycarbonyl)amino)propanoic acid (30 g, 159 mmol), N,O-dimethyl-hydroxylamine hydrochloride (17.5 g, 178 mmol), HATU (74 g, 195 mmol) and N,N-diisopropylethylamine (30 g, 232 mmol) were dissolved in DMF (300 mL) and stirred at room temperature for 15 hours. The reaction mixture was concentrated under vacuum and the residue was dissolved in CH$_2$Cl$_2$ (500 mL) and washed with brine (3×200 mL). The organic layer was dried over Na$_2$SO$_4$ and concentrated in vacuo. The residue was purified via silica gel chromatography using petroleum ether: EtOAc 2:1 as eluent yielding tert-butyl N-[(1R)-2-[methoxy (methyl)amino]-1-methyl-2-oxo-ethyl]carbamate (28.9 g). Tert-butyl N-[(1R)-2-[methoxy(methyl)amino]-1-methyl-2-oxo-ethyl]carbamate was dissolved in THF (300 mL) and cooled to 0° C. Methylmagnesium bromide 3.0 m in diethyl ether (85 mL, 255 mmol) was added dropwise and the reaction mixture was stirred 15 hours at room temperature. The reaction mixture was quenched with sat. NH$_4$Cl and extracted with CH$_2$Cl$_2$ (3×100 mL). The combined organic layers were dried over Na$_2$SO$_4$, filtered and evaporated to dryness. The obtained residue was purified via silica gel chromatography yielding tert-butyl N-[(1R)-1-methyl-2-oxo-propyl]carbamate (18.9 g). To a cooled (−78° C.) solution of tert-butyl N-[(1R)-1-methyl-2-oxo-propyl]carbamate (10 g, 53.4 mmol) in CH$_2$Cl$_2$ (200 mL) bis(2-methoxyethyl) aminosulfur trifluoride (18.9 g, 117.5 mmol) was added dropwise and stirring was continued for 2 hours at −78° C. The reaction mixture was allowed to warm to room temperature and stirred overnight. The reaction mixture was quenched with sat. NaHCO$_3$ and extracted with EtOAc. The combined organic layers were washed with brine, dried over MgSO$_4$, filtered and evaporated to dryness. The residue was purified by silica gel chromatography using a gradient from petroleum ether to petroleum ether:EtOAc 1:1 yielding tert-butyl N-[(1R)-2,2-difluoro-1-methyl-propyl]carbamate (6.77 g). Tert-butyl N-[(1R)-2,2-difluoro-1-methyl-propyl] carbamate (6.77 g) was dissolved in EtOAc (50 mL). HCl in EtOAc was added at 0° C. and the reaction mixture was stirred for 4 hours at room temperature. The formed precipitate was filtered off and dried under high vacuum yielding (2R)-3,3-difluorobutan-2-amine hydrochloride (3.5 g).

Compound 54: N-(3-cyano-4-fluoro-phenyl)-4-[2-[[(1R)-2,2-difluoro-1-methyl-propyl]-amino]-2-oxo-acetyl]-1,5-dimethyl-pyrrole-2-carboxamide

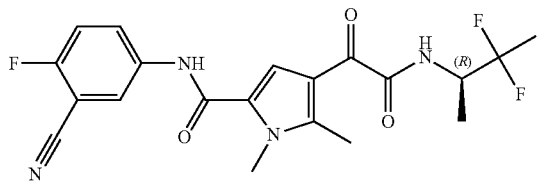

A vial was loaded with crude 2-[5-[(3-cyano-4-fluoro-phenyl)carbamoyl]-1,2-dimethyl-pyrrol-3-yl]-2-oxo-acetic acid (250 mg,), HATU (266.74 mg, 0.7 mmol), (2R)-3,3-difluoro-butan-2-amine hydrochloride (0.77 mmol) and DMF (1 mL). This mixture was heated and stirred at 65° C. Then DIPEA (0.33 mL, 1.91 mmol) was added and the mixture was stirred for 20 minutes. The mixture was cooled to room temperature and injected directly onto a silica plug and purified using silica gel column chromatography (gradient elution: EtOAc-heptane 0:100 to 100:0). The desired fractions were concentrated under reduced pressure and dried in a vacuum oven at 55° C. for 18 hours. The obtained solids was crystallised out of iPrOH. The crystals were collected on a filter and dried in a vacuum oven at 55° C. for 18 hours yielding compound 54 (124 mg) as white powder. LC method B; Rt: 1.06 min. m/z: 419.1 (M−H)⁻ Exact mass: 420.1. ¹H NMR (400 MHz, DMSO-d₆) δ ppm 1.23 (d, J=6.8 Hz, 3 H), 1.62 (t, J=19.3 Hz, 3 H), 2.58 (s, 3 H), 3.85 (s, 3 H), 4.28-4.43 (m, 1 H), 7.52 (t, J=9.1 Hz, 1 H), 7.65 (s, 1 H), 7.98-8.05 (m, 1 H), 8.21 (dd, J=5.7, 2.6 Hz, 1 H), 8.92 (d, J=9.2 Hz, 1 H), 10.44 (s, 1 H).

Synthesis of (2S)-3,3-difluorobutan-2-amine hydrochloride (S)-2-((tert-butoxycarbonyl)amino)propanoic acid (39 g, 206 mmol), N,O-dimethyl-hydroxylamine hydrochloride (24 g, 246 mmol), HATU (117 g, 308 mmol) and N,N-diisopropylethylamine (66.3 g, 513 mmol) were dissolved in DMF (500 mL) and stirred at room temperature for 16 hours. The reaction mixture was poured into water (500 mL) and the formed precipitate was filtered off. The filter cake was washed with water (1 L) and dried to give tert-butyl N-[(1S)-2-[methoxy(methyl)amino]-1-methyl-2-oxo-ethyl]carbamate (36 g) as a white powder. tert-butyl N-[(1S)-2-[methoxy(methyl)amino]-1-methyl-2-oxo-ethyl]carbamate (35 g, 151 mmol) was dissolved in THF (500 mL) and cooled to 0° C. Methylmagnesium bromide (3.0 M in diethyl ether, 140 mL) was added and the reaction mixture was stirred 16 hours at room temperature. The reaction mixture was poured into water (100 mL) and evaporated to dryness. The residue was dissolved in EtOAc, washed with water, dried over Na₂SO₄, filtered and evaporated to dryness yielding tert-butyl N-[(1S)-1-methyl-2-oxo-propyl]carbamate (22 g) as a white powder. To a cooled (−78° C.) solution of tert-butyl N-[(1S)-1-methyl-2-oxo-propyl]carbamate (12 g, 64.1 mmol) in CH₂Cl₂ (200 mL) bis(2-methoxyethyl)aminosulfur trifluoride (18.9 g, 117.5 mmol) was added. The reaction mixture was allowed to warm to room temperature and stirred overnight. The reaction mixture was poured into water and extracted with CH₂Cl₂. The organic layer was washed with water, dried over Na₂SO₄, filtered and evaporated to dryness. The obtained residue was purified by silica gel chromatography yielding tert-butyl N-[(1S)-2,2-difluoro-1-methyl-propyl]carbamate (5.8 g) as a pale yellow solid. Tert-butyl N-[(1S)-2,2-difluoro-1-methyl-propyl]carbamate (5.8 g, 27.7 mmol) was dissolved in EtOAc (100 mL). HCl (g) was bubbled through for 30 minutes and then the volatiles were removed under reduced pressure yielding (2S)-3,3-difluorobutan-2-amine hydrochloride (3.8 g) ¹H NMR (400 MHz, DMSO-d₆) δ ppm 8.69 (br. s., 3H), 3.76-3.63 (m, 1H), 1.72 (t, J=19.7 Hz, 3H), 1.28 (d, J=6.8 Hz, 3H).

Compound 55: N-(3-cyano-4-fluoro-phenyl)-4-[2-[[(1S)-2,2-difluoro-1-methyl-propyl]-amino]-2-oxo-acetyl]-1,5-dimethyl-pyrrole-2-carboxamide

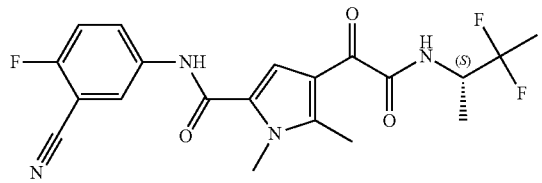

Compound 55 (130 mg) was prepared similarly as described for compound 54, using (2S)-3,3-difluorobutan-2-amine hydrochloride instead of (2R)-3,3-difluorobutan-2-amine hydrochloride. LC method B; Rt: 1.06 min. m/z: 419.1 (M−H)⁻ Exact mass: 420.1. ¹H NMR (400 MHz, DMSO-d₆) δ ppm 1.23 (d, J=6.8 Hz, 3 H), 1.62 (t, J=19.3 Hz, 3 H), 2.58 (s, 3 H), 3.85 (s, 3 H), 4.28-4.44 (m, 1 H), 7.52 (t, J=9.1 Hz, 1 H), 7.65 (s, 1 H), 7.98-8.05 (m, 1 H), 8.21 (dd, J=5.7, 2.6 Hz, 1 H), 8.92 (d, J=9.2 Hz, 1 H), 10.44 (s, 1 H).

Compound 56: N-(3-cyano-4-fluoro-phenyl)-4-[2-[(3,3-difluoro-1-methyl-cyclobutyl)-amino]-2-oxo-acetyl]-1,5-dimethyl-pyrrole-2-carboxamide

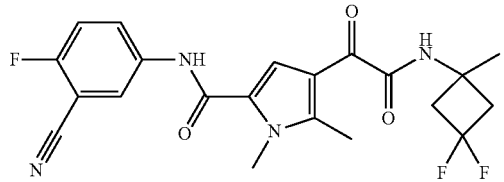 [SMILES: Cc1c(C(=O)C(=O)NC2(C)CC(F)(F)C2)cc(C(=O)Nc2ccc(F)c(C#N)c2)n1C]

Compound 56 (147 mg) was prepared similarly as described for compound 54, using 3,3-difluoro-1-methyl-cyclobutanamine hydrochloride instead of (2R)-3,3-difluorobutan-2-amine hydrochloride. LC method B; Rt: 1.08 min. m/z: 431.1 (M−H)⁻ Exact mass: 432.1. ¹H NMR (400 MHz, DMSO-d₆) δ ppm 1.52 (s, 3 H), 2.58 (s, 3 H), 2.61-2.77 (m, 2 H), 2.91-3.13 (m, 2 H), 3.85 (s, 3 H), 7.52 (t, J=9.1 Hz, 1

H), 7.73 (s, 1 H), 7.99-8.06 (m, 1 H), 8.22 (dd, J=5.8, 2.8 Hz, 1 H), 9.10 (s, 1 H), 10.45 (s, 1 H).

Compound 57: N-(3-cyano-4-fluoro-phenyl)-1,5-dimethyl-4-[2-oxo-2-[[1-(trifluoromethyl)-cyclopropyl]amino]acetyl]pyrrole-2-carboxamide

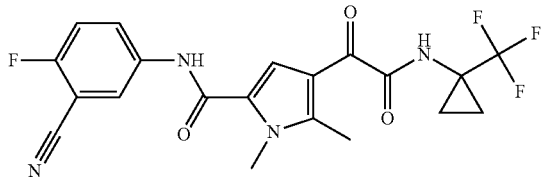 [SMILES: Cc1c(C(=O)C(=O)NC2(C(F)(F)F)CC2)cc(C(=O)Nc2ccc(F)c(C#N)c2)n1C]

Compound 57 (138 mg) was prepared similarly as described for compound 54, using 1-trifluoromethyl-1-cyclopropylamine instead of (2R)-3,3-difluorobutan-2-amine hydrochloride. LC method B; Rt: 1.07 min. m/z: 435.1 (M–H)⁻ Exact mass: 436.1. ¹H NMR (400 MHz, DMSO-d₆) δ ppm 1.09-1.19 (m, 2 H), 1.28-1.36 (m, 2 H), 2.56 (s, 3 H), 3.84 (s, 3 H), 7.52 (t, J=9.1 Hz, 1 H), 7.68 (s, 1 H), 7.97-8.06 (m, 1 H), 8.21 (dd, J=5.7, 2.6 Hz, 1 H), 9.49 (s, 1 H), 10.46 (s, 1 H).

Compound 58: N-(3-cyano-4-fluoro-phenyl)-1,5-dimethyl-4-[2-oxo-2-[(2,2,2-trifluoro-1,1-dimethyl-ethyl)amino]acetyl]pyrrole-2-carboxamide

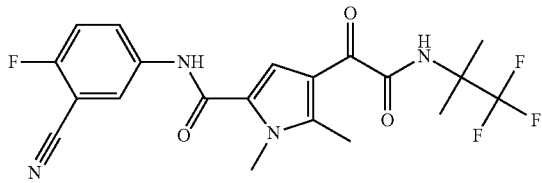 [SMILES: Cc1c(C(=O)C(=O)NC(C)(C)C(F)(F)F)cc(C(=O)Nc2ccc(F)c(C#N)c2)n1C]

Compound 58 (129 mg) was prepared similarly as described for compound 54, using 2,2,2-trifluoro-1,1-dimethyl-ethylamine instead of (2R)-3,3-difluorobutan-2-amine hydrochloride. LC method B; Rt: 1.14 min. m/z: 437.1 (M–H)⁻ Exact mass: 438.1. ¹H NMR (400 MHz, DMSO-d₆) δ ppm 1.60 (s, 6 H), 2.56 (s, 3 H), 3.84 (s, 3 H), 7.48-7.57 (m, 2 H), 8.02 (s, 1 H), 8.21 (dd, J=5.8, 2.8 Hz, 1 H), 8.62 (s, 1 H), 10.48 (s, 1 H)

Compound 59: 4-[2-(tert-butylamino)-2-oxo-acetyl]-N-(3-cyano-4-fluoro-phenyl)-1,5-dimethyl-pyrrole-2-carboxamide

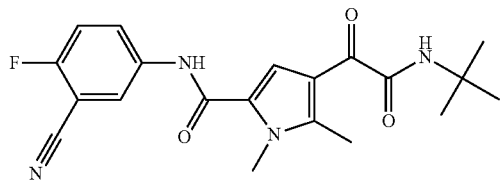 [SMILES: Cc1c(C(=O)C(=O)NC(C)(C)C)cc(C(=O)Nc2ccc(F)c(C#N)c2)n1C]

Compound 59 (54 mg) was prepared similarly as described for compound 54, using tert-butylamine instead of (2R)-3,3-difluorobutan-2-amine hydrochloride. LC method B; Rt: 1.10 min. m/z: 383.1 (M–H)⁻ Exact mass: 384.2. ¹H NMR (400 MHz, DMSO-d₆) δ ppm 1.36 (s, 9 H), 2.56 (s, 3 H), 3.84 (s, 3 H), 7.52 (t, J=9.1 Hz, 1 H), 7.65 (s, 1 H), 7.98-8.05 (m, 1 H), 8.08 (s, 1 H), 8.22 (dd, J=5.7, 2.6 Hz, 1 H), 10.46 (s, 1 H)

Compound 60: N-(3-cyano-4-fluoro-phenyl)-1,5-dimethyl-4-[2-[(3-methyloxetan-3-yl)-amino]-2-oxo-acetyl]pyrrole-2-carboxamide

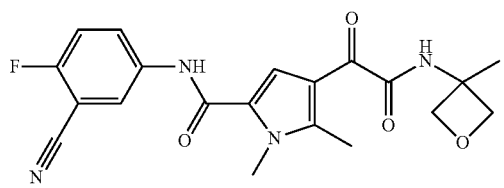 [SMILES: Cc1c(C(=O)C(=O)NC2(C)COC2)cc(C(=O)Nc2ccc(F)c(C#N)c2)n1C]

Compound 60 (149 mg) was prepared similarly as described for compound 54, using 3-methyl-3-oxetanamine instead of (2R)-3,3-difluorobutan-2-amine hydrochloride. LC method B; Rt: 0.90 min. m/z: 397.1 (M–H)⁻ Exact mass: 398.1. ¹H NMR (400 MHz, DMSO-d₆) δ ppm 1.59 (s, 3 H), 2.58 (s, 3 H), 3.85 (s, 3 H), 4.37 (d, J=6.6 Hz, 2 H), 4.72 (d, J=6.4 Hz, 2 H), 7.52 (t, J=9.1 Hz, 1 H), 7.77 (s, 1 H), 7.98-8.06 (m, 1 H), 8.21 (dd, J=5.8, 2.8 Hz, 1 H), 9.22 (s, 1 H), 10.45 (s, 1 H).

Compound 61: N-(3-cyano-4-fluoro-phenyl)-5-cyclopropyl-1-methyl-4-[2-oxo-2-[[(1R)-2,2,2-trifluoro-1-methyl-ethyl]amino]acetyl]pyrrole-2-carboxamide

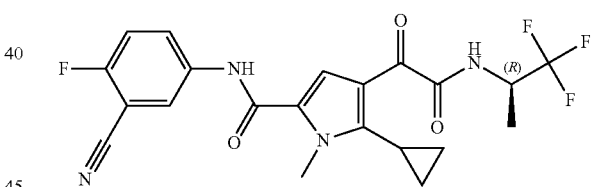

A microwave vial was charged with compound 25 (100 mg, 0.2 mmol), potassium cyclo-propyltrifluoroborate (45 mg, 0.31 mmol), Cs₂CO₃ (133 mg, 0.41 mmol), DME (2.3 mL) and water (0.23 mL). The mixture was purged with N₂ for 5 minutes.

Tetrakis(triphenylphosphine)palladium(0) (47.24 mg, 0.041 mmol) was added and the vial was capped. The mixture was stirred at 110° C. for 16 hours. The mixture was cooled and the residue partioned between sat. NH₄Cl-sol and Me-THF. The organic layer was separated, dried (MgSO₄), filtered and concentrated in vacuo. The crude was purified using silica gel column chromatography (gradient elution: EtOAc-heptane 0:100 to 100:0) and further by preparative HPLC (RP SunFire Prep C18 OBD—10 μm, 30×150 mm). Mobile phase (0.25% NH₄HCO₃ solution in water, MeOH), compound 61 (16 mg) as a white powder.

LC method B; Rt: 1.11 min. m/z: 449.1 (M–H)⁻ Exact mass: 450.1. ¹H NMR (400 MHz, DMSO-d₆) δ ppm 0.61-0.70 (m, 2 H), 1.02-1.13 (m, 2 H), 1.34 (d, J=7.0 Hz, 3 H), 1.76-1.90 (m, 1 H), 3.96 (s, 3 H), 4.70 (dq, J=15.5, 7.7 Hz, 1 H), 7.52 (t, J=9.2 Hz, 1 H), 7.56 (s, 1 H), 7.96-8.06 (m, 1 H), 8.21 (dd, J=5.8, 2.8 Hz, 1 H), 9.25 (d, J=8.8 Hz, 1 H), 10.42 (s, 1 H).

Compound 62, 63, 65 to 72 and 74 to 82 were prepared similarly as described for compound 73, using the corresponding amine instead of (1-aminocyclopropyl)methanol.

Compound 62: N-(3-cyano-4-fluoro-phenyl)-4-[2-[[(3R,4S)-3-hydroxy-1-methyl-4-piperidyl]amino]-2-oxo-acetyl]-1,5-dimethyl-pyrrole-2-carboxamide

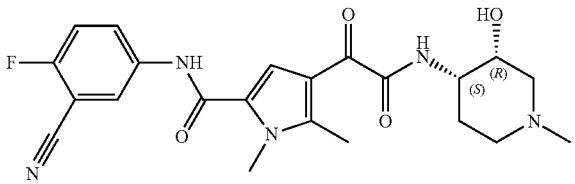

(3R,4S)-4-amino-1-methylpiperidin-3-ol was used as amine, resulting in compound 62 (40.3 mg). ¹H NMR (400 MHz, DMSO-d₆) δ ppm 1.46-1.65 (m, 1 H), 1.79-1.93 (m, 1 H), 1.98-2.09 (m, 1 H), 2.12-2.25 (m, 4 H), 2.54-2.70 (m, 5 H), 3.69-3.80 (m, 2 H), 3.84 (s, 3 H), 4.60-4.88 (m, 1 H), 7.52 (t, J=9.2 Hz, 1 H), 7.82 (s, 1 H), 7.98-8.09 (m, 2 H), 8.22 (dd, J=5.7, 2.6 Hz, 1 H), 10.43 (s, 1 H). LC method B; Rt: 0.74 min. m/z: 440.2 (M–H)⁻ Exact mass: 441.2.

Compound 63: N-(3-cyano-4-fluoro-phenyl)-4-[2-[[(1S)-1-(hydroxymethyl)pentyl]amino]-2-oxo-acetyl]-1,5-dimethyl-pyrrole-2-carboxamide

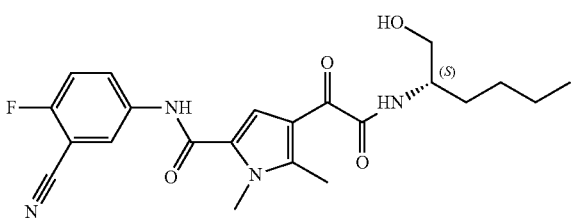

(S)-(+)-2-amino-1-hexanol was used as amine, resulting in compound 63 (33.7 mg). ¹H NMR (400 MHz, DMSO-d₆) δ ppm 0.80-0.91 (m, 3 H), 1.19-1.47 (m, 5 H), 1.50-1.69 (m, 1 H), 2.57 (s, 3 H), 3.34-3.52 (m, 2 H), 3.73-3.91 (m, 4 H), 4.64-4.81 (m, 1 H), 7.52 (t, J=9.1 Hz, 1 H), 7.77 (s, 1 H), 8.03 (ddd, J=9.2, 4.8, 2.6 Hz, 1 H), 8.22 (dd, J=5.7, 2.6 Hz, 1 H), 8.29 (d, J=9.0 Hz, 1 H), 10.47 (s, 1 H). LC method C; Rt: 1.89 min. m/z: 427.3 (M–H)⁻ Exact mass: 428.2.

Compound 65: N-(3-cyano-4-fluoro-phenyl)-4-[2-[[(1S,2S)-2-hydroxycyclopentyl]amino]-2-oxo-acetyl]-1,5-dimethyl-pyrrole-2-carboxamide

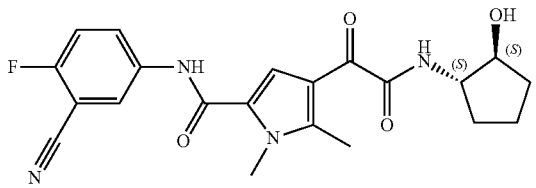

(1S,2S)-trans-2-aminocyclopentanol hydrochloride was used as amine, resulting in compound 65 (27.1 mg). ¹H NMR (400 MHz, DMSO-d₆) δ ppm 1.40-1.53 (m, 2 H), 1.55-1.73 (m, 2 H), 1.75-1.90 (m, 1 H), 1.92-2.05 (m, 1 H), 2.57 (s, 3 H), 3.84 (s, 3 H), 3.87-4.00 (m, 2 H), 4.78 (d, J=4.0 Hz, 1 H), 7.52 (t, J=9.1 Hz, 1 H), 7.71 (s, 1 H), 8.02 (ddd, J=9.2, 4.9, 2.6 Hz, 1 H), 8.22 (dd, J=5.7, 2.6 Hz, 1 H), 8.54 (d, J=7.5 Hz, 1 H), 10.45 (s, 1 H). LC method C; Rt: 1.74 min. m/z: 411.4 (M–H)⁻ Exact mass: 412.2.

Compound 66: N-(3-cyano-4-fluoro-phenyl)-4-[2-[[(1S,2R,5R)-2-hydroxy-5-methyl-cyclopentyl]amino]-2-oxo-acetyl]-1,5-dimethyl-pyrrole-2-carboxamide

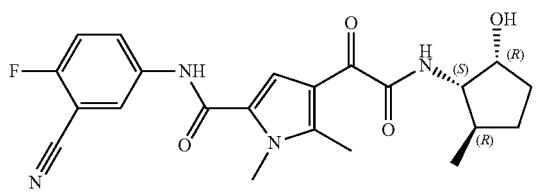

(1R,2S,3R)-2-amino-3-methyl-cyclopentanol hydrochloride was used as amine, resulting in compound 66 (38.2 mg). ¹H NMR (400 MHz, DMSO-d₆) δ ppm 0.98 (d, J=6.6 Hz, 3 H), 1.05-1.32 (m, 2 H), 1.48-1.62 (m, 1 H), 1.82-2.09 (m, 3 H), 2.58 (s, 3 H), 3.50-3.60 (m, 1 H), 3.85 (s, 3 H), 4.89 (d, J=4.2 Hz, 1 H), 7.52 (t, J=9.1 Hz, 1 H), 7.92 (s, 1 H), 7.96-8.06 (m, 2 H), 8.22 (dd, J=5.8, 2.8 Hz, 1 H), 10.46 (s, 1 H). LC method B; Rt: 0.94 min. m/z: 425.1 (M–H)⁻ Exact mass: 426.2.

Compound 67: N-(3-cyano-4-fluoro-phenyl)-4-[2-[[(1S,2S)-2-hydroxycyclohexyl]amino]-2-oxo-acetyl]-1,5-dimethyl-pyrrole-2-carboxamide

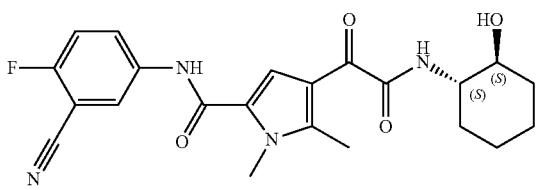

Trans-(1S,2S)-2-aminocyclohexanol hydrochloride was used as amine, resulting in compound 67 (42.5 mg). ¹H NMR (400 MHz, DMSO-d₆) δ ppm 1.19-1.35 (m, 4 H), 1.51-1.71 (m, 2 H), 1.78-1.94 (m, 2 H), 2.57 (s, 3 H), 3.35-3.58 (m, 2 H), 3.84 (s, 3 H), 4.64 (d, J=4.8 Hz, 1 H), 7.52 (t, J=9.1 Hz, 1 H), 7.79 (s, 1 H), 8.02 (ddd, J=9.2, 4.9, 2.6 Hz, 1 H), 8.22 (dd, J=5.9, 2.6 Hz, 1 H), 8.36 (d, J=8.4 Hz, 1 H), 10.45 (s, 1 H). LC method C; Rt: 1.78 min. m/z: 425.2 (M–H)⁻ Exact mass: 426.2.

Compound 68: N-(3-cyano-4-fluoro-phenyl)-4-[2-[[(1S)-1-(hydroxymethyl)-2-methyl-propyl]amino]-2-oxo-acetyl]-1,5-dimethyl-pyrrole-2-carboxamide

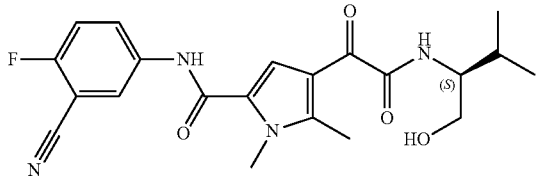

(S)-(+)-2-amino-3-methyl-1-butanol was used as amine, resulting in compound 68 (43.9 mg). $^1$H NMR (400 MHz, DMSO-d$_6$) δ ppm 0.80-0.95 (m, 6 H), 1.83-1.95 (m, 1 H), 2.58 (s, 3 H), 3.49 (t, J=5.2 Hz, 2 H), 3.63-3.74 (m, 1 H), 3.84 (s, 3 H), 4.64 (t, J=5.2 Hz, 1 H), 7.52 (t, J=9.1 Hz, 1 H), 7.78 (s, 1 H), 8.02 (ddd, J=9.2, 4.8, 2.9 Hz, 1 H), 8.18-8.26 (m, 2 H), 10.46 (s, 1 H). LC method B; Rt: 0.90 min. m/z: 413.2 (M–H)$^-$ Exact mass: 414.2.

Compound 69: N-(3-cyano-4-fluoro-phenyl)-4-[2-[[(1S,2S)-1-(hydroxymethyl)-2-methyl-butyl]amino]-2-oxo-acetyl]-1,5-dimethyl-pyrrole-2-carboxamide

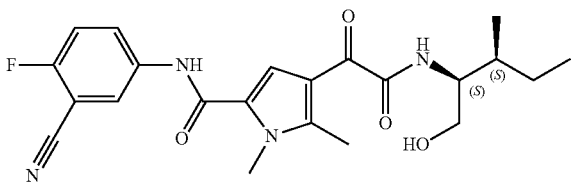

L-isoleucinol was used as amine, resulting in compound 69 (34.8 mg). $^1$H NMR (400 MHz, DMSO-d$_6$) δ ppm 0.81-0.91 (m, 6 H), 1.02-1.15 (m, 1 H), 1.33-1.54 (m, 1 H), 1.55-1.76 (m, 1 H), 2.55-2.61 (m, 3 H), 3.45-3.57 (m, 2 H), 3.68-3.79 (m, 1 H), 3.84 (s, 3 H), 4.53-4.69 (m, 1 H), 7.52 (t, J=9.1 Hz, 1 H), 7.79 (s, 1 H), 8.03 (ddd, J=9.2, 5.0, 2.8 Hz, 1 H), 8.17-8.29 (m, 2 H), 10.47 (s, 1 H). LC method C; Rt: 1.88 min. m/z: 427.3 (M–H)$^-$ Exact mass: 428.2.

Compound 70: N-(3-cyano-4-fluoro-phenyl)-4-[2-[[3-hydroxy-1-(methoxymethyl)-1-methyl-propyl]amino]-2-oxo-acetyl]-1,5-dimethyl-pyrrole-2-carboxamide

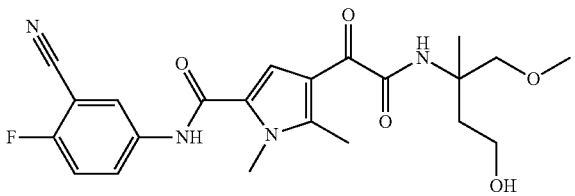 [SMILES: COCC(C)(CCO)NC(=O)C(=O)c1cc(C(=O)Nc2ccc(F)c(C#N)c2)n(C)c1C]

3-amino-4-methoxy-3-methylbutan-1-ol was used as amine, resulting in compound 70 (13.5 mg). $^1$H NMR (400 MHz, DMSO-d$_6$) δ ppm 1.35 (s, 3 H), 1.72-1.83 (m, 1 H), 1.92-2.04 (m, 1 H), 2.56 (s, 3 H), 3.28 (s, 3 H), 3.54 (q, J=9.1 Hz, 4 H), 3.83 (s, 3 H), 4.54-4.70 (m, 1 H), 7.52 (t, J=9.1 Hz, 1 H), 7.80 (s, 1 H), 8.03 (ddd, J=9.2, 4.9, 2.9 Hz, 1 H), 8.18-8.27 (m, 2 H), 10.48 (s, 1 H). LC method B; Rt: 0.92 min. m/z: 443.1 (M–H)$^-$ Exact mass: 444.2.

Compound 71: N-(3-cyano-4-fluoro-phenyl)-4-[2-[[3-(hydroxymethyl)oxetan-3-yl]amino]-2-oxo-acetyl]-1,5-dimethyl-pyrrole-2-carboxamide

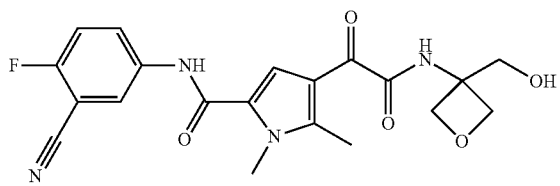 [SMILES: Cc1c(C(=O)C(=O)NC2(CO)COC2)cc(C(=O)Nc2ccc(F)c(C#N)c2)n1C]

(3-aminooxetan-3-yl)methanol was used as amine, resulting in compound 71 (36.4 mg). $^1$H NMR (400 MHz, DMSO-d$_6$) δ ppm 2.58 (s, 3 H), 3.66-3.74 (m, 2 H), 3.85 (s, 3 H), 4.54 (d, J=6.6 Hz, 2 H), 4.66 (d, J=6.6 Hz, 2 H), 5.14-5.31 (m, 1 H), 7.52 (t, J=9.1 Hz, 1 H), 7.77 (s, 1 H), 7.98-8.07 (m, 1 H), 8.22 (dd, J=5.6, 2.5 Hz, 1 H), 9.12 (s, 1 H), 10.46 (s, 1 H). LC method B; Rt: 0.78 min. m/z: 413.1 (M–H)$^-$ Exact mass: 414.1.

Compound 72: N-(3-cyano-4-fluoro-phenyl)-4-[2-[(2-hydroxy-1,2-dimethyl-propyl)amino]-2-oxo-acetyl]-1,5-dimethyl-pyrrole-2-carboxamide

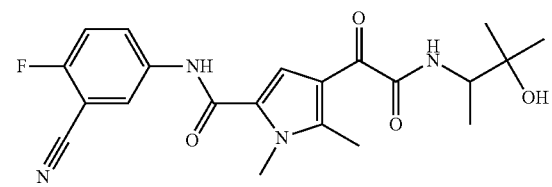 [SMILES: Cc1c(C(=O)C(=O)NC(C)C(C)(C)O)cc(C(=O)Nc2ccc(F)c(C#N)c2)n1C]

3-amino-2-methylbutan-2-ol was used as amine, resulting in compound 72 (6.3 mg). $^1$H NMR (400 MHz, DMSO-d$_6$) δ ppm 1.08 (s, 3 H), 1.09-1.15 (m, 6 H), 2.56-2.60 (m, 3 H), 3.75-3.89 (m, 4 H), 4.51 (s, 1 H), 7.52 (t, J=9.1 Hz, 1 H), 7.79 (s, 1 H), 8.02 (ddd, J=9.2, 5.0, 2.8 Hz, 1 H), 8.13 (d, J=9.5 Hz, 1 H), 8.20-8.24 (m, 1 H), 10.45 (s, 1 H). LC method C; Rt: 1.78 min. m/z: 413.4 (M–H)$^-$ Exact mass: 414.2.

Compound 73: N-(3-cyano-4-fluoro-phenyl)-4-[2-[[1-(hydroxymethyl)cyclopropyl]amino]-2-oxo-acetyl]-1,5-dimethyl-pyrrole-2-carboxamide

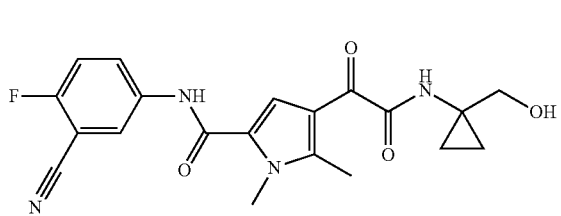 [SMILES: Cc1c(C(=O)C(=O)NC2(CO)CC2)cc(C(=O)Nc2ccc(F)c(C#N)c2)n1C]

To a vial containing (1-aminocyclopropyl)methanol (32 mg, 0.37 mmol), HATU (128.03 mg, 0.34 mmol) was added followed by 2-[5-[(3-cyano-4-fluoro-phenyl)-carbamoyl]-1,2-dimethyl-pyrrol-3-yl]-2-oxo-acetic acid (120 mg, 0.31 mmol) in DMF (0.48 mL, 6.17 mmol) and DIPEA (0.16 mL, 0.75 g/mL, 0.92 mmol). The resulting mixture was stirred for 5 hours at room temperature. Then water (5 mL) was added and the mixture was extracted using CH$_2$Cl$_2$ (2×5 mL). The combined organics were concentrated and the mixture purified via preparative HPLC (Stationary phase: RP)(Bridge Prep C18 OBD—10 μm, 30×150 mm, Mobile phase: 0.25% NH$_4$HCO$_3$ solution in water, MeOH) and further by silica gel column chromatography (gradient elution: EtOAc-heptane 0:100 to 100:0). The desired fractions were concentrated in vacuo and the residue was dried in a vacuum oven at 55° C. for 24 hours yielding compound 73 (14 mg). $^1$H NMR (400 MHz, DMSO-d$_6$) δ ppm 0.67-0.81 (m, 4 H), 2.55 (s, 3 H), 3.52 (d, J=4.8 Hz, 2 H), 3.84 (s, 3 H), 4.67-4.80 (m, 1 H), 7.52 (t, J=9.2 Hz, 1 H), 7.71 (s, 1 H), 8.02 (ddd, J=9.3, 4.9, 2.8 Hz, 1 H), 8.22 (dd, J=5.8, 2.8 Hz, 1 H), 8.78 (s, 1 H), 10.46 (s, 1 H). LC method B; Rt: 0.80 min. m/z: 397.1 (M−H)$^-$ Exact mass: 398.1.

Compound 74: N-(3-cyano-4-fluoro-phenyl)-4-[2-[(1-cyclopropyl-3-hydroxy-propyl)-amino]-2-oxo-acetyl]-1,5-dimethyl-pyrrole-2-carboxamide

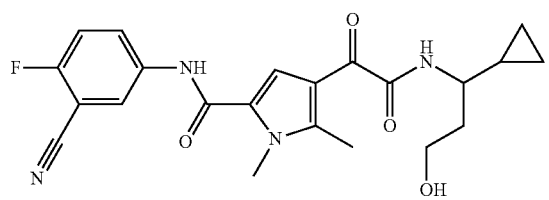 [SMILES: Cc1c(C(=O)C(=O)NC(CCO)C2CC2)cc(C(=O)Nc2ccc(F)c(C#N)c2)n1C]

3-amino-3-cyclopropyl-propan-1-ol was used as amine, resulting in compound 74 (40 mg). $^1$H NMR (400 MHz, DMSO-d$_6$) δ ppm 0.18-0.26 (m, 1 H), 0.27-0.41 (m, 2 H), 0.42-0.52 (m, 1 H), 0.91-1.03 (m, 1 H), 1.76 (q, J=6.9 Hz, 2 H), 2.57 (s, 3 H), 3.35-3.54 (m, 3 H), 3.84 (s, 3 H), 4.32-4.49 (m, 1 H), 7.52 (t, J=9.2 Hz, 1 H), 7.75 (s, 1 H), 8.02 (ddd, J=9.2, 4.9, 2.9 Hz, 1 H), 8.22 (dd, J=5.8, 2.8 Hz, 1 H), 8.54 (d, J=8.8 Hz, 1 H), 10.46 (s, 1 H). LC method C; Rt: 1.75 min. m/z: 425.2 (M−H)$^-$ Exact mass: 426.2

Compound 75: N-(3-cyano-4-fluoro-phenyl)-4-[2-[[(1R)-1-(hydroxymethyl)pentyl]amino]-2-oxo-acetyl]-1,5-dimethyl-pyrrole-2-carboxamide

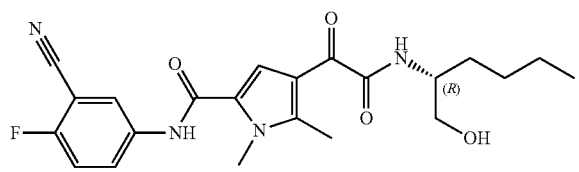

(R)-(−)-2-amino-1-hexanol was used as amine, resulting in compound 75 (22 mg). $^1$H NMR (400 MHz, DMSO-d$_6$) δ ppm 0.80-0.90 (m, 3 H), 1.19-1.46 (m, 5 H), 1.52-1.66 (m, 1 H), 2.57 (s, 3 H), 3.33-3.49 (m, 2 H), 3.75-3.89 (m, 4 H), 4.68-4.75 (m, 1 H), 7.52 (t, J=9.1 Hz, 1 H), 7.77 (s, 1 H), 8.03 (ddd, J=9.2, 5.0, 2.8 Hz, 1 H), 8.22 (dd, J=5.8, 2.8 Hz, 1 H), 8.28 (d, J=8.8 Hz, 1 H), 10.46 (s, 1 H). LC method C; Rt: 1.93 min. m/z: 427.4 (M−H)$^-$ Exact mass: 428.2

Compound 76: N-(3-cyano-4-fluoro-phenyl)-4-[2-[[1-(hydroxymethyl)-1-methyl-propyl]-amino]-2-oxo-acetyl]-1,5-dimethyl-pyrrole-2-carboxamide

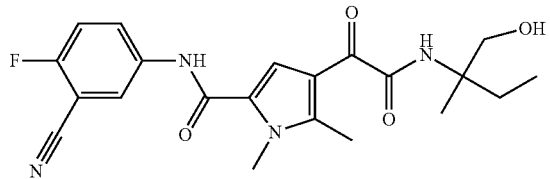 [SMILES: CCC(C)(CO)NC(=O)C(=O)c1cc(C(=O)Nc2ccc(F)c(C#N)c2)n(C)c1C]

2-amino-2-methylbutan-1-ol was used as amine, resulting in compound 76 (26 mg). $^1$H NMR (400 MHz, DMSO-d$_6$) δ ppm 0.81 (t, J=7.5 Hz, 3 H), 1.26 (s, 3 H), 1.62-1.88 (m, 2 H), 2.57 (s, 3 H), 3.39-3.47 (m, 1 H), 3.51-3.59 (m, 1 H), 3.84 (s, 3 H), 4.83-5.02 (m, 1 H), 7.52 (t, J=9.1 Hz, 1 H), 7.76 (s, 1 H), 7.80 (s, 1 H), 8.03 (ddd, J=9.2, 5.0, 2.8 Hz, 1 H), 8.22 (dd, J=5.7, 2.6 Hz, 1 H), 10.47 (s, 1 H). LC method C; Rt: 1.87 min. m/z: 413.4 (M−H)$^-$ Exact mass: 414.2

Compound 77: N-(3-cyano-4-fluoro-phenyl)-4-[2-[(1-cyclopropyl-2-hydroxy-1-methyl-ethyl)amino]-2-oxo-acetyl]-1,5-dimethyl-pyrrole-2-carboxamide

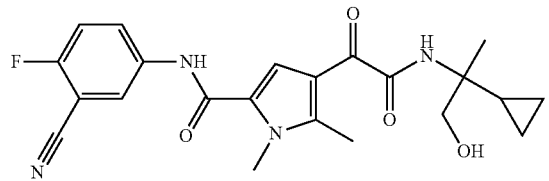 [SMILES: Cc1c(C(=O)C(=O)NC(C)(CO)C2CC2)cc(C(=O)Nc2ccc(F)c(C#N)c2)n1C]

2-amino-2-cyclopropylpropan-1-ol was used as amine, resulting in compound 77 (24 mg). $^1$H NMR (400 MHz, DMSO-d$_6$) δ ppm 0.28-0.41 (m, 3 H), 0.42-0.51 (m, 1 H), 1.10 (s, 3 H), 1.20-1.33 (m, 1 H), 2.57 (s, 3 H), 3.47-3.56 (m, 1 H), 3.59-3.66 (m, 1 H), 3.84 (s, 3 H), 4.92-4.99 (m, 1 H), 7.52 (t, J=9.2 Hz, 1 H), 7.75 (s, 1 H), 7.82 (s, 1 H), 8.03 (ddd, J=9.1, 5.0, 2.6 Hz, 1 H), 8.22 (dd, J=5.8, 2.8 Hz, 1 H), 10.48 (s, 1 H). LC method B; Rt: 0.98 min. m/z: 425.2 (M−H)$^-$ Exact mass: 426.2.

Compound 78: N-(3-cyano-4-fluoro-phenyl)-1,5-dimethyl-4-[2-[(3-methyltetrahydropyran-3-yl)amino]-2-oxo-acetyl]pyrrole-2-carboxamide

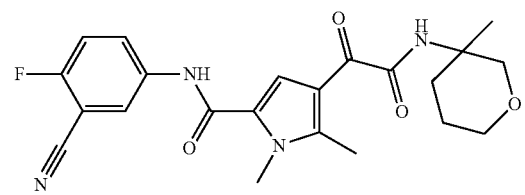 [SMILES: Cc1c(C(=O)C(=O)NC2(C)CCCOC2)cc(C(=O)Nc2ccc(F)c(C#N)c2)n1C]

3-methyloxan-3-amine was used as amine, resulting in compound 78 (15 mg). $^1$H NMR (400 MHz, DMSO-d$_6$) δ ppm 1.31 (s, 3 H), 1.40-1.70 (m, 3 H), 2.24 (m, J=12.8 Hz, 1 H), 2.57 (s, 3 H), 3.34-3.38 (m, 1 H), 3.38-3.47 (m, 1 H), 3.62-3.70 (m, 1 H), 3.84 (s, 3 H), 3.88-3.95 (m, 1 H), 7.52 (t, J=9.1 Hz, 1 H), 7.73 (s, 1 H), 7.97-8.07 (m, 2 H), 8.22 (dd, J=5.9, 2.6 Hz, 1 H), 10.47 (s, 1 H). LC method B; Rt: 0.99 min. m/z: 425.1 (M–H)⁻ Exact mass: 426.2.

Compound 79: N-(3-cyano-4-fluoro-phenyl)-4-[2-[(2-methoxy-1,1-dimethyl-ethyl)amino]-2-oxo-acetyl]-1,5-dimethyl-pyrrole-2-carboxamide

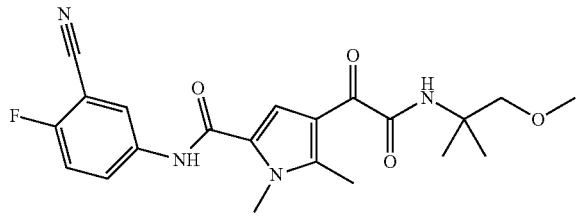 [SMILES: COCC(C)(C)NC(=O)C(=O)c1cc(C(=O)Nc2ccc(F)c(C#N)c2)n(C)c1C]

1-methoxy-2-amino-2-methylpropane was used as amine, resulting in compound 79 (31 mg). ¹H NMR (400 MHz, DMSO-d₆) δ ppm 1.33 (s, 6 H), 2.56 (s, 3 H), 3.30 (s, 3 H), 3.45 (s, 2 H), 3.84 (s, 3 H), 7.52 (t, J=9.1 Hz, 1 H), 7.70 (s, 1 H), 7.95-8.08 (m, 2 H), 8.22 (dd, J=5.8, 2.8 Hz, 1 H), 10.48 (s, 1 H). LC method C; Rt: 2.02 min. m/z: 413.2 (M–H)⁻ Exact mass: 414.2.

Compound 80: N-(3-cyano-4-fluoro-phenyl)-1,5-dimethyl-4-[2-oxo-2-[[2,2,2-trifluoro-1-(methoxymethyl)-1-methyl-ethyl]amino]acetyl]pyrrole-2-carboxamide

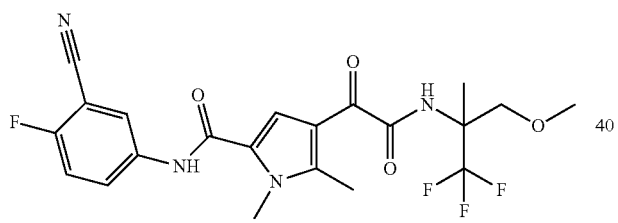

1,1,1-trifluoro-3-methoxy-2-methylpropan-2-amine hydrochloride was used as amine, resulting in compound 80 (52 mg). ¹H NMR (400 MHz, DMSO-d₆) δ ppm 1.60 (s, 3 H), 2.57 (s, 3 H), 3.34 (s, 3 H), 3.67 (d, J=9.7 Hz, 1 H), 3.84 (s, 3 H), 3.96 (d, J=9.7 Hz, 1 H), 7.52 (t, J=9.1 Hz, 1 H), 7.63 (s, 1 H), 8.01 (ddd, J=9.2, 5.0, 2.8 Hz, 1 H), 8.22 (dd, J=5.8, 2.8 Hz, 1 H), 8.53 (s, 1 H), 10.51 (s, 1 H). LC method B; Rt: 1.11 min. m/z: 467.1 (M–H)⁻ Exact mass: 468.1.

Compound 81: N-(3-cyano-4-fluoro-phenyl)-4-[2-[(3-hydroxy-1,1-dimethyl-propyl)amino]-2-oxo-acetyl]-1,5-dimethyl-pyrrole-2-carboxamide

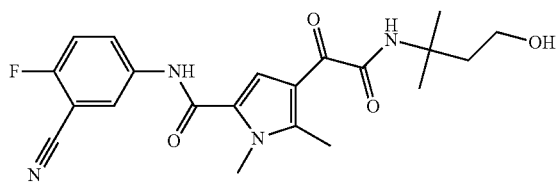 [SMILES: Cc1c(C(=O)C(=O)NC(C)(C)CCO)cc(C(=O)Nc2ccc(F)c(C#N)c2)n1C]

3-amino-3-methylbutan-1-ol was used as amine, resulting in compound 81 (24 mg). ¹H NMR (400 MHz, DMSO-d₆) δ ppm 1.38 (s, 6 H), 1.84 (t, J=6.6 Hz, 2 H), 2.56 (s, 3 H), 3.51-3.61 (m, 2 H), 3.84 (s, 3 H), 4.58-4.72 (m, 1 H), 7.52 (t, J=9.2 Hz, 1 H), 7.78 (s, 1 H), 8.03 (ddd, J=9.2, 4.9, 2.6 Hz, 1 H), 8.22 (dd, J=5.8, 2.8 Hz, 1 H), 8.34 (s, 1 H), 10.46 (s, 1 H). LC method B; Rt: 0.93 min. m/z: 413.2 (M–H)⁻ Exact mass: 414.2.

Compound 82: N-(3-cyano-4-fluoro-phenyl)-4-[2-[[4-hydroxy-1-(trifluoromethyl)cyclo-hexyl]amino]-2-oxo-acetyl]-1,5-dimethyl-pyrrole-2-carboxamide

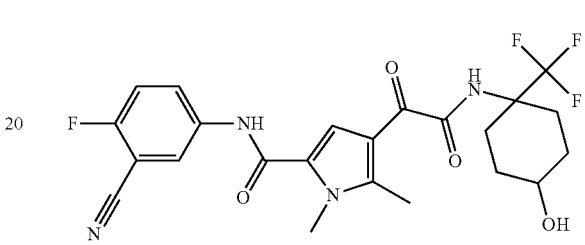

4-amino-4-(trifluoromethyl)cyclohexan-1-ol was used as amine, resulting in compound 82 (10 mg). ¹H NMR (400 MHz, DMSO-d₆) δ ppm 1.23-1.39 (m, 2 H), 1.45-1.62 (m, 2 H), 1.69-1.82 (m, 2 H), 2.54-2.72 (m, 6 H), 3.84 (s, 3 H), 4.71 (br. s., 1 H), 7.52 (t, J=9.1 Hz, 1 H), 7.57 (s, 1 H), 8.02 (ddd, J=9.1, 5.0, 2.6 Hz, 1 H), 8.21 (dd, J=5.8, 2.8 Hz, 1 H), 8.44 (s, 1 H), 10.52 (br. s., 1 H). LC method B; Rt: 1.00 min. m/z: 493.1 (M–H)⁻ Exact mass: 494.2.

Compound 83: N-(3-cyano-4-fluoro-phenyl)-3-fluoro-1-methyl-4-[2-oxo-2-[[3-(trifluoro-methyl)tetrahydrofuran-3-yl]amino]acetyl]pyrrole-2-carboxamide

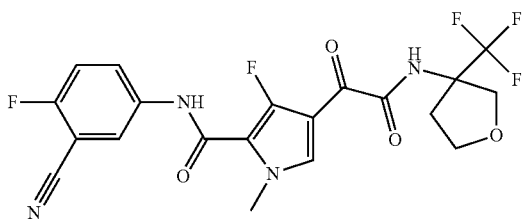 [SMILES: Cn1cc(C(=O)C(=O)NC2(C(F)(F)F)CCOC2)c(F)c1C(=O)Nc1ccc(F)c(C#N)c1]

Compound 83 was prepared similarly as described for compound 34, using 3-(trifluoro-methyl)tetrahydrofuran-3-amine hydrochloride instead of 2-methylpropan-2-amine. The obtained residue was dissolved in methanol under heating and the product crystallized upon addition of water, resulting in compound 83 (298 mg) as a white solid. LC method C; Rt: 1.94 min. m/z: 469.3 (M–H)⁻ Exact mass: 470.1. ¹H NMR (400 MHz, DMSO-d₆) δ ppm 2.26-2.42 (m, 1 H) 2.54-2.69 (m, 1 H) 3.69-3.81 (m, 1 H) 3.82-3.94 (m, 4 H) 4.14 (d, J=10.6 Hz, 1 H) 4.27 (d, J=10.6 Hz, 1 H) 7.54 (t, J=9.0 Hz, 1 H) 7.92-8.04 (m, 2 H) 8.18 (dd, J=5.7, 2.6 Hz, 1 H) 9.40 (s, 1 H) 10.37 (s, 1 H).

Compound 84: N-(3-cyano-4-fluoro-phenyl)-3-fluoro-1-methyl-4-[2-oxo-2-[[1-(trifluoro-methyl)cyclobutyl]amino]acetyl]pyrrole-2-carboxamide

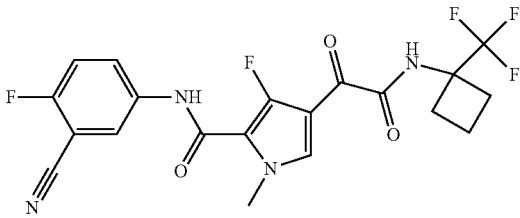 [SMILES: Cn1cc(C(=O)C(=O)NC2(C(F)(F)F)CCC2)c(F)c1C(=O)Nc1ccc(F)c(C#N)c1]

Compound 84 was prepared similarly as described for compound 34, using 1-(trifluoro-methyl)cyclobutan-1-amine instead of 2-methylpropan-2-amine. ¹H NMR (400 MHz, DMSO-d₆) δ ppm 1.87-2.02 (m, 2 H) 2.39-2.48 (m, 2 H) 2.52-2.67 (m, 2 H) 3.86 (s, 3 H) 7.54 (t, J=9.1 Hz, 1 H) 7.97 (ddd, J=9.2, 4.9, 2.6 Hz, 1 H) 8.04 (d, J=4.4 Hz, 1 H) 8.18 (dd, J=5.7, 2.6 Hz, 1 H) 9.33 (s, 1 H) 10.36 (s, 1 H). LC method B; Rt: 1.12 min. m/z: 453.1 (M–H)⁻ Exact mass: 454.1. Differential scanning calorimetry: From 30 to 300° C. at 10° C./min: Peak: 194.7° C.

Compound 85: N-(3-cyano-4-fluoro-phenyl)-3-fluoro-1-methyl-4-[2-oxo-2-[[(1R)-2,2,2-trifluoro-1-methyl-ethyl]amino]acetyl]pyrrole-2-carboxamide

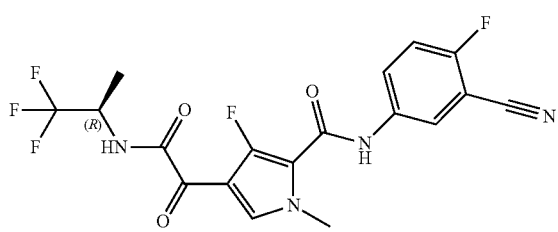

Compound 85 was prepared similarly as described for compound 34, using (R)-1,1,1-trifluoro-2-propylamine instead of 2-methylpropan-2-amine. LC method C; Rt: 1.95 min. m/z: 427.2 (M–H)⁻ Exact mass: 428.1. ¹H NMR (400 MHz, DMSO-d₆) δ ppm 1.35 (d, J=7.0 Hz, 3 H) 3.86 (s, 3 H) 4.58-4.75 (m, 1 H) 7.54 (t, J=9.1 Hz, 1 H) 7.97 (ddd, J=9.2, 4.8, 2.9 Hz, 1 H) 8.04 (d, J=4.4 Hz, 1 H) 8.18 (dd, J=5.7, 2.6 Hz, 1 H) 9.39 (d, J=9.0 Hz, 1 H) 10.37 (s, 1 H). Differential scanning calorimetry: From 30 to 300° C. at 10° C./min: Peak: 197.1° C.

Compound 86: 3,5-dichloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

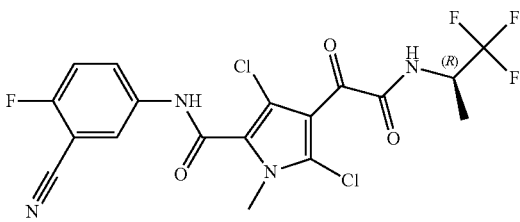

Compound 64 (50 mg, 0.12 mmol) was dissolved in CH₃CN (1.25 mL) and DMF (0.25 mL). NCS (24.41 mg, 0.18 mmol) was added and the mixture was stirred for 5 hours at room temperature and next heated at 40° C. overnight. The mixture was injected on a silica gel column as such and purified using silica gel column chromatography (gradient elution: EtOAc-heptane 0:100 to 100:0), resulting in compound 86 (26 mg). LC method B; Rt: 1.04 min. m/z: 477.0 (M–H)⁻ Exact mass: 478.0. ¹H NMR (400 MHz, DMSO-d₆) δ ppm 1.33 (d, J=7.0 Hz, 3 H), 3.75 (s, 3 H), 4.70 (dq, J=15.5, 7.6 Hz, 1 H), 7.57 (t, J=9.1 Hz, 1 H), 7.92-8.01 (m, 1 H), 8.20 (dd, J=5.7, 2.6 Hz, 1 H), 9.50 (d, J=8.8 Hz, 1 H), 10.91 (br. s., 1 H).

Compound 87: 5-chloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide

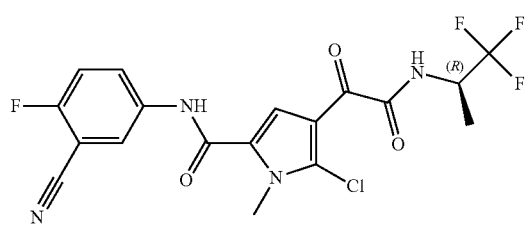

To a solution of compound 64 (25 mg, 0.061 mmol) in HOAc (0.5 mL,), NCS (12.2 mg, 0.091 mmol) was added followed by trifluoromethanesulfonic acid (10 μL, 0.11 mmol). The resulting mixture was stirred at room temperature for 18 hours. Then it was poured into water and extracted using CH₂Cl₂ (3×15 mL). The combined extracts were washed with NaHCO₃ (20 mL, aq/sat), dried on Na₂SO₄, filtered and concentrated in vacuo. The obtained residue was purified by Preparative HPLC on (RP SunFire Prep C18 OBD—10 μm, 30×150 mm). Mobile phase (0.25% NH₄HCO₃ solution in water, MeOH), resulting in compound 87 (3 mg). LC method B; Rt: 1.09 min. m/z: 443.0 (M–H)⁻ Exact mass: 444.1. ¹H NMR (600 MHz, CHLOROFORM-d) δ ppm 1.44 (d, J=6.9 Hz, 3 H), 4.02 (s, 3 H), 4.65 (dquin, J=9.8, 7.0, 7.0, 7.0, 7.0 Hz, 1 H), 7.22 (t, J=8.7 Hz, 1 H), 7.45 (d, J=9.7 Hz, 1 H), 7.71 (ddd, J=9.1, 4.5, 2.8 Hz, 1 H), 7.96 (s, 1 H), 8.06 (dd, J=5.4, 2.8 Hz, 1 H), 8.11 (s, 1 H).

Compound 88: 5-chloro-N-(3-cyano-4-fluoro-phenyl)-1-methyl-4-[2-oxo-2-[[(1S)-2,2,2-trifluoro-1-methyl-ethyl]amino]acetyl]pyrrole-2-carboxamide

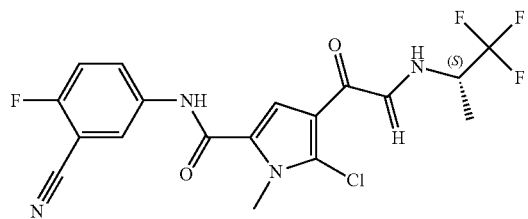

Compound 88 was prepared similarly as described for compound 87 (stirring at room temperature for 6 hours instead of 18 hours), starting from compound 51 instead of compound 64. ¹H NMR (400 MHz, DMSO-d₆) δ ppm 1.35 (d, J=7.0 Hz, 3 H), 3.93 (s, 3 H), 4.62-4.79 (m, 1 H), 7.54 (t, J=9.1 Hz, 1 H), 7.79 (s, 1 H), 8.01 (ddd, J=9.2, 4.8, 2.9 Hz, 1 H), 8.21 (dd, J=5.7, 2.6 Hz, 1 H), 9.44 (br. s., 1 H), 10.59 (br. s., 1 H) LC method B; Rt: 1.12 min. m/z: 443.0 (M−H)⁻ Exact mass: 444.1.

Compound 89: 5-chloro-N-(3-cyano-4-fluoro-phenyl)-3-fluoro-1-methyl-4-[2-oxo-2-[[3-(trifluoromethyl)tetrahydrofuran-3-yl]amino]acetyl]pyrrole-2-carboxamide

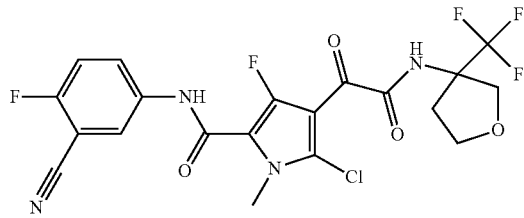 [SMILES: Cn1c(Cl)c(C(=O)C(=O)NC2(C(F)(F)F)CCOC2)c(F)c1C(=O)Nc1ccc(F)c(C#N)c1]

Compound 83 (84 mg, 0.179 mmol) was suspended in dry acetonitrile (1.7 mL) and DMF (0.61 mL). The mixture was cooled on an ice bath and NCS (35.8 mg, 0.268 mmol) was added. The mixture was allowed to rise to room temperature and was then heated at 55° C. for 16 hour. Purification was performed via Preparative HPLC (Stationary phase: RP) (Bridge Prep C18 ODB—5 µm, 30×250 mm, Mobile phase: 0.25% NH₄HCO₃ solution in water, CH₃CN), resulting in compound 89 (10 mg). LC method C; Rt: 1.88 min. m/z: 503.1 (M-H)⁻ Exact mass: 504.1. ¹H NMR (400 MHz, DMSO-d₆) δ ppm 2.28-2.42 (m, 1 H) 2.45-2.59 (m, 1 H) 3.75-3.84 (m, 4 H) 3.85-3.97 (m, 1 H) 4.10 (d, J=10.3 Hz, 1 H) 4.23 (d, J=10.6 Hz, 1 H) 7.55 (t, J=9.1 Hz, 1 H) 7.96 (ddd, J=9.2, 4.8, 2.9 Hz, 1 H) 8.16 (dd, J=5.7, 2.9 Hz, 1 H) 9.54 (s, 1 H) 10.61 (s, 1 H).

Compound 90: 5-chloro-N-(3-cyano-4-fluoro-phenyl)-3-fluoro-1-methyl-4-[2-oxo-2-[[1-(trifluoromethyl)cyclobutyl]amino]acetyl]pyrrole-2-carboxamide

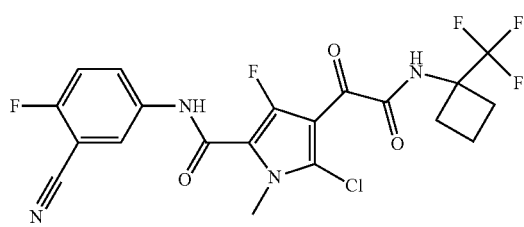 [SMILES: Cn1c(Cl)c(C(=O)C(=O)NC2(C(F)(F)F)CCC2)c(F)c1C(=O)Nc1ccc(F)c(C#N)c1]

Compound 90 (29 mg) was prepared similarly as described for compound 89, starting from compound 84 instead of 83. LC method C; Rt: 2.02 min. m/z: 487.1 (M−H)⁻ Exact mass: 488.1. Differential scanning calorimetry: From 30 to 300° C. at 10° C./min: Peak: 174.9° C. ¹H NMR (400 MHz, DMSO-d₆) δ ppm 1.84-2.08 (m, 2 H) 2.40-2.57 (m, 4 H) 3.81 (s, 3 H) 7.56 (s, 1 H) 7.91-8.00 (m, 1 H) 8.16 (dd, J=5.8, 2.8 Hz, 1 H) 9.41 (s, 1 H) 10.60 (br. s, 1 H).

Compound 91: 5-chloro-N-(3-cyano-4-fluoro-phenyl)-3-fluoro-1-methyl-4-[2-oxo-2-[[(1R)-2,2,2-trifluoro-1-methyl-ethyl]amino]acetyl]pyrrole-2-carboxamide

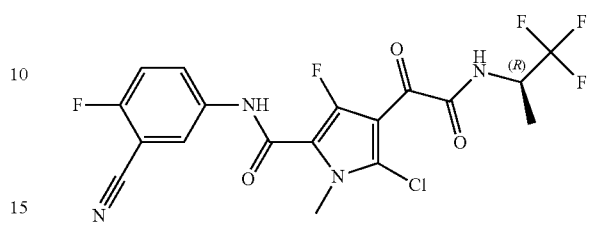

Compound 91 was prepared similarly as described for compound 89, starting from compound 85 instead of 83. LC method C; Rt: 1.92 min. m/z: 461.1 (M−H)⁻ Exact mass: 462.1. ¹H NMR (400 MHz, DMSO-d₆) δ ppm 1.32 (d, J=7.0 Hz, 3 H) 3.80 (s, 3 H) 4.60-4.77 (m, 1 H) 7.55 (s, 1 H) 7.95 (ddd, J=9.2, 4.8, 2.9 Hz, 1 H) 8.16 (dd, J=5.8, 2.8 Hz, 1 H) 9.48 (d, J=8.6 Hz, 1 H) 10.58 (br. s., 1 H).

Compound 92: 3-chloro-N-(3-cyano-4-fluoro-phenyl)-4-[2-[(2-hydroxy-1,1-dimethyl-ethyl)amino]-2-oxo-acetyl]-1-methyl-pyrrole-2-carboxamide

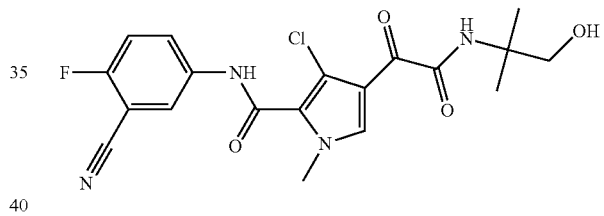

Et₃N (0.18 mL, 1.287 mmol) was added to a solution of 2-[4-chloro-5-[(3-cyano-4-fluoro-phenyl)carbamoyl]-1-methyl-pyrrol-3-yl]-2-oxo-acetic acid (150 mg, 0.429 mmol), HATU (204 mg, 0.536 mmol), 2-amino-2-methyl-1-propanol (0.051 mL, 0.536 mmol) in DMF (1.1 mL) and stirred 30 minutes at room temperature. The solution was purified by silica gel column chromatography using a gradient from 0 till 50% EtOAc in heptane. The product fractions were concentrated, dissolved in THF (3 mL) and water (1 mL,). lithium hydroxide monohydrate (30 mg) was added and the mixture was stirred for 1 h at room temperature. The mixture was concentrated in vacuo and the residue partioned between water and CH₂Cl₂. The organic layer was separated and concentrated in vacuo. The obtained residue was crystallized from MeOH and water. The product was filtered off and washed with water and diisopropylether. The product was dried in vacuo resulting in compound 92 (41 mg) as a white solid. ¹H NMR (400 MHz, DMSO-d₆) δ ppm 1.29 (s, 6 H) 3.45 (d, J=5.7 Hz, 2 H) 3.82 (s, 3 H) 4.99 (t, J=5.8 Hz, 1 H) 7.56 (t, J=9.1 Hz, 1 H) 7.90 (s, 1 H) 7.98 (ddd, J=9.2, 4.9, 2.6 Hz, 1 H) 8.21 (dd, J=5.8, 2.8 Hz, 1 H) 8.26 (s, 1 H) 10.71 (s, 1 H). LC method C; Rt: 1.72 min. m/z: 419.2 (M−H)⁻ Exact mass: 420.1.

Compound 93: N-(3-cyano-4-fluoro-phenyl)-4-[2-[[(1R)-2,2-difluoro-1-methylpropyl]-amino]-2-oxo-acetyl]-3-fluoro-1-methyl-pyrrole-2-carboxamide

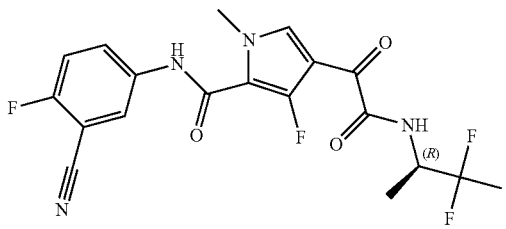

Compound 93 (130 mg) was prepared similarly as described for compound 34, using (2R)-3,3-difluorobutan-2-amine hydrochloride instead of 2-methylpropan-2-amine. LC method C; Rt: 1.97 min. m/z: 423.4 (M−H)⁻ Exact mass: 424.1. Differential scanning calorimetry: From 30 to 300° C. at 10° C./min: Peak: 206.8° C. $^1$H NMR (400 MHz, DMSO-d$_6$) δ ppm 1.23 (d, J=7.0 Hz, 3 H), 1.61 (t, J=19.3 Hz, 3 H), 3.86 (s, 3 H), 4.25-4.40 (m, 1 H), 7.54 (t, J=9.1 Hz, 1 H), 7.97 (ddd, J=9.1, 5.0, 2.6 Hz, 1 H), 8.02 (d, J=4.2 Hz, 1 H), 8.18 (dd, J=5.7, 2.6 Hz, 1 H), 8.97 (d, J=9.2 Hz, 1 H), 10.35 (br. s., 1 H).

Compound 94: N-(3-cyano-4-fluoro-phenyl)-4-[2-[(2-hydroxy-1,1-dimethyl-ethyl)amino]-2-oxo-acetyl]-1,5-dimethyl-pyrrole-2-carboxamide

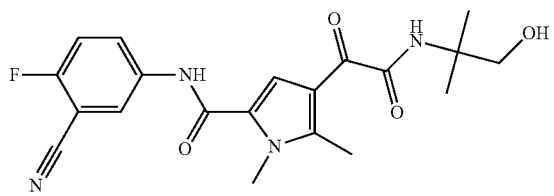 [SMILES: Cc1c(C(=O)C(=O)NC(C)(C)CO)cc(C(=O)Nc2ccc(F)c(C#N)c2)n1C]

Compound 94 (46 mg) was prepared similarly as described for compound 73, using 2-amino-2-methyl-1-propanol instead of (1-aminocyclopropyl) methanol. LC method C; Rt: 1.72 min. m/z: 399.2 (M−H)⁻ Exact mass: 400.2. $^1$H NMR (400 MHz, DMSO-d$_6$) δ ppm 1.30 (s, 6 H) 2.56 (s, 3 H) 3.45 (d, J=5.9 Hz, 2 H) 3.84 (s, 3 H) 4.97 (t, J=5.7 Hz, 1 H) 7.52 (t, J=9.1 Hz, 1 H) 7.80 (s, 1 H) 7.89 (s, 1 H) 8.03 (ddd, J=9.2, 5.0, 2.8 Hz, 1 H) 8.22 (dd, J=5.9, 2.6 Hz, 1 H) 10.45 (s, 1 H)

Compound 95: N-(3-cyano-4-fluoro-phenyl)-3-fluoro-4-[2-[[(1R)-2-hydroxy-1-methyl-ethyl]amino]-2-oxo-acetyl]-1-methyl-pyrrole-2-carboxamide

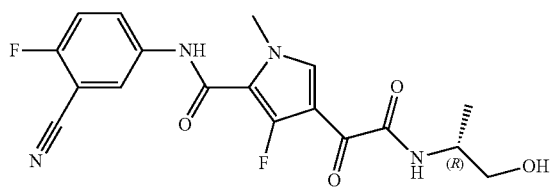

Compound 95 (28 mg) was prepared similarly as described for compound 34, using D-alaninol instead of 2-methylpropan-2-amine. LC method C; Rt: 1.54 min. m/z: 389.2 (M−H)⁻ Exact mass: 390.1. Differential scanning calorimetry: From 30 to 300° C. at 10° C./min: Peak: 191.8° C. $^1$H NMR (400 MHz, DMSO-d$_6$) δ ppm 1.10 (d, J=6.8 Hz, 3 H) 3.32-3.46 (m, 2 H) 3.81-3.92 (m, 4 H) 4.76 (t, J=5.6 Hz, 1 H) 7.54 (t, J=9.1 Hz, 1 H) 7.97 (ddd, J=9.1, 4.8, 2.8 Hz, 1 H) 8.12 (d, J=4.4 Hz, 1 H) 8.18 (dd, J=5.7, 2.6 Hz, 1 H) 8.42 (d, J=8.4 Hz, 1 H) 10.34 (s, 1 H).

Compound 96: N-(3-cyano-4-fluoro-phenyl)-3-fluoro-4-[2-[(2-methoxy-1,1-dimethyl-ethyl)amino]-2-oxo-acetyl]-1-methyl-pyrrole-2-carboxamide

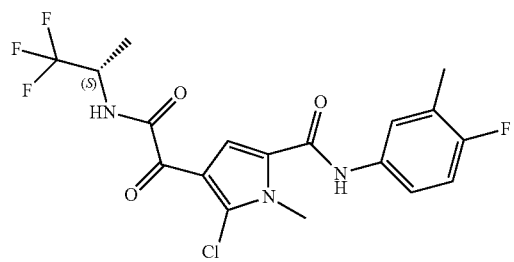

Compound 96 (145 mg) was prepared similarly as described for compound 34, using 1-methoxy-2-methylpropan-2-amine instead of 2-methylpropan-2-amine. LC method C; Rt: 1.98 min. m/z: 417.2 (M−H)⁻ Exact mass: 418.1. $^1$H NMR (400 MHz, CHLOROFORM-d) δ ppm 1.43 (s, 6 H) 3.38-3.45 (m, 5 H) 3.99 (s, 3 H) 7.18-7.24 (m, 1 H) 7.45 (s, 1 H) 7.66 (ddd, J=9.1, 4.5, 2.8 Hz, 1 H) 7.87-7.97 (m, 1 H) 8.05 (dd, J=5.5, 2.6 Hz, 1 H) 8.24 (d, J=4.6 Hz, 1 H).

Compound 97: 5-chloro-N-(4-fluoro-3-methyl-phenyl)-1-methyl-4-[2-oxo-2-[[(1S)-2,2,2-trifluoro-1-methyl-ethyl]amino]acetyl]pyrrole-2-carboxamide 2-(5-(4-fluoro-3-methylphenylcarbamoyl)-1-methyl-1H-pyrrol-3-yl)-2-oxoacetic acid (500 mg, 1.64 mmol) was dissolved in HOAc (25 mL). Trifluoromethanesulfonic acid (218 µL) was added, followed by NCS (219 mg, 1.64 mmol) in portions. This was stirred for 4 hours at room temperature. The mixture was poured into water (20 mL) and then extracted using dichloromethane (3×25 mL). The combined extracts were washed with NaHCO$_3$ (2×25 mL/sat./aq.), washed with brine (25 mL), dried on Na$_2$SO$_4$, filtered and concentrated in vacuo. The obtained crude was purified using silica gel column chromatography (gradient elution: EtOAc-heptane 0:100 to 100:0) yielding 2-[2-chloro-5-[(4-fluoro-3-methyl-phenyl)carbamoyl]-1-methyl-pyrrol-3-yl]-2-oxo-acetic acid (109 mg) as an oil which was used as such. A vial was charged with 2-[2-chloro-5-[(4-fluoro-3-methylphenyl)carbamoyl]-1-methyl-pyrrol-3-yl]-2-oxo-acetic acid (109.4 mg, 0.32 mmol), (S)-1,1,1-trifluoro-2-propylamine (43.8 mg, 0.39 mmol), DMF (1 mL) and DIPEA (0.17 mL), followed by addition of HATU (135 mg, 0.36 mmol). The resulting mixture was stirred for 2 hours at room temperature. Water (5 mL) was added and the mixture was extracted using CH$_2$Cl$_2$ (2×15 mL). The mixture was purified using silica gel column chromatography (gradient elution: EtOAc-heptane 0:100 to 100:0). The desired fractions were concentrated in vacuo and the obtained residue was dried in a vacuum oven at 55° C. for 24 hours, resulting in compound 97 (17 mg). LC method B; Rt: 1.18 min. m/z: 432.1 (M−H)$^-$ Exact mass: 433.1. $^1$H NMR (400 MHz, DMSO-d$_6$) δ ppm 1.34 (d, J=7.0 Hz, 3 H), 2.23 (d, J=1.8 Hz, 3 H), 3.92 (s, 3 H), 4.63-4.79 (m, 1 H), 7.11 (t, J=9.2 Hz, 1 H), 7.48-7.56 (m, 1 H), 7.63 (dd, J=7.0, 2.2 Hz, 1 H), 7.73 (s, 1 H), 9.42 (d, J=7.9 Hz, 1 H), 10.24 (s, 1 H).

Compound 98: 4-[2-(tert-butylamino)-2-oxo-acetyl]-5-chloro-N-(3-cyano-4-fluoro-phenyl)-1-methyl-pyrrole-2-carboxamide

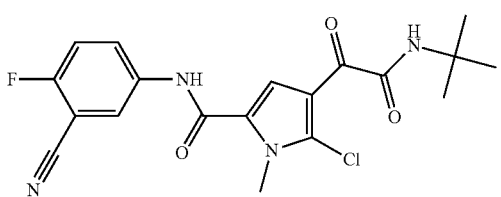 [SMILES: Cn1c(C(=O)Nc2ccc(F)c(C#N)c2)cc(C(=O)C(=O)NC(C)(C)C)c1Cl]

Compound 98 (17 mg) was prepared similarly as described for compound 87 (stirring at room temperature for 5 hours instead of 18 hours), starting from compound 15 instead of compound 64. The obtained crude was purified using silica gel column chromatography (gradient elution: EtOAc-heptane 0:100 to 100:0). $^1$H NMR (400 MHz, CHLOROFORM-d) δ ppm 1.37 (s, 9 H), 3.92 (s, 3 H), 7.53 (t, J=9.1 Hz, 1 H), 7.76 (s, 1 H), 8.02 (ddd, J=9.2, 4.9, 2.6 Hz, 1 H), 8.14-8.28 (m, 2 H), 10.48-10.68 (m, 1 H). LC method B; Rt: 1.15 min. m/z: 403.2 (M−H)$^-$ Exact mass: 404.1.

Compound 99: N-(3-cyano-4-fluoro-phenyl)-3-fluoro-4-[2-[(2-hydroxy-1,1-dimethyl-ethyl)amino]-2-oxo-acetyl]-1-methyl-pyrrole-2-carboxamide

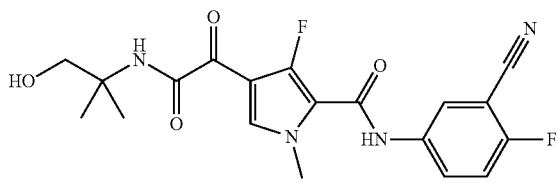 [SMILES: Cn1cc(C(=O)C(=O)NC(C)(C)CO)c(F)c1C(=O)Nc1ccc(F)c(C#N)c1]

Ethyl 3-fluoro-4-[2-[(2-hydroxy-1,1-dimethyl-ethyl)amino]-2-oxo-acetyl]-1-methyl-pyrrole-2-carboxylate was prepared similarly as described for ethyl 4-[2-(tert-butylamino)-2-oxo-acetyl]-3-fluoro-1-methyl-pyrrole-2-carboxylate, using 2-amino-2-methyl-1-propanol instead of 2-methylpropan-2-amine and stirring at room temperature instead of 30 minutes at 65° C. Compound 99 (5 mg) was prepared similarly as described for compound 34, using ethyl 3-fluoro-4-[2-[(2-hydroxy-1,1-dimethyl-ethyl)amino]-2-oxo-acetyl]-1-methyl-pyrrole-2-carboxylate instead of ethyl 4-[2-(tert-butylamino)-2-oxo-acetyl]-3-fluoro-1-methyl-pyrrole-2-carboxylate. Compound 99 was purified by silica gel column chromatography using a gradient from 0 till 50% EtOAc in heptane and further purified via Preparative HPLC (Stationary phase: RP)(Bridge Prep C18 OBD—10 μm, 30×150 mm, Mobile phase: 0.25% NH$_4$HCO$_3$ solution in water, CH$_3$CN). LC method B; Rt: 0.90 min. m/z: 403.2 (M−H)$^-$ Exact mass: 404.1. $^1$H NMR (400 MHz, CHLOROFORM-d) δ ppm 1.39 (s, 6 H) 3.66-3.71 (m, 2 H) 3.72-3.79 (m, 1 H) 4.00 (s, 3 H) 7.17-7.24 (m, 1 H) 7.32-7.39 (m, 1 H) 7.61-7.71 (m, 1 H) 7.88-7.95 (m, 1 H) 8.05 (dd, J=5.4, 2.8 Hz, 1 H) 8.23 (d, J=4.6 Hz, 1 H)

Compound 100: 5-chloro-N-(3-cyano-4-fluoro-phenyl)-1-methyl-4-[2-[(3-methyloxetan-3-yl)amino]-2-oxo-acetyl]pyrrole-2-carboxamide

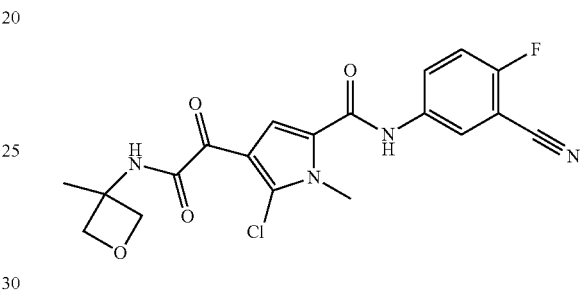

Compound 100 (12.8 mg) was prepared similarly as described for compound 87 (stirring at room temperature for 5 hours instead of 18 hours, using DMF (4.84 mL) instead of HOAc), starting from compound 16 instead of compound 64. The obtained crude was purified using silica gel column chromatography (gradient elution: EtOAc-heptane 0:100 to 100:0). LC method B; Rt: 0.94 min. m/z: 417.1 (M−H)$^-$ Exact mass: 418.08. $^1$H NMR (400 MHz, DMSO-d6) δ ppm 1.60 (s, 3 H), 3.93 (s, 3 H), 4.37 (d, J=6.6 Hz, 2 H), 4.73 (d, J=6.4 Hz, 2 H), 7.53 (t, J=9.1 Hz, 1 H), 7.90 (s, 1 H), 8.02 (ddd, J=9.2, 4.9, 2.6 Hz, 1 H), 8.21 (dd, J=5.7, 2.6 Hz, 1 H), 9.34 (s, 1 H), 10.58 (br. s., 1 H).

Compound 101: N-(3-cyano-4-fluoro-phenyl)-3-fluoro-1-methyl-4-[2-oxo-2-[[1-(trifluoro-methyl)cyclopropyl]amino]acetyl]pyrrole-2-carboxamide

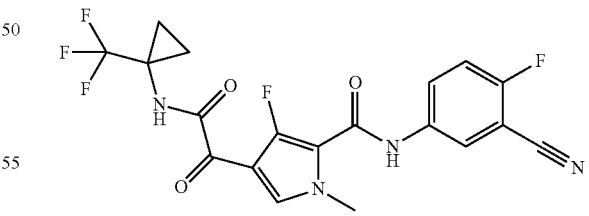

Compound 101 (17 mg) was prepared similarly as described for compound 34 using 1-trifluoromethyl-1-cyclopropylamine instead of 2-methylpropan-2-amine. LC method B; Rt: 1.05 min. m/z: 439.1 (M−H)$^-$ Exact mass: 440.09. 1H NMR (400 MHz, DMSO-d6) δ ppm 1.07-1.20 (m, 2 H), 1.26-1.37 (m, 2 H), 3.85 (s, 3 H), 7.53 (t, J=9.1 Hz, 1 H), 7.96 (ddd, J=9.2, 4.8, 2.9 Hz, 1 H), 8.04 (d, J=4.4 Hz, 1 H), 8.18 (dd, J=5.8, 2.8 Hz, 1 H), 9.57 (s, 1 H), 10.37 (br. s., 1 H).

Compound 102: N-(3-cyano-4-fluoro-phenyl)-3-fluoro-4-[2-[[1-(hydroxymethyl)cyclo-propyl]amino]-2-oxo-acetyl]-1-methyl-pyrrole-2-carboxamide

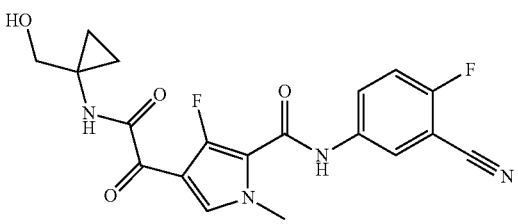 [SMILES: Cn1cc(C(=O)C(=O)NC2(CO)CC2)c(F)c1C(=O)Nc1ccc(F)c(C#N)c1]

Compound 102 (37.7 mg) was prepared similarly as described for compound 34 using 1-amino-cyclopropanemethanol instead of 2-methylpropan-2-amine. LC method B; Rt: 0.81 min. m/z: 401.2 (M−H)⁻ Exact mass: 402.11. 1H NMR (400 MHz, DMSO-d6) δ ppm 1.36 (s, 9 H), 2.56 (s, 3 H), 3.84 (s, 3 H), 7.52 (t, J=9.1 Hz, 1 H), 7.65 (s, 1 H), 7.98-8.05 (m, 1 H), 8.08 (s, 1 H), 8.22 (dd, J=5.7, 2.6 Hz, 1 H), 10.46 (s, 1 H)

BIOLOGICAL EXAMPLES

Anti-HBV Activity of Compounds of Formula (IA)

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| Co. No. | HepG 2.2.15 EC50 (μM) | HepG2 117 $EC_{50}$ (μM) | HepG2 4 days $CC_{50}$ (μM) |
|---|---|---|---|
| 1 | 0.014 | 0.10 | >25 |
| 2 | 0.029 | 0.75 | >25 |
| 3 | 0.015 | 0.040 | >25 |
| 4 | 0.013 | 0.015 | >25 |
| 5 | 0.056 | 0.099 | >25 |
| 6 | 0.047 | 0.19 | >25 |
| 7 | 0.21 | 0.058 | >25 |
| 8 | 0.052 | 0.038 | >25 |
| 9 | 0.17 | 0.20 | >25 |
| 10 | 0.072 | 0.042 | >25 |
| 11 | 0.050 | 0.096 | >25 |
| 12 | 0.043 | 0.74 | >25 |
| 13 | 0.033 | >1 | >25 |
| 14 | 0.030 | 0.038 | >25 |
| 15 | 0.027 | 0.043 | >25 |
| 16 | 0.048 | 0.040 | >25 |
| 17 | 0.029 | 0.57 | >25 |
| 18 | 0.054 | 0.37 | >25 |
| 19 | <0.004 | 0.002 | >100 |
| 20 | <0.004 | 0.002 | >25 |
| 21 | 0.009 | 0.011 | >25 |
| 22 | 0.010 | 0.008 | >25 |
| 23 | 0.005 | 0.008 | >25 |
| 24 | 0.020 | 0.024 | >25 |
| 25 | | >1 | >25 |
| 26 | | 0.070 | >25 |
| 27 | | 0.005 | >25 |
| 28 | <0.004 | 0.019 | >25 |
| 29 | | 0.014 | >25 |
| 30 | <0.004 | 0.003 | >25 |
| 31 | 0.012 | 0.019 | >25 |
| 32 | <0.004 | <0.004 | >25 |
| 33 | | 0.247 | >25 |
| 34 | | 0.009 | >25 |
| 35 | | 0.004 | >25 |
| 36 | | <0.004 | >25 |
| 37 | | 0.002 | >25 |
| 38 | | 0.015 | >25 |
| 39 | | 0.006 | >25 |
| 40 | | 0.007 | >25 |
| 41 | | 0.003 | >25 |
| 42 | | 0.002 | >25 |
| 43 | | 0.003 | >25 |
| 44 | | 0.003 | >25 |
| 45 | | 0.006 | >25 |
| 46 | | 0.003 | >25 |
| 47 | | <0.004 | >25 |
| 48 | | 0.022 | >25 |
| 49 | | 0.034 | >25 |
| 50 | | 0.004 | >25 |
| 51 | | 0.042 | >25 |
| 52 | | 0.067 | >25 |
| 53 | | 0.039 | >25 |
| 54 | | 0.010 | >25 |
| 55 | | 0.009 | >25 |
| 56 | | 0.005 | >25 |
| 57 | | 0.006 | >25 |
| 58 | | 0.006 | >25 |
| 59 | | 0.004 | >25 |
| 60 | | 0.011 | >25 |
| 61 | | 0.12 | >25 |
| 62 | | 0.23 | >25 |
| 63 | | 0.21 | >25 |
| 64 | | 0.066 | >25 |
| 65 | | 0.16 | >25 |
| 66 | | 0.11 | >25 |
| 67 | | 0.094 | >25 |
| 68 | | 0.078 | >25 |
| 69 | | 0.049 | >25 |
| 70 | | 0.025 | >25 |
| 71 | | 0.024 | >25 |
| 72 | | 0.018 | >25 |
| 73 | | 0.017 | >25 |
| 74 | | 0.015 | >25 |
| 75 | | 0.014 | >25 |
| 76 | | 0.013 | >25 |
| 77 | | 0.012 | >25 |
| 78 | | 0.008 | >25 |
| 79 | | 0.008 | >25 |
| 80 | | 0.007 | >25 |
| 81 | | 0.012 | >25 |
| 82 | | 0.003 | >25 |

TABLE 1-continued

| Co. No. | HepG 2.2.15 EC50 (µM) | HepG2 117 EC50 (µM) | HepG2 4 days CC50 (µM) |
|---|---|---|---|
| 83 | | 0.006 | 11.8 |
| 84 | | 0.003 | 21.9 |
| 85 | | 0.014 | >25 |
| 86 | | 0.006 | >25 |
| 89 | | 0.008 | >25 |
| 90 | | 0.032 | >25 |
| 91 | | 0.30 | >25 |
| 93 | | 0.015 | >25 |
| 94 | | 0.004 | >25 |
| 95 | | 0.065 | >25 |
| 96 | | 0.006 | >25 |

The invention claimed is:

1. A compound of Formula (IA)

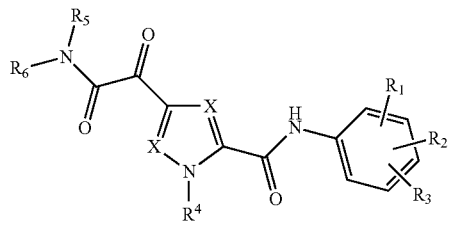

or a stereoisomer or tautomeric form thereof, wherein:
each X independently is $CR^7$;
$R^1$, $R^2$ and $R^3$ are independently selected from the group consisting of hydrogen, fluoro, chloro, bromo, —$CHF_2$, —$CH_2F$, —$CF_3$, —CN, $C_1$-$C_3$alkyl and $C_3$-$C_4$cycloalkyl;
$R^4$ is selected from the group consisting of hydrogen, $C_1$-$C_3$alkyl and $C_3$-$C_4$cycloalkyl;
$R^5$ is hydrogen;
$R^6$ is selected from the group consisting of $C_1$-$C_6$alkyl and a 3-7 membered saturated ring optionally containing one or more heteroatoms each independently selected from the group consisting of O, S and N, said $C_1$-$C_6$alkyl or said 3-7 membered saturated ring is optionally substituted with one or more substituents selected from the group consisting of fluoro, $C_3$-$C_4$cycloalkyl, —$OR^8$, oxo, —CN, —C(=O)—$OR^8$, —C(=O)—N($R^8$)$_2$ and $C_1$-$C_3$alkyl, wherein said $C_1$-$C_3$alkyl is optionally substituted with one or more fluoro;
each $R^7$ is independently selected from the group consisting of hydrogen, $C_3$-$C_4$cycloalkyl, —CN, fluoro, chloro, bromo and $C_1$-$C_3$alkyl, wherein said $C_1$-$C_3$alkyl is optionally substituted with one or more fluoro;
$R^8$ is hydrogen or $C_1$-$C_3$alkyl;
or a pharmaceutically acceptable salt or a solvate thereof.

2. The compound according to claim 1, wherein $R^1$ is selected from the group consisting of hydrogen, fluoro, chloro, —$CHF_2$, —CN, —$CF_3$ and methyl.

3. The compound according to claim 1, wherein $R^4$ is methyl.

4. The compound according to claim 1, wherein $R^6$ is a 3-7 membered saturated ring optionally containing one oxygen, said 3-7 membered saturated ring is optionally substituted with one or more substituents selected from fluoro or $C_1$-$C_3$alkyl optionally substituted with one or more fluoro.

5. The compound according to claim 1, wherein $R^6$ is a 4 or 5 membered saturated ring optionally containing one oxygen, said 4 or 5 membered saturated ring is optionally substituted with one or more $C_1$-$C_3$ alkyl, wherein said $C_1$-$C_3$alkyl is optionally substituted with one or more fluoro.

6. The compound according to claim 1, wherein $R^6$ is a branched $C_1$-$C_6$alkyl optionally substituted with one or more fluoro.

7. The compound according to claim 1 of the structure of Formula Ia

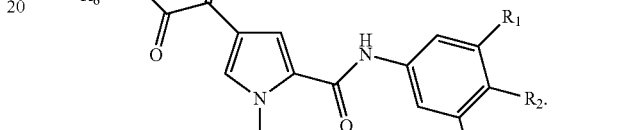

8. The compound according to claim 1 of the structure of Formula Ib

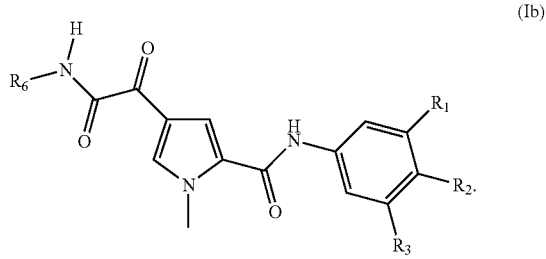

9. A pharmaceutical composition comprising a compound according to claim 1, and a pharmaceutically acceptable carrier.

10. A product containing (a) a compound according to claim 1, and (b) at least one HBV inhibitor, as a combined preparation for simultaneous or sequential use in the treatment of HBV infections.

11. The compound according to claim 8, wherein $R_1$ is H; $R_2$ is fluoro; and $R_3$ is —CN.

12. The compound according to claim 8, wherein $R_1$ is H; $R_2$ is fluoro; and $R_3$ is —$CH_3$.

13. The compound according to claim 1, wherein one $R^7$ is H; and one $R^7$ is chloro or bromo.

14. The compound according to claim 1, wherein $R^6$ is selected from the group consisting of

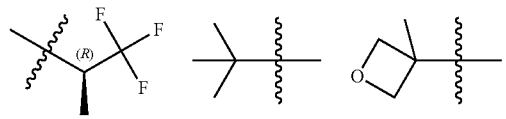

-continued

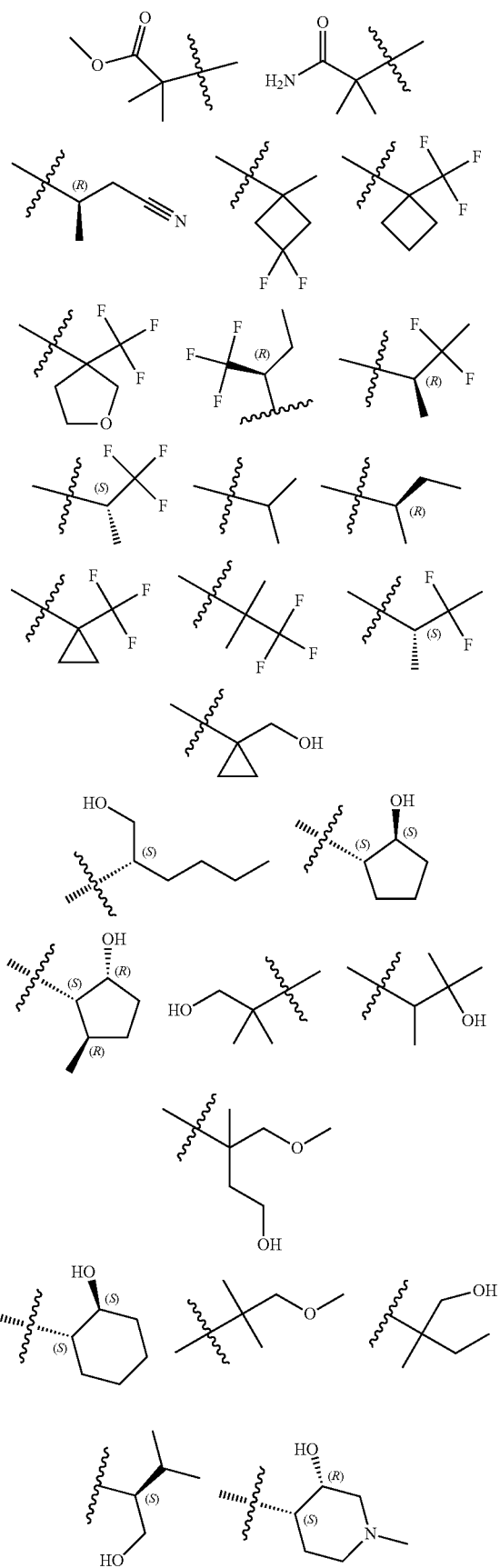

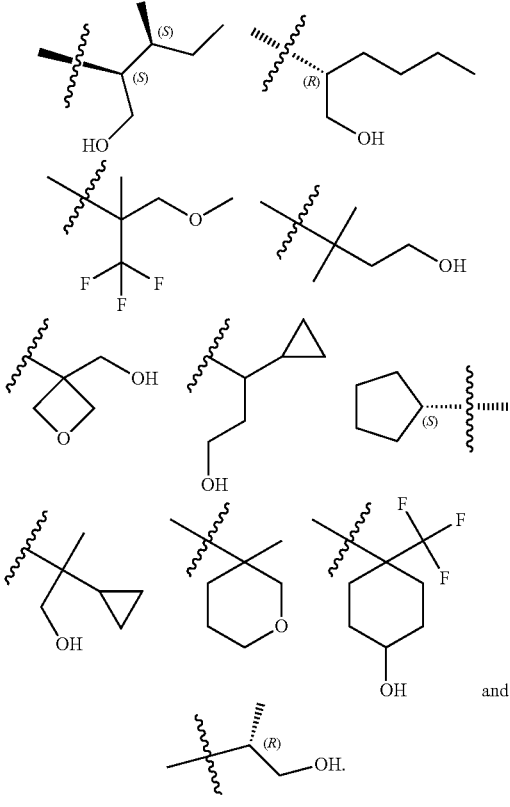

15. The compound according to claim 1, wherein $R^6$ is selected from the group consisting of

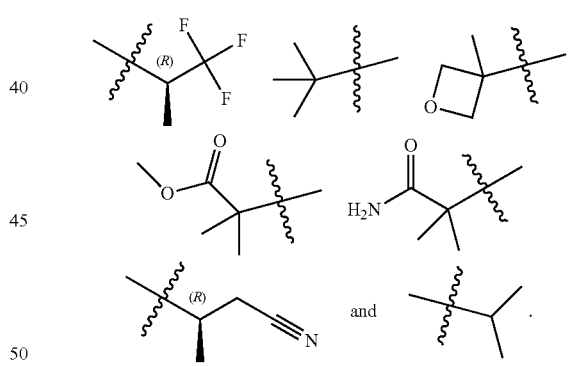

16. The compound according to claim 1, wherein the compound is selected from the group consisting of:

(R)-4-(2-(sec-Butylamino)-2-oxoacetyl)-N-(4-fluoro-3-methylphenyl)-1-methyl-1H-pyrrole-2-carboxamide;

N-(4-Fluoro-3-methylphenyl)-4-(2-(isopropylamino)-2-oxoacetyl)-1-methyl-1H-pyrrole-2-carboxamide;

4-(2-(tert-Butylamino)-2-oxoacetyl)-N-(4-fluoro-3-methylphenyl)-1-methyl-1H-pyrrole-2-carboxamide;

N-(4-Fluoro-3-methylphenyl)-1-methyl-4-(2-(3-methyloxetan-3-yl-amino)-2-oxoacetyl)-1H-pyrrole-2-carboxamide;

(R)—N-(4-Fluoro-3-methylphenyl)-1-methyl-4-(2-oxo-2-(1,1,1-trifluoropropan-2-ylamino)acetyl)-1H-pyrrole-2-carboxamide;

(S)—N-(4-Fluoro-3-methylphenyl)-1-methyl-4-(2-oxo-2-(tetrahydrofuran-3-ylamino)acetyl)-1H-pyrrole-2-carboxamide;

Methyl 2-(2-(5-(4-fluoro-3-methylphenylcarbamoyl)-1-methyl-1H-pyrrol-3-yl)-2-oxoacetamido)-2-methyl-propanoate;

4-{[(2-Amino-1,1-dimethyl-2-oxoethyl)amino](oxo)acetyl}-N-(4-fluoro-3-methylphenyl)-1-methyl-1H-pyrrole-2-carboxamide;

4-[{[(1R)-2-Cyano-1-methylethyl]amino}(oxo)acetyl]-N-(4-fluoro-3-methyl-phenyl)-1-methyl-1H-pyrrole-2-carboxamide;

4-(2-(tert-Butylamino)-2-oxoacetyl)-N-(3,4-difluorophenyl)-1-methyl-1H-pyrrole-2-carboxamide;

N-(3,4-Difluorophenyl)-1-methyl-4-(2-(3-methyloxetan-3-ylamino)-2-oxoacetyl)-1H-pyrrole-2-carboxamide;

4-(2-(tert-Butylamino)-2-oxoacetyl)-1-methyl-N-(3-(trifluoromethyl)-phenyl)-1H-pyrrole-2-carboxamide;

1-Methyl-4-(2-(3-methyloxetan-3-ylamino)-2-oxoacetyl)-N-(3-(tri-fluoro-methyl)phenyl)-1H-pyrrole-2-carboxamide;

4-(2-(tert-Butylamino)-2-oxoacetyl)-N-(3-chloro-4,5-difluorophenyl)-1-methyl-1H-pyrrole-2-carboxamide;

4-(2-(tert-Butylamino)-2-oxoacetyl)-N-(3-cyano-4-fluorophenyl)-1-methyl-1H-pyrrole-2-carboxamide;

N-(3-Cyano-4-fluorophenyl)-1-methyl-4-{[(3-methyloxetan-3-yl)-amino]-(oxo)acetyl}-1H-pyrrole-2-carboxamide;

N-(3-Chloro-4,5-difluorophenyl)-1-methyl-4-{[(3-methyloxetan-3-yl)-amino](oxo)acetyl}-1H-pyrrole-2-carboxamide;

N-(3-Chloro-4,5-difluorophenyl)-1-methyl-4-(oxo{[(1R)-2,2,2-tri-fluoro-1-methylethyl]amino}acetyl)-1H-pyrrole-2-carboxamide;

4-[(tert-Butylamino)(oxo)acetyl]-N-(3-cyano-4-fluoro-phenyl)-1,3,5-trimethyl-1H-pyrrole-2-carboxamide;

4-[(tert-Butylamino)(oxo)acetyl]-N-(3,4-difluorophenyl)-1,3,5-trimethyl-1H-pyrrole-2-carboxamide;

4-[(tert-Butylamino)(oxo)acetyl]-N-(3,4-difluorophenyl)-1,3-dimethyl-1H-pyrrole-2-carboxamide;

4-[(tert-Butylamino)(oxo)acetyl]-N-(3-cyano-4-fluorophenyl)-1,3-dimethyl-1H-pyrrole-2-carboxamide;

4-[(tert-Butylamino)(oxo)acetyl]-3-chloro-N-(3-cyano-4-fluorophenyl)-1-methyl-1H-pyrrole-2-carboxamide;

3-Chloro-N-(3-cyano-4-fluorophenyl)-1-methyl-4-[2-oxo-2-[[(1R)-2,2,2-trifluoro-1-methyl-ethyl]amino]acetyl]pyrrole-2-carboxamide;

5-Bromo-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide;

3-Bromo-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide;

3,5-Dibromo-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide;

N-(3-Cyano-4-fluoro-phenyl)-1,5-dimethyl-4-[2-oxo-2-[[(1R)-2,2,2-trifluoro-1-methyl-ethyl]amino]acetyl]pyrrole-2-carboxamide;

5-Bromo-3-chloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide;

3-Chloro-N-(3-cyano-4-fluoro-phenyl)-1,5-dimethyl-4-[2-oxo-2-[[(1R)-2,2,2-trifluoro-1-methyl-ethyl]amino]acetyl]pyrrole-2-carboxamide;

3-Chloro-N-(3-cyano-4-fluoro-phenyl)-5-cyclopropyl-1-methyl-4-[2-oxo-2-[[(1R)-2,2,2-trifluoro-1-methyl-ethyl]amino]acetyl]pyrrole-2-carboxamide;

4-[2-(tert-Butylamino)-2-oxo-acetyl]-3-chloro-N-(3-cyano-4-fluoro-phenyl)-1,5-dimethyl-pyrrole-2-carboxamide;

4-[2-(tert-Butylamino)-2-oxo-acetyl]-3-chloro-N-(3-cyano-4-fluoro-phenyl)-1-methyl-5-(trifluoromethyl)pyrrole-2-carboxamide;

4-[2-(tert-Butylamino)-2-oxo-acetyl]-N-(3-cyano-4-fluoro-phenyl)-3-fluoro-1-methyl-pyrrole-2-carboxamide;

N-(3-Cyano-4-fluoro-phenyl)-4-[2-[(3,3-difluoro-1-methyl-cyclobutyl)-amino]-2-oxo-acetyl]-3-fluoro-1-methyl-pyrrole-2-carboxamide;

4-[2-(tert-Butylamino)-2-oxo-acetyl]-N-(3-cyano-4-fluoro-phenyl)-3-fluoro-1,5-dimethyl-pyrrole-2-carboxamide;

N-(3-Cyano-4-fluoro-phenyl)-4-[2-[(3,3-difluoro-1-methyl-cyclobutyl)-amino]-2-oxo-acetyl]-3-fluoro-1,5-dimethyl-pyrrole-2-carboxamide;

3-Chloro-N-(3-cyano-4-fluoro-phenyl)-1-methyl-4-[2-oxo-2-[[(1R)-1-(trifluoromethyl)propyl]amino]acetyl]pyrrole-2-carboxamide;

3-Chloro-N-(3-cyano-4-fluoro-phenyl)-1-methyl-4-[2-oxo-2-[[1-(tri-fluoromethyl)cyclobutyl]amino]acetyl]pyrrole-2-carboxamide;

3-Chloro-N-(3-cyano-4-fluoro-phenyl)-4-[2-[(3,3-difluoro-1-methyl-cyclobutyl)amino]-2-oxo-acetyl]-1-methyl-pyrrole-2-carboxamide;

3-Chloro-N-(3-cyano-4-fluoro-phenyl)-1,5-dimethyl-4-[2-oxo-2-[[3-(tri-fluoro-methyl)tetrahydrofuran-3-yl]amino]acetyl]pyrrole-2-carboxamide;

3-Chloro-N-(3-cyano-4-fluoro-phenyl)-1,5-dimethyl-4-[2-oxo-2-[[(1R)-1-(trifluoromethyl)propyl]amino]acetyl]pyrrole-2-carboxamide;

3-Chloro-N-(3-cyano-4-fluoro-phenyl)-1,5-dimethyl-4-[2-oxo-2-[[1-(tri-fluoromethyl)cyclobutyl]amino]acetyl]pyrrole-2-carboxamide;

3-Chloro-N-(3-cyano-4-fluoro-phenyl)-1,5-dimethyl-4-[2-[(3-methyl-oxetan-3-yl)amino]-2-oxo-acetyl]pyrrole-2-carboxamide;

3-Chloro-N-(3-cyano-4-fluoro-phenyl)-4-[2-(isopropylamino)-2-oxo-acetyl]-1,5-dimethyl-pyrrole-2-carboxamide;

3-Chloro-N-(3-cyano-4-fluoro-phenyl)-4-[2-[[(1R)-2,2-difluoro-1-methyl-propyl]amino]-2-oxo-acetyl]-1,5-dimethyl-pyrrole-2-carboxamide;

3-Chloro-N-(3-cyano-4-fluoro-phenyl)-4-[2-[(3,3-difluoro-1-methyl-cyclo-butyl)amino]-2-oxo-acetyl]-1,5-dimethyl-pyrrole-2-carboxamide;

4-[2-(tert-Butylamino)-2-oxo-acetyl]-3-chloro-N-(3-cyano-4-fluoro-phenyl)-5-cyclopropyl-1-methyl-pyrrole-2-carboxamide;

4-[2-(tert-Butylamino)-2-oxo-acetyl]-3-chloro-5-cyano-N-(3-cyano-4-fluoro-phenyl)-1-methyl-pyrrole-2-carboxamide;

5-Bromo-4-[2-(tert-butylamino)-2-oxo-acetyl]-3-chloro-N-(3-cyano-4-fluoro-phenyl)-1-methyl-pyrrole-2-carboxamide;

N-(3-Cyano-4-fluoro-phenyl)-1-methyl-4-[2-oxo-2-[[(1S)-2,2,2-trifluoro-1-methyl-ethyl]amino]acetyl]pyrrole-2-carboxamide;

N-(3-Cyano-4-fluoro-phenyl)-4-[2-(isopropylamino)-2-oxo-acetyl]-1,5-dimethyl-pyrrole-2-carboxamide;

N-(3-Cyano-4-fluoro-phenyl)-1,5-dimethyl-4-[2-[[(1R)-1-methyl-propyl]-amino]-2-oxo-acetyl]pyrrole-2-carboxamide;

N-(3-Cyano-4-fluoro-phenyl)-4-[2-[[(1R)-2,2-difluoro-1-methyl-propyl]-amino]-2-oxo-acetyl]-1,5-dimethyl-pyrrole-2-carboxamide;

N-(3-Cyano-4-fluoro-phenyl)-4-[2-[[(1S)-2,2-difluoro-1-methyl-propyl]-amino]-2-oxo-acetyl]-1,5-dimethyl-pyrrole-2-carboxamide;

N-(3-Cyano-4-fluoro-phenyl)-4-[2-[(3,3-difluoro-1-methyl-cyclobutyl)-amino]-2-oxo-acetyl]-1,5-dimethyl-pyrrole-2-carboxamide;

N-(3-Cyano-4-fluoro-phenyl)-1,5-dimethyl-4-[2-oxo-2-[[1-(trifluoro-methyl)-cyclopropyl]amino]acetyl]pyrrole-2-carboxamide;

N-(3-Cyano-4-fluoro-phenyl)-1,5-dimethyl-4-[2-oxo-2-[(2,2,2-trifluoro-1,1-dimethyl-ethyl)amino]acetyl]pyrrole-2-carboxamide;

4-[2-(tert-Butylamino)-2-oxo-acetyl]-N-(3-cyano-4-fluoro-phenyl)-1,5-dimethyl-pyrrole-2-carboxamide;

N-(3-Cyano-4-fluoro-phenyl)-1,5-dimethyl-4-[2-[(3-methyloxetan-3-yl)-amino]-2-oxo-acetyl]pyrrole-2-carboxamide;

N-(3-Cyano-4-fluoro-phenyl)-5-cyclopropyl-1-methyl-4-[2-oxo-2-[[(1R)-2,2,2-trifluoro-1-methyl-ethyl]amino]acetyl]pyrrole-2-carboxamide;

N-(3-Cyano-4-fluoro-phenyl)-4-[2-[[(3R,4S)-3-hydroxy-1-methyl-4-piperidyl]amino]-2-oxo-acetyl]-1,5-dimethyl-pyrrole-2-carboxamide;

N-(3-Cyano-4-fluoro-phenyl)-4-[2-[[(1S)-1-(hydroxymethyl)pentyl]amino]-2-oxo-acetyl]-1,5-dimethyl-pyrrole-2-carboxamide;

N-(3-Cyano-4-fluoro-phenyl)-1-methyl-4-[2-oxo-2-[[(1R)-2,2,2-trifluoro-1-methyl-ethyl]amino]acetyl]pyrrole-2-carboxamide;

N-(3-Cyano-4-fluoro-phenyl)-4-[2-[[(1S,2S)-2-hydroxy-cyclopentyl]amino]-2-oxo-acetyl]-1,5-dimethyl-pyrrole-2-carboxamide;

N-(3-Cyano-4-fluoro-phenyl)-4-[2-[[(1S,2R,5R)-2-hydroxy-5-methyl-cyclopentyl]amino]-2-oxo-acetyl]-1,5-dimethyl-pyrrole-2-carboxamide;

N-(3-Cyano-4-fluoro-phenyl)-4-[2-[[(1S,2S)-2-hydroxy-cyclohexyl]amino]-2-oxo-acetyl]-1,5-dimethyl-pyrrole-2-carboxamide;

N-(3-Cyano-4-fluoro-phenyl)-4-[2-[[(1S)-1-(hydroxymethyl)-2-methyl-propyl]amino]-2-oxo-acetyl]-1,5-dimethyl-pyrrole-2-carboxamide;

N-(3-Cyano-4-fluoro-phenyl)-4-[2-[[(1S,2S)-1-(hydroxymethyl)-2-methyl-butyl]amino]-2-oxo-acetyl]-1,5-dimethyl-pyrrole-2-carboxamide;

N-(3-Cyano-4-fluoro-phenyl)-4-[2-[[3-hydroxy-1-(methoxymethyl)-1-methyl-propyl]amino]-2-oxo-acetyl]-1,5-dimethyl-pyrrole-2-carboxamide;

N-(3-Cyano-4-fluoro-phenyl)-4-[2-[[3-(hydroxymethyl)oxetan-3-yl]amino]-2-oxo-acetyl]-1,5-dimethyl-pyrrole-2-carboxamide;

N-(3-Cyano-4-fluoro-phenyl)-4-[2-[(2-hydroxy-1,2-dimethyl-propyl)amino]-2-oxo-acetyl]-1,5-dimethyl-pyrrole-2-carboxamide;

N-(3-Cyano-4-fluoro-phenyl)-4-[2-[[1-(hydroxymethyl)cyclopropyl]amino]-2-oxo-acetyl]-1,5-dimethyl-pyrrole-2-carboxamide;

N-(3-Cyano-4-fluoro-phenyl)-4-[2-[(1-cyclopropyl-3-hydroxy-propyl)amino]-2-oxo-acetyl]-1,5-dimethyl-pyrrole-2-carboxamide;

N-(3-Cyano-4-fluoro-phenyl)-4-[2-[[(1R)-1-(hydroxymethyl)pentyl]amino]-2-oxo-acetyl]-1,5-dimethyl-pyrrole-2-carboxamide;

N-(3-Cyano-4-fluoro-phenyl)-4-[-2-[[1-(hydroxymethyl)-1-methyl-propyl]-amino]-2-oxo-acetyl]-1,5-dimethyl-pyrrole-2-carboxamide;

N-(3-Cyano-4-fluoro-phenyl)-4-[2-[(1-cyclopropyl-2-hydroxy-1-methyl-ethyl)amino]-2-oxo-acetyl]-1,5-dimethyl-pyrrole-2-carboxamide;

N-(3-Cyano-4-fluoro-phenyl)-1,5-dimethyl-4-[2-[(3-methyltetrahydropyran-3-yl)amino]-2-oxo-acetyl]pyrrole-2-carboxamide;

N-(3-Cyano-4-fluoro-phenyl)-4-[2-[(2-methoxy-1,1-dimethyl-ethyl)amino]-2-oxo-acetyl]-1,5-dimethyl-pyrrole-2-carboxamide;

N-(3-Cyano-4-fluoro-phenyl)-1,5-dimethyl-4-[2-oxo-2-[[2,2,2-trifluoro-1-(methoxymethyl)-1-methyl-ethyl]amino]acetyl]pyrrole-2-carboxamide;

N-(3-Cyano-4-fluoro-phenyl)-4-[2-[(3-hydroxy-1,1-dimethyl-propyl)amino]-2-oxo-acetyl]-1,5-dimethyl-pyrrole-2-carboxamide;

N-(3-Cyano-4-fluoro-phenyl)-4-[2-[[4-hydroxy-1-(trifluoromethyl)cyclo-hexyl]amino]-2-oxo-acetyl]-1,5-dimethyl-pyrrole-2-carboxamide;

N-(3-Cyano-4-fluoro-phenyl)-3-fluoro-1-methyl-4-[2-oxo-2-[[3-(trifluoro-methyl)tetrahydrofuran-3-yl]amino]acetyl]pyrrole-2-carboxamide;

N-(3-Cyano-4-fluoro-phenyl)-3-fluoro-1-methyl-4-[2-oxo-2-[[1-(trifluoro-methyl)cyclobutyl]amino]acetyl]pyrrole-2-carboxamide;

N-(3-Cyano-4-fluoro-phenyl)-3-fluoro-1-methyl-4-[2-oxo-2-[[(1R)-2,2,2-trifluoro-1-methyl-ethyl]amino]acetyl]pyrrole-2-carboxamide;

3,5-Dichloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide;

5-Chloro-N-(3-cyano-4-fluoro-phenyl)-1-methyl-4-[2-oxo-2-[[(1R)-2,2,2-trifluoro-1-methyl-ethyl]amino]acetyl]pyrrole-2-carboxamide;

5-Chloro-N-(3-cyano-4-fluoro-phenyl)-1-methyl-4-[2-oxo-2-[[(1S)-2,2,2-trifluoro-1-methyl-ethyl]amino]acetyl]pyrrole-2-carboxamide;

5-Chloro-N-(3-cyano-4-fluoro-phenyl)-3-fluoro-1-methyl-4-[2-oxo-2 [[3 (trifluoromethyl)tetrahydrofuran-3-yl]amino]acetyl]pyrrole-2-carboxamide;

5-Chloro-N-(3-cyano-4-fluoro-phenyl)-3-fluoro-1-methyl-4-[2-oxo-2-[[1(trifluoromethyl)cyclobutyl]amino]acetyl]pyrrole-2-carboxamide;

5-Chloro-N-(3-cyano-4-fluoro-phenyl)-3-fluoro-1-methyl-4-[2-oxo-2-[[(1R)-2,2,2-trifluoro-1-methyl-ethyl]amino]acetyl]pyrrole-2-carboxamide;

3-Chloro-N-(3-cyano-4-fluoro-phenyl)-4-[2-[(2-hydroxy-1,1-dimethyl-ethyl)amino]-2-oxo-acetyl]-1-methyl-pyrrole-2-carboxamide;

N-(3-Cyano-4-fluoro-phenyl)-4-[2-[[(1R)-2,2-difluoro-1-methylpropyl]-amino]-2-oxo-acetyl]-3-fluoro-1-methyl-pyrrole-2-carboxamide;

N-(3-Cyano-4-fluoro-phenyl)-4-[2-[(2-hydroxy-1,1-dimethyl-ethyl)amino]-2-oxo-acetyl]-1,5-dimethyl-pyrrole-2-carboxamide;

N-(3-Cyano-4-fluoro-phenyl)-3-fluoro-4-[2-[[(1R)-2-hydroxy-1-methyl-ethyl]amino]-2-oxo-acetyl]-1-methyl-pyrrole-2-carboxamide;

N-(3-Cyano-4-fluoro-phenyl)-3-fluoro-4-[2-[(2-methoxy-1,1-dimethyl-ethyl)amino]-2-oxo-acetyl]-1-methyl-pyrrole-2-carboxamide;

5-Chloro-N-(4-fluoro-3-methyl-phenyl)-1-methyl-4-[2-oxo-2-[[(1S)-2,2,2-trifluoro-1-methyl-ethyl]amino]acetyl]pyrrole-2-carboxamide;

4-[2-(tert-Butylamino)-2-oxo-acetyl]-5-chloro-N-(3-cyano-4-fluoro-phenyl)-1-methyl-pyrrole-2-carboxamide;

N-(3-Cyano-4-fluoro-phenyl)-3-fluoro-4-[2-[(2-hydroxy-1,1-dimethyl-ethyl)amino]-2-oxo-acetyl]-1-methyl-pyrrole-2-carboxamide;

5-Chloro-N-(3-cyano-4-fluoro-phenyl)-1-methyl-4-[2-[(3-methyloxetan-3-yl)amino]-2-oxo-acetyl]pyrrole-2-carboxamide;

N-(3-Cyano-4-fluoro-phenyl)-3-fluoro-1-methyl-4-[2-oxo-2-[[1-(trifluoro-methyl)cyclopropyl]amino]acetyl]pyrrole-2-carboxamide; and N-(3-Cyano-4-fluoro-phenyl)-3-fluoro-4-[2-[[1-(hydroxymethyl)cyclopropyl]amino]-2-oxo-acetyl]-1-methyl-pyrrole-2-carboxamide.

17. A product containing (a) a compound according to claim 16, and (b) at least one HBV inhibitor, as a combined preparation for simultaneous or sequential use in the treatment of HBV infections.

18. A method of treating an HBV infection comprising administering a therapeutically effective amount of at least one compound as claimed in claim 1.

19. A method of treating an HBV infection comprising administering a therapeutically effective amount of at least one compound as claimed in claim 16.

20. A compound of the structure selected from the group consisting of

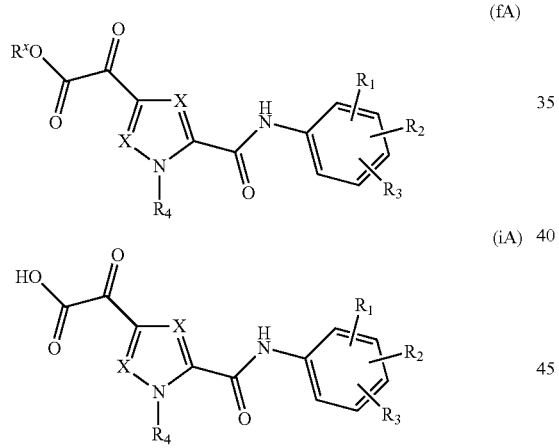

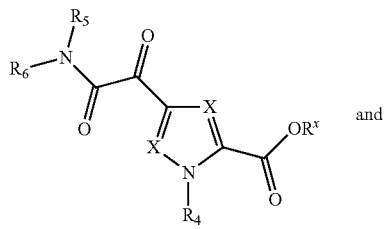

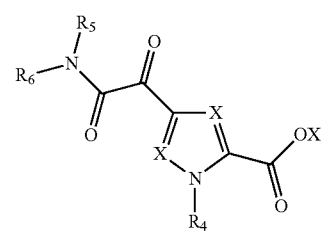

wherein each X independently is $CR^7$;

$R^1$, $R^2$ and $R^3$ are independently selected from the group consisting of hydrogen, fluoro, chloro, bromo, —$CHF_2$, —$CH_2F$, —$CF_3$—CN, $C_1$alkyl and $C_3$-$C_4$cycloalkyl;

$R^4$ is selected from the group consisting of hydrogen, $C_1$-$C_3$alkyl and $C_3$-$C_4$cycloalkyl;

$R^5$ is hydrogen;

$R^6$ is selected from the group consisting of $C_1$-$C_6$alkyl and a 3-7 membered saturated ring optionally containing one or more heteroatoms each independently selected from the group consisting of O, S and N, said $C_1$-$C_6$alkyl or said 3-7 membered saturated ring is optionally substituted with one or more substituents selected from the group consisting of fluoro, $C_3$-$C_4$cycloalkyl, —$OR^8$, oxo, —CN, —C(=O)—$OR^8$, —C(=O)—$N(R^8)_2$ and $C_1$-$C_3$alkyl, wherein said $C_1$-$C_3$alkyl is optionally substituted with one or more fluoro;

each $R^7$ is independently selected from the group consisting of hydrogen, $C_3$-$C_4$cycloalkyl, —CN, fluoro, chloro, bromo and $C_1$-$C_3$alkyl, wherein said $C_1$-$C_3$alkyl is optionally substituted with one or more fluoro;

$R^8$ is hydrogen or $C_1$-$C_3$alkyl; and $R^x$ independently is $C_1$-$C_3$alkyl.

* * * * *